United States Patent
Gilmer et al.

(10) Patent No.: US 9,670,223 B2
(45) Date of Patent: Jun. 6, 2017

(54) COMPOUNDS WITH SUPER-ASPIRIN EFFECTS

(71) Applicant: SOLVOTRIN THERAPEUTICS LTD., Cork (IE)

(72) Inventors: John Francis Gilmer, Dublin (IE); Mark Ledwidge, Cork (IE); Pat O'Flynn, Cork (IE); Shona Harmon, Dublin (IE); Marek Radomski, Dublin (IE); Carlos Medina Martin, Dublin (IE)

(73) Assignee: SOLVOTRIN THERAPEUTICS LTD., Cork (IE)

( * ) Notice: Subject to any disclaimer, the term of this patent is extended or adjusted under 35 U.S.C. 154(b) by 0 days.

(21) Appl. No.: 14/681,889

(22) Filed: Apr. 8, 2015

(65) Prior Publication Data
US 2015/0291615 A1 Oct. 15, 2015

Related U.S. Application Data

(63) Continuation of application No. 13/980,533, filed as application No. PCT/EP2012/050888 on Jan. 20, 2012, now abandoned.

(30) Foreign Application Priority Data

Jan. 21, 2011 (IE) .................................... 2011/0025

(51) Int. Cl.
C07D 493/04 (2006.01)

(52) U.S. Cl.
CPC .................................. *C07D 493/04* (2013.01)

(58) Field of Classification Search
CPC ........ C07D 493/04; A61P 29/00; A61P 35/00; A61K 31/34
(Continued)

(56) References Cited

U.S. PATENT DOCUMENTS 8,486,974 B2 * 7/2013 Gilmer .................. 514/338
8,834,858 B2 * 9/2014 Ledwidge ............ A61K 31/192
424/78.01
(Continued)

FOREIGN PATENT DOCUMENTS

JP 2004217600 * 8/2004
WO WO9817673 * 4/1998
(Continued)

OTHER PUBLICATIONS

Gilmer; European Journal of Pharmaceutical Sciences 16 (2002) 297-304.*
(Continued)

*Primary Examiner* — Noble Jarrell
*Assistant Examiner* — Daniel Carcanague
(74) *Attorney, Agent, or Firm* — Foley & Lardner LLP; Antoinette F. Konski

(57) ABSTRACT

A compound having the structural formula (I) and pharmaceutically acceptable salt and/or hydrates thereof, (I) wherein Y is an arylester or an $C_1$-$C_8$ alkylaryl ester, selected from the group consisting of: benzene, toluene, xylene, benzoic acid, benzoate, nicotinate, isonicotinate and halobenzene, which can be unsubstituted or substituted with at least one nitric oxide releasing group; and/or at least one of hydroxide, —Cl, —Br, a $C_1$-$C_8$ alkyl, benzyl, a $C_1$-$C_8$ alkoxy, benzyloxy, —NHC(O)R, —NH$_2$, —NO$_2$, —ONO$_2$, —(CH$_2$)$_n$ONO$_2$, —OC(O)[(CH$_2$)m], cyclic ONO$_2$, —OCOArONO$_2$, —OCOAr(CH$_2$)$_n$ONO$_2$ or a $C_1$-$C_5$ haloalkyl ester, wherein R is a $C_1$-$C_8$ alkyl or a $C_1$-$C_8$ alkoxy group, n=1-8 and m=3-10, to produce a super-aspirin effect.

3 Claims, 26 Drawing Sheets

(58) Field of Classification Search
USPC .............. 514/470, 338; 549/464; 546/284.1
See application file for complete search history.

(56) References Cited

U.S. PATENT DOCUMENTS

| | | | |
|---|---|---|---|
| 2007/0228326 A1* | 10/2007 | Goldfinger | C09K 19/2007 252/299.01 |
| 2007/0267599 A1* | 11/2007 | Goldfinger | C07D 493/04 252/299.01 |
| 2014/0024681 A1* | 1/2014 | Gilmer | C07D 493/04 514/338 |

FOREIGN PATENT DOCUMENTS

| WO | WO2009023759 | * | 2/2009 |
|---|---|---|---|
| WO | WO 2009/080795 A1 | | 7/2009 |
| WO | WO 2012/017321 A2 | | 2/2012 |

OTHER PUBLICATIONS

Jones; J. Med. Chem. 2009, 52, 6588-6598.*
U.S. Appl. No. 13/980,533, filed Oct. 7, 2013, Gilmer et al.
Moriarty, L.M. et al. (2008) "Discovery of a 'True' Aspirin Prodrug," J. Med. Chem. 51:7991-7999.
Taubert, D. et al. (2004) "Aspirin induces nitric oxide release from vascular endothelium: a novel mechanism of action," British Journal of Pharmacology 143:159-165.
International Search Report (ISA/EPO) for International Application No. PCT/EP2012/050888, mailed Apr. 5, 2012, 2 pages.
Restriction Requirement for U.S. Appl. No. 13/980,533, mailed Jul. 24, 2014, 9 pages.
Non-Final Office Action for U.S. Appl. No. 13/980,533, mailed Oct. 9, 2014, 16 pages.

* cited by examiner

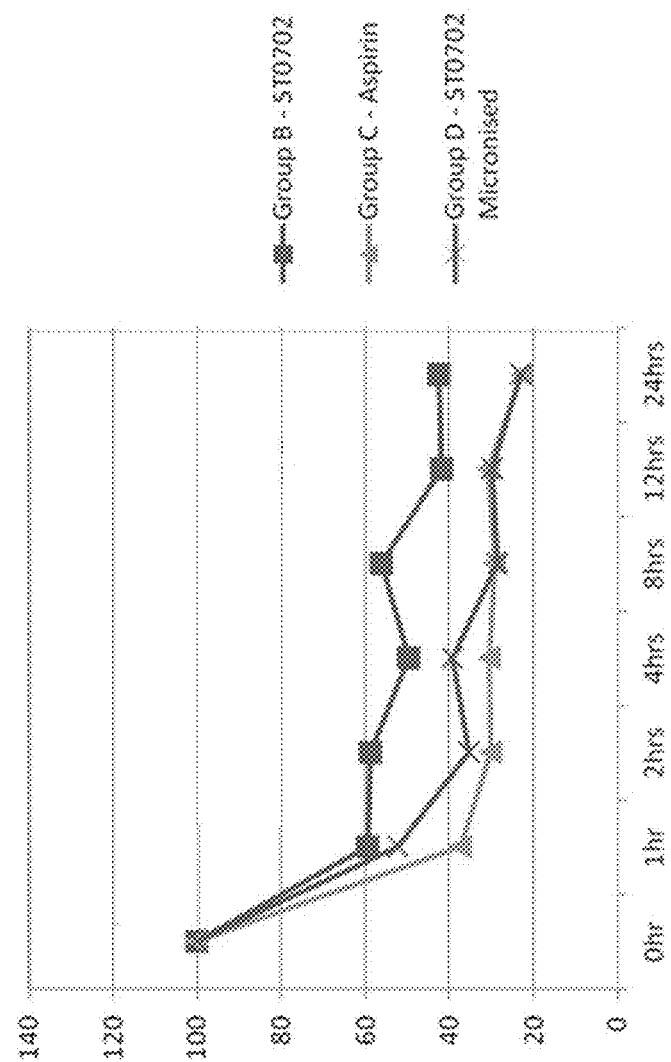

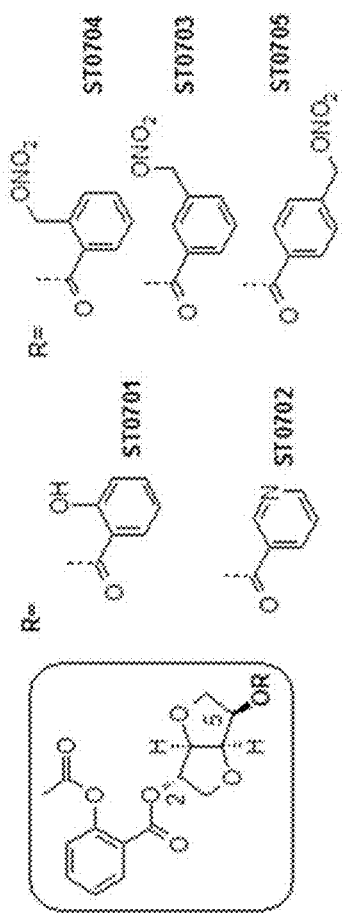
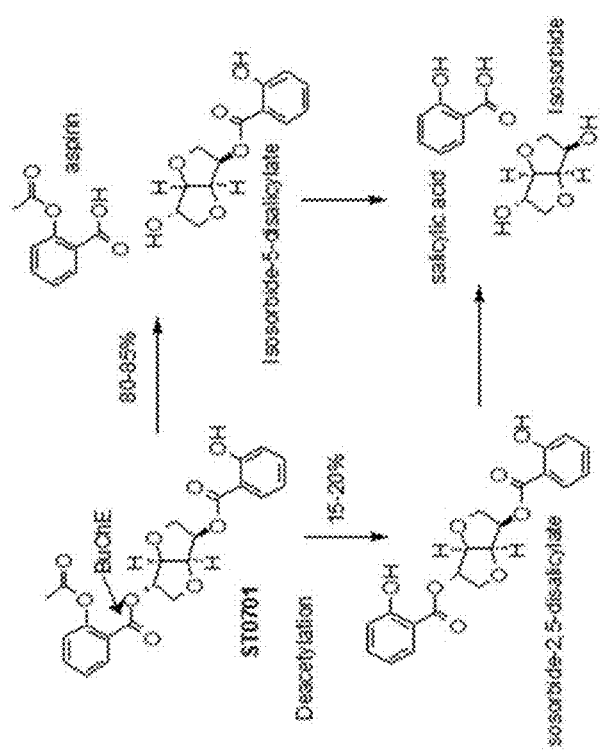
FIG. 2A
FIG. 2B

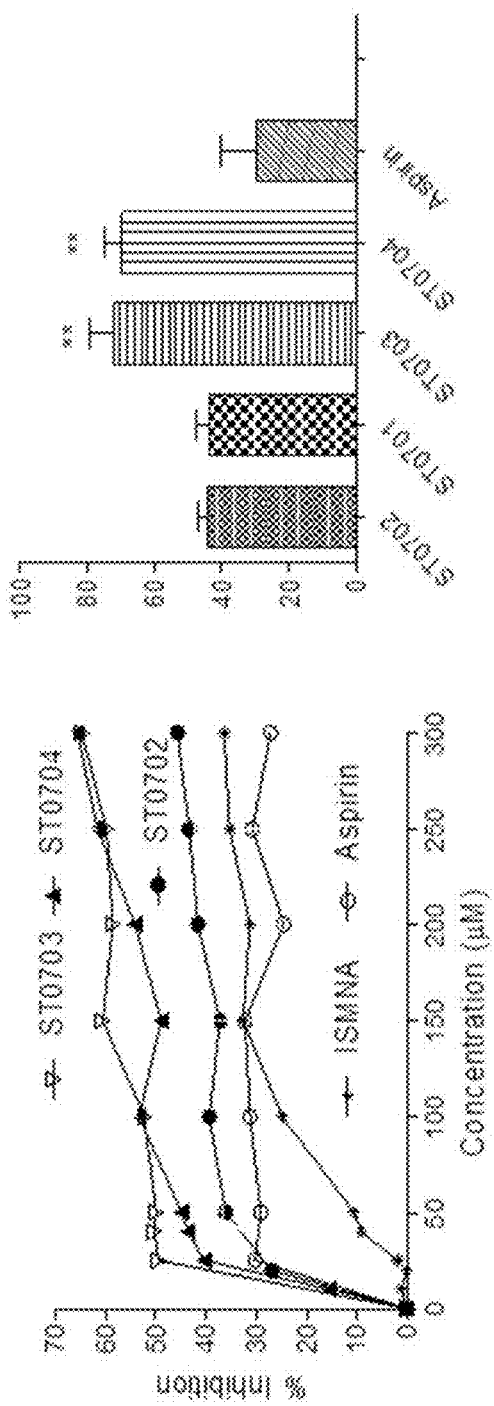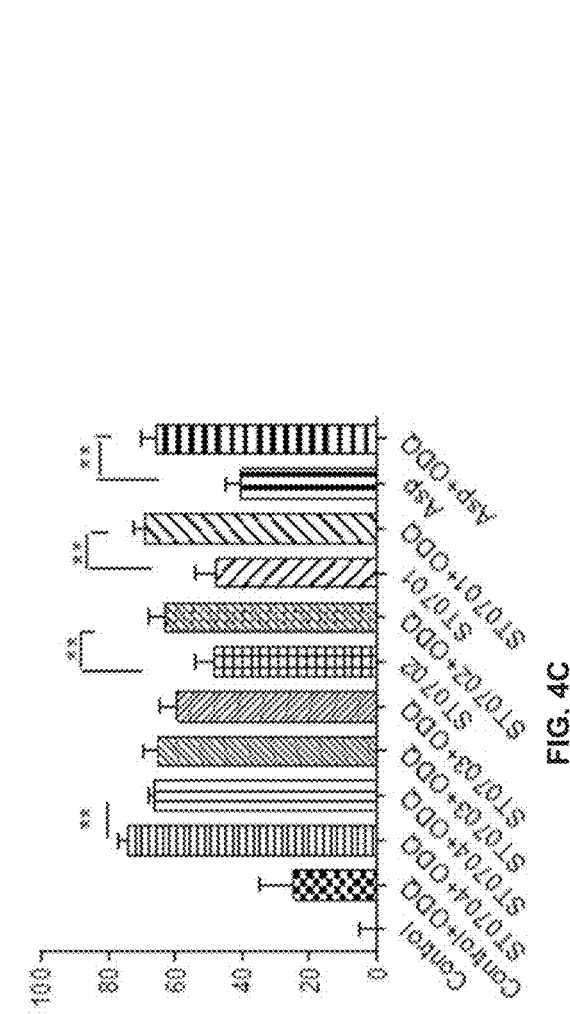
FIG. 4A
FIG. 4B
FIG. 4C

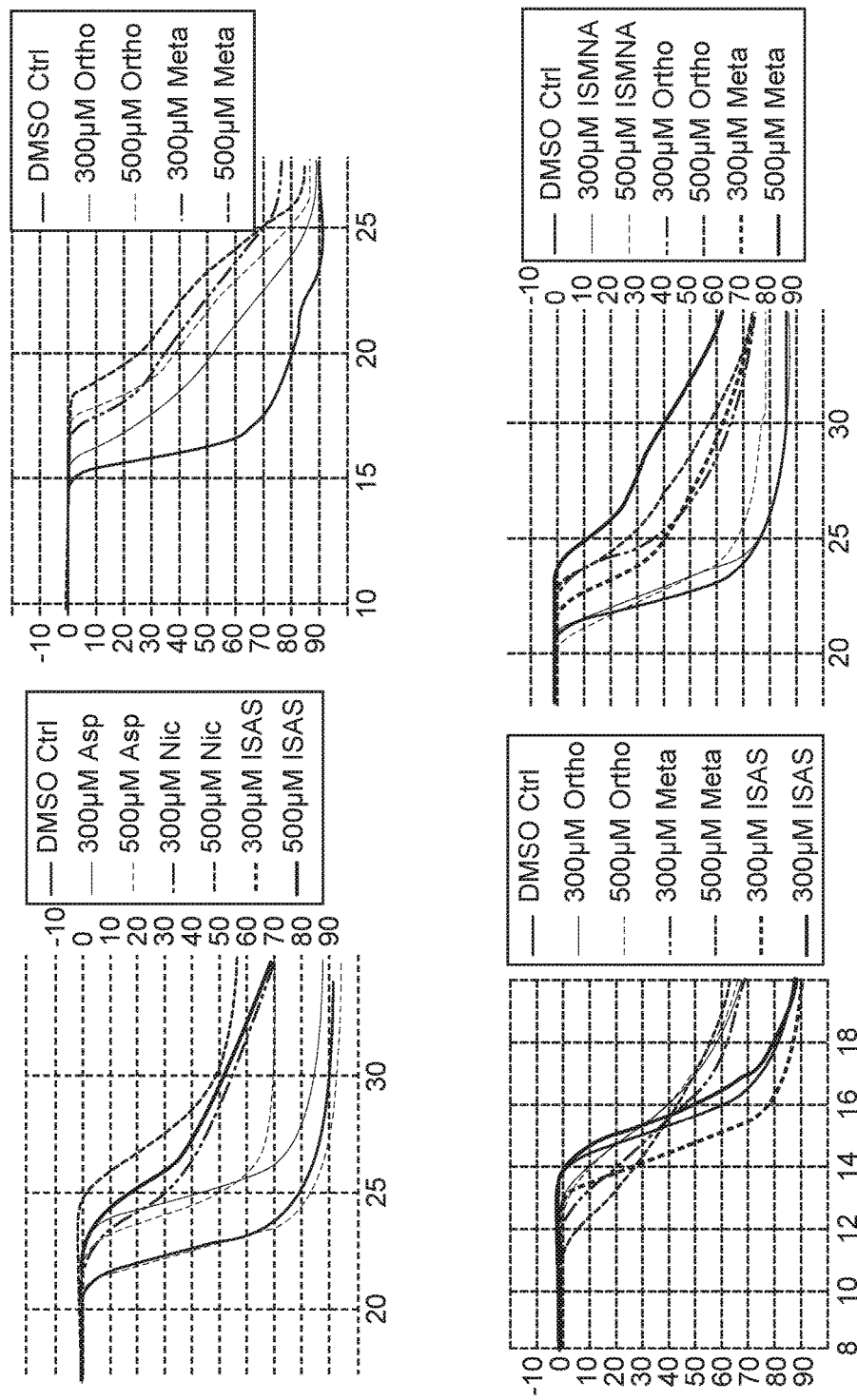
FIG. 10A (Cont. 1)

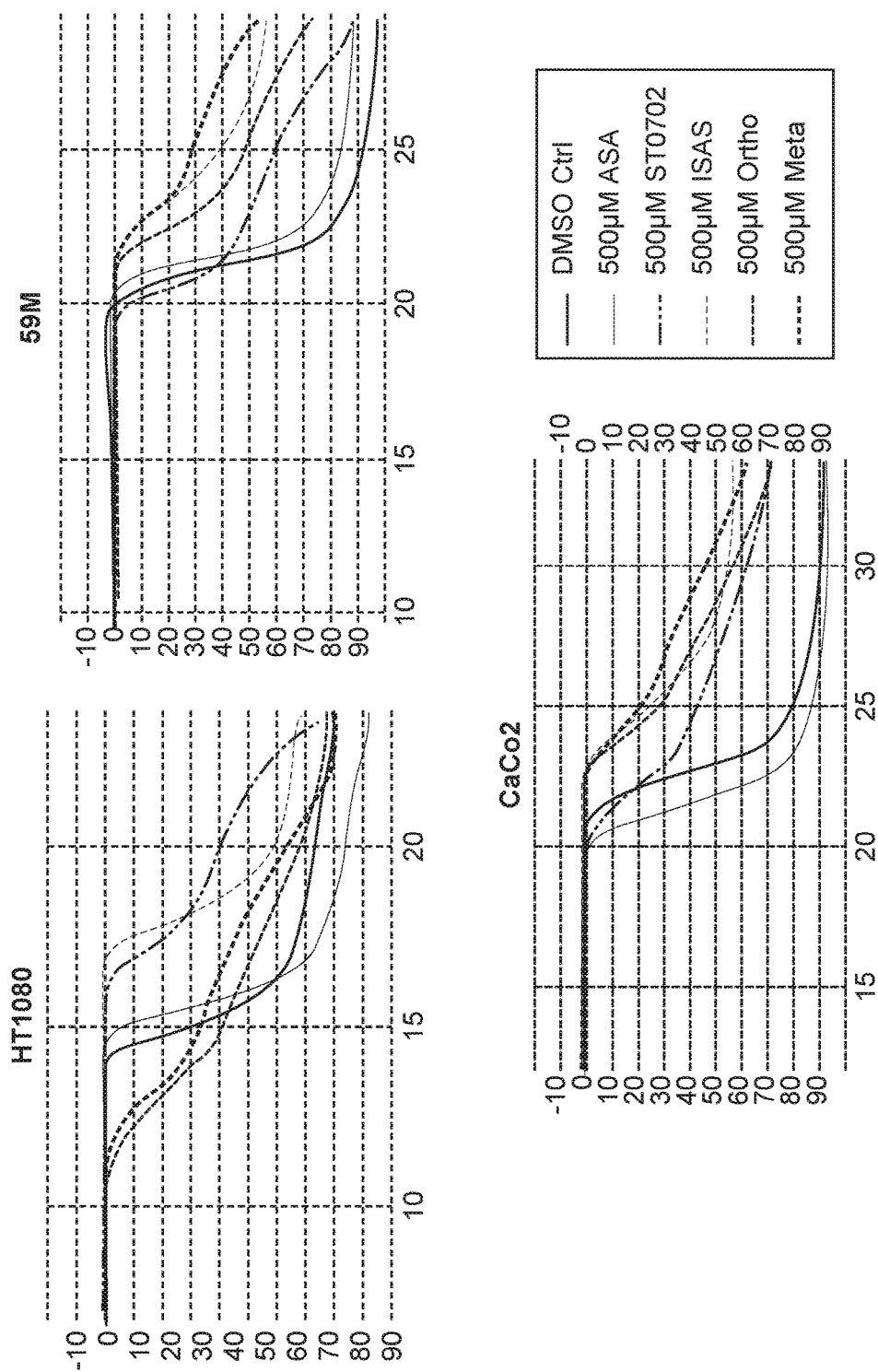
FIG. 10A (Cont. 2)

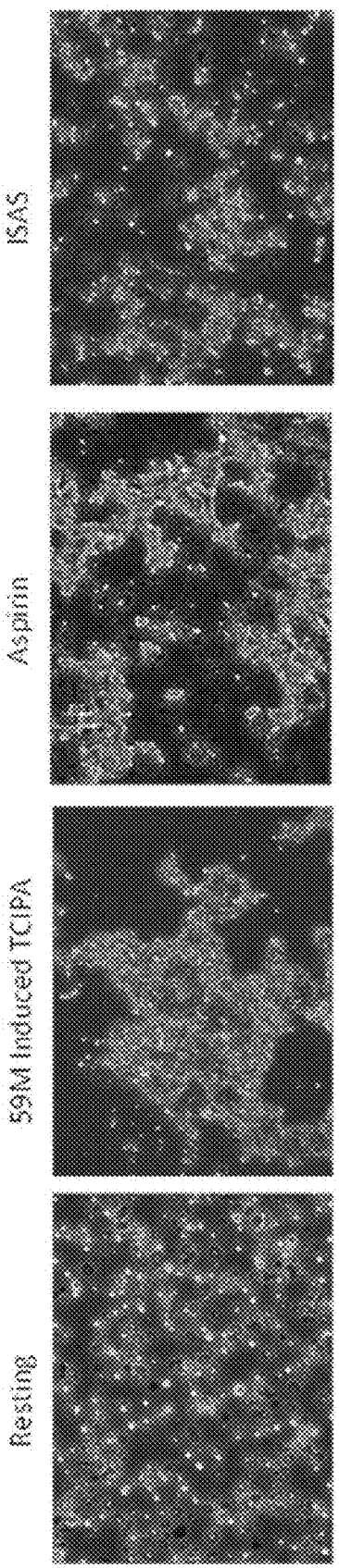
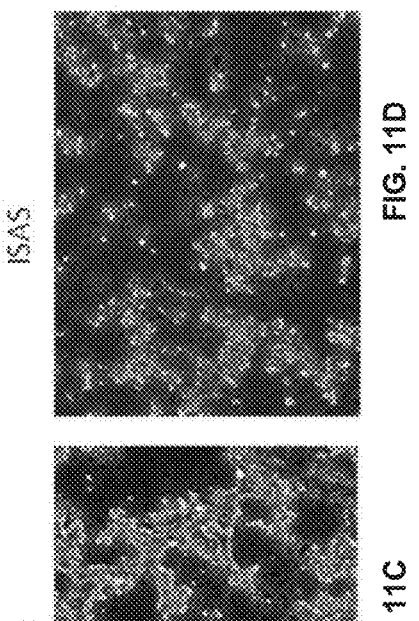
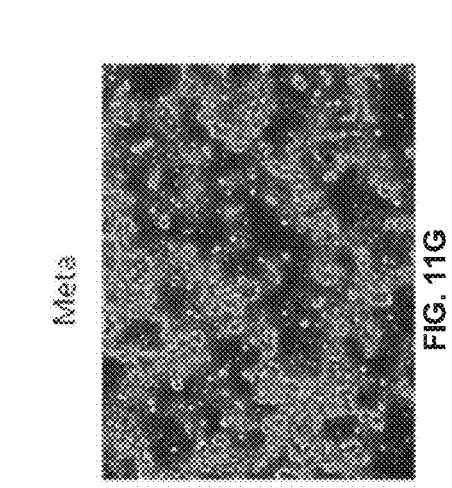
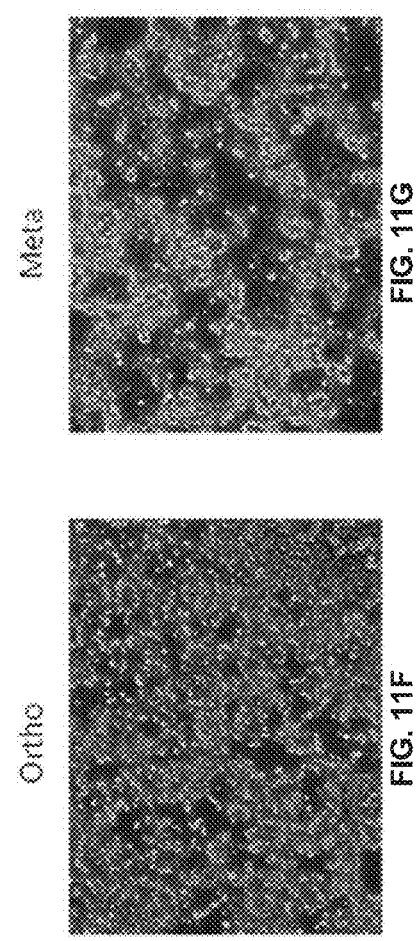
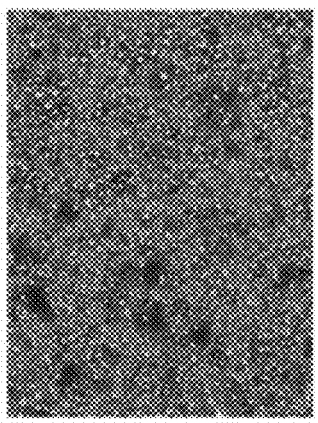
FIG. 11A FIG. 11B FIG. 11C FIG. 11D FIG. 11E FIG. 11F FIG. 11G

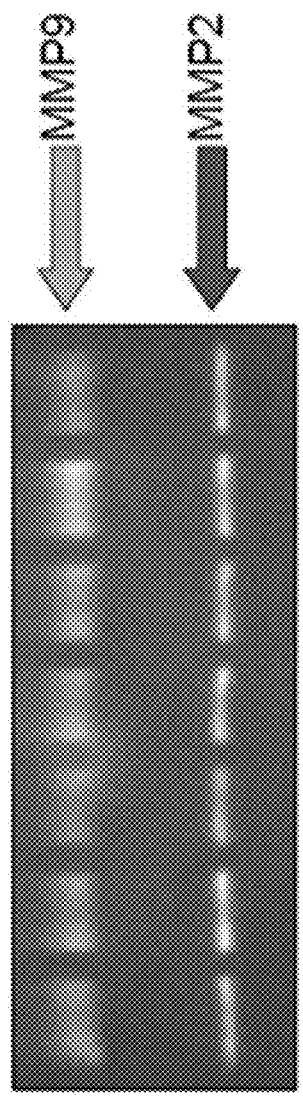
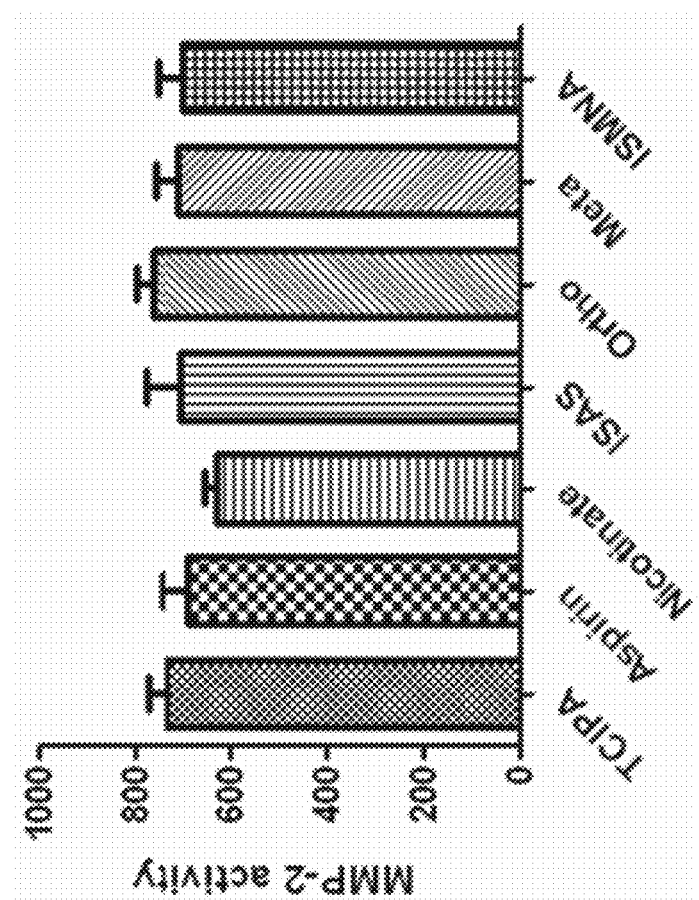
FIG. 12A
FIG. 12B

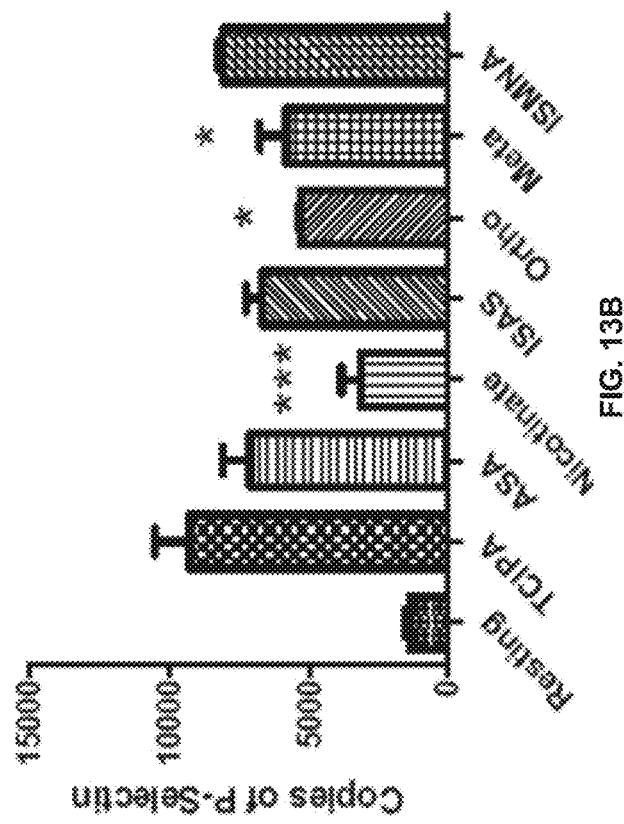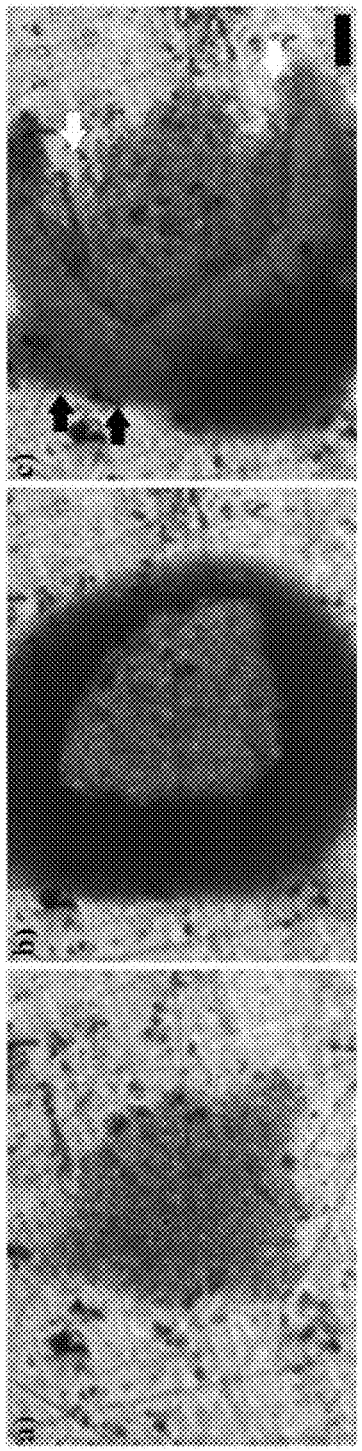

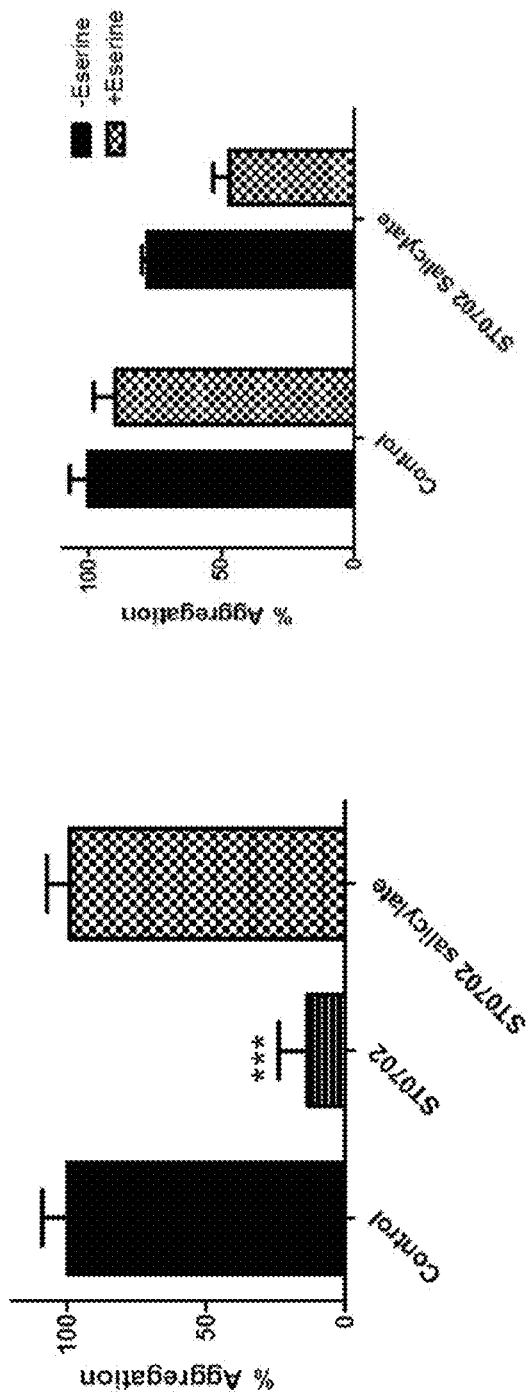
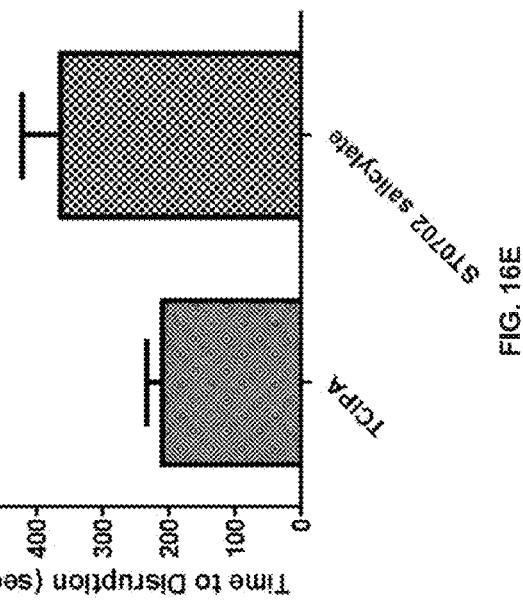

COMPOUNDS WITH SUPER-ASPIRIN EFFECTS

CROSS-REFERENCE TO RELATED APPLICATIONS

This application is a continuation of U.S. application Ser. No. 13/980,533, filed Oct. 7, 2013, which is a national phase application under 35 U.S.C. §371 of International Application No. PCT/EP2012/050888, filed Jan. 20, 2012, which in turn claims priority to Irish Application No. 2011/0025, filed Jan. 21, 2011, the entire content of each of which is incorporated herein by reference.

FIELD OF THE INVENTION

The invention relates to aspirin prodrug compounds that are capable of providing a super-aspirin effect which provides an additional antiplatelet effect over the antiplatelet effect of any aspirin released. In particular, the compounds are useful in conditions where aspirin has traditionally thought to be ineffective, such as conditions where inhibition of tumor cell induced platelet aggregation (TCIPA) is desired. The compounds may be used in cardiovascular and/or anticancer applications.

DESCRIPTION OF RELATED ART

Aspirin is an effective antiplatelet drug, reducing the risk of myocardial infarction (MI), stroke or death by approximately 25% in patients who are at increased risk of cardiovascular (CV) events. However, in some cases less than expected inhibition of platelets by aspirin has been referred to as aspirin resistance.[a] Aspirin resistance levels have been reported to range from 5 to 63% in various studies.[b,c]

A number of potential mechanisms have been proposed for this including poor compliance, reduced enteral absorption of aspirin, loss of antiplatelet effect during long-term aspirin treatment (tachyphylaxis), impaired suppression of platelet COX-1, inadequate dose, increased platelet turnover, COX polymorphisms, impaired suppression of urinary 1-dehydrothromboxane B2 (aspirin bypass), COX-1 and COX-2 independent pathways of AA-induced platelet activation, non-atherothrombosis pathology, and platelet reactivity and response to aspirin according to sex.[a] Of these, compliance appears to be the most significant, whereby up to 40% of patients with cardiovascular disease do not comply with aspirin therapy.[a] The results of one study suggest that the most aspirin resistance may be largely due to non-compliance.[b] In a 2010 study, aspirin resistance of 34% using at least one test and 25% for a specific platelet function test were obtained, and nearly half of these due to poor compliance.[e] A large proportion of patients thought to be resistant to aspirin are actually "pseudo-aspirin resistant" due to non-compliance. For example in one study there were twice as many patients (8.4%) classified as "pseudo-resistant" compared to actually resistant patients (3.4%).[h] When compliant, the "pseudo-resistant" patients were no longer so. Another study demonstrated that on initial review of patients post-MI it appeared that 9% of patients were resistant, but when aspirin ingestion was observed it was shown that these 9% were due to non-compliance.[i]

Causes of non-compliance with aspirin are well described. In a meta-analysis in 2010 of 32 studies and >144,800 patients, it was shown that adverse events were the reason for low dose aspirin discontinuation in almost 50% of patients. In this meta analysis poor compliance ranged from 10% to over 50% of patients and patient-initiated discontinuation of therapy occurred in up to 30% of patients.[g] A review article confirms that the relatively high rate of gastrointestinal (GI) complications with aspirin and patients awareness of such symptoms, often make aspirin a "first choice to stop" drug from an often long list of prescribed medicines.[h]

Adherence to daily aspirin doses has also been looked at in cancer chemoprevention trials. In a study looking at doses from up to 640 mg, the adherence rate was 35%. In another chemoprevention trial, it was shown that despite using highly motivated, well educated patients, adherence was poor.[j]

Enteric coated aspirin does not solve the aspirin resistance problem. Aspirin is released from these formulations in the upper part of the small intestine where the pH exceeds the drug's pKa and so aspirin is less protonated and absorbable. In one study, 44% of patients with stable CV disease that were treated with enteric coated aspirin 75 mg/day had persistent uninhibited COX-1 activity. Also, delayed enteral absorption of aspirin increases the potential for aspirin esterases in the GI mucosa to hydrolyse aspirin to salicylic acid before entering the portal circulation and thereby reduce the effect of the administered dose.[a] Another study showed that in patients prescribed aspirin within the previous 72 hours, with enteric coating, 65% of patients still had normal platelet function in comparison to 25% taking an uncoated preparation. Similarly, low dose could be an issue with 56% of aspirin doses 81-162 mg/day versus 28% of patients taking ≥325 mg/day still had normal platelet function.[k]

Finally a number of genetic and disease states are associated with aspirin resistance. For example, a number of disease states demonstrate increased platelet turnover which can cause aspirin resistance. These states associated with infection, inflammation and major surgery can lead to an increased proportion of non-aspirinated platelets.[a] Other conditions of relevance where increased platelet turnover occurs include acute myocardial infarction and coronary artery bypass grafting. In one report, aspirin resistance levels of 83.3% were found in patients presenting with STEMI. Patients who have persistent aspirin resistance (not associated with compliance, dose form and platelet turnover) may be as low as 6% and this may be as a result of genetic polymorphisms.[b] In these situations, having a therapeutic approach which involves non-aspirin antiplatelet effects are clinically beneficial.

Therefore, aspirin resistance is a major public health problem affecting up to half of patients. A number of potential causes for aspirin resistance have been described. Of these, compliance appears to be the greatest issue. A second major issue appears to be lack of efficacy of clinically popular enteric coated versions of low dose aspirin, which is not seen with immediate release aspirin and higher doses. Finally, in the remainder of aspirin resistance states, the ability to inhibit platelet aggregation using non-aspirin mechanisms is important.

True aspirin ester prodrugs are compounds designed to undergo processing in human blood, producing aspirin. They are of interest firstly because they are predicted to be less toxic to the intestinal tract than aspirin. Aspirin's acid group is associated with its topical irritancy, with ion trapping and with COX-1/COX-2 inhibition. Esterification blunts the topical irritancy effect, suppresses ion trapping and is predicted to abolish local COX inhibitory effects. Aspirin prodrugs also hold promise for addressing some of the efficacy deficits of the parent drug. Aspirin fails to prevent atherothrombotic events in the majority of patients (75-80%) with symptomatic atherothrombotic disease. This is a complex problem that is partly due to poor compliance (which is linked to intestinal toxicity) but it is also a reflection of the multi-factorial nature of cardiovascular disease which demands multiple pharmacological responses.

Recently, the present inventors reported on the first 'true' aspirin prodrug, isosorbide-2-aspirinate-5-salicylate (ISAS), ST0701 (FIG. 2A)[6]. This is activated very rapidly in solutions containing human plasma butyrylcholinesterase (BuChE, EC 3.1.1.8) because of a highly specific interaction with BuChE. ST0701 undergoes parallel processing in plasma generating the isosorbide disalicylate (15%) (FIG. 2B). Normally aspirin esters are processed exclusively along this route which abolishes platelet inhibitory properties. By taking account of esterase preferences, it was possible to design hybrid compounds able to release a second active moiety relevant to cardiovascular disease[7]. In human plasma solution, compound isosorbide-2-aspirinate-5-nicotinate (ISANA) ST0702 (FIG. 2A) releases aspirin (30-45%) and nicotinic acid (Niacin). Nicotinic acid increases High Density Lipoprotein cholesterol (HDL) and reduces low density lipoprotein cholesterol and triglycerides. Moreover, nicotinic acid is the pharmacological agent of choice for reduction of elevated lipoprotein (a), a new treatment target in cardiovascular disease.[10] Meanwhile, the nitrate hybrids (compounds ST0702-04: FIG. 2A) were designed by the present Inventors to release an organic nitrate and aspirin (NO-aspirin). NO is gastroprotective through multiple mechanisms: by promoting blood flow, removing toxins, and stimulating mucus secretion and angiogenesis. Nitric oxide is also a potent vasodilator and it inhibits platelet and monocyte adhesion and platelet aggregation. The combination with aspirin has been extensively investigated with interesting outcomes that support the gastro-protective proposition.

Puzzlingly, aspirin ester prodrugs consistently exhibit greater inhibition of platelet aggregation in vitro than expected based on aspirin to salicylic production in plasma and blood. ST0701, for example is a significantly more potent inhibitor of platelet aggregation than aspirin in whole blood in response to arachidonic acid and in platelet rich plasma (PRP) stimulated with collagen (5 mg/ml); it is also and more efficacious than aspirin with respect to stimulation by ADP (3 μM)[6,7]. It should be noted that cardiovascular disease and cancer are the leading causes of death in the Western World. Thrombosis is the most frequent complication and a major cause of death in cancer patients. In contrast to the large body of literature on venous thromboembolism, relatively few reports have focused on the pathogenesis and incidence of arterial thromboembolic events in patients with malignancy. The presence of comorbidities including pulmonary disease, renal disease, infection, blood transfusion, chemotherapy and obesity are associated with a higher risk of arterial events. There is no difference in incidence between subgroups divided by type of malignancy and presence or absence of metastatic disease. Reported events include ACS, stroke and peripheral artery thromboembolism.

In addition to the typical causes of arterial ischemia related to traditional cardiovascular conditions, patients with underlying malignancy or hematologic disorders have added risks for in situ thrombosis related to the inherent thrombophilia associated with their malignancy and its therapy. Malignancy is a common cause of acquired thrombophilia. Complex mechanistic etiologies have been implicated in this process; however, a key initiating factor is the release of procoagulants such as tissue factor and cancer procoagulant, which activate factor X and the clotting cascade. Inflammatory cytokines secreted by tumor cells lead to endothelial dysfunction and prime the vascular endothelium into a prothrombotic state. Patients with malignancy also have increased levels of clotting factors (fibrinogen, factors V, VIII, IX, XII), thrombocytosis, impaired fibrinolytic activity, and decreased protein C and S levels (Sanon 2010). Acute ischemic arterial events may also have an embolic etiology. Non-bacterial thrombotic endocarditis (NBTE), tumour-cell emboli and paradoxical embolus from DVT through a patent foramen ovale are typical examples of embolic etiologies in these patients (Sanon 2010).

Furthermore, it has been known for over a century that the interactions between tumor cells and platelets are crucial for the hematogenous spread of cancer, but only recently these interactions are being studied more carefully (Jurasz et al., 2004). Growing evidence suggests that successful metastatic spread may depend on the ability of tumor cells to undergo extensive interactions with platelets (2004; Jurasz et al., 2004). In fact, cancer cells have the ability to induce platelet aggregation that confers several advantages to the survival of the tumor cells and its successful metastasis). Moreover, this ability to aggregate platelets called tumor cell-induced platelet aggregation (TCIPA) correlates with the metastatic potential of tumour cells (Radomski et al., 1991). Therefore, platelet aggregation inhibition may slow down the rate of tumor progression and metastasis.

There is evidence that tumour cells have the ability to stimulate the release of platelet granules leading to the liberation of several pro-aggregatory agents, such as $TXA_2$, ADP and matrix metalloproteinase-2 (Alonso-Escolano et al., 2004; 1996; Medina et al., 2006a). In addition, the implication of the different platelet receptors such as GPIb, GPIIb/IIIa and P-selectin in TCIPA has been reported (Alonso-Escolano et al., 2004; Medina et al., 2006a;). GPIb, the von Willebrand factor (VWF)-binding subunit of the GPIb/V/IX, mediates mainly platelet adhesion, GPIIb/IIIa plays an important role in platelet aggregation and P-selectin mediates platelet-leukocyte aggregation.

In platelets, one of the most important mediators regulating haemostasis is $TXA_2$. Indeed, $TXA_2$ promotes thrombosis by aggregating platelets and constricting blood vessels. However, clinical trials of the antiplatelet agent aspirin which inhibits platelet cyclooxygenase and thereby $TXA_2$ production, have proven inconclusive in cancer patients.

Indeed some clinical studies have found that treatment with high doses of aspirin did not protect patients from metastasis.

In addition, aspirin has also failed in preventing TCIPA in vitro with different tumour cell lines (Alonso-Escolano et al., 2003; Jurasz et al., 2001; Medina et al., 2006). Indeed, aspirin itself does not have intrinsic activity against cancer metastasis and has failed in preventing TCIPA in vitro with different tumour cell lines. Nevertheless, aspirin use has been strongly associated with reduced risk of colorectal adenoma and to a lesser extent with reduction in cancers of the upper intestine, oesophagus, breast and lung.

In view of the forgoing, there is a need for aspirin prodrug compounds with multiple activities, such as cardiovascular and chemoprotective activities, together with activity against active cancer tumors and their invasive cells. Furthermore, it would be desirable to provide such aspirin prodrug compounds, having enhanced antiplatelet activity, over that associated with aspirin release. Such multi-activity or "super-aspirin" prodrugs would be invaluable in CVD patients displaying aspirin resistance, and in CVD patients who are at risk of thrombosis events associated with malignancy as the prodrug could be used to target CVD states, and to prevent and/or treat active cancer tumors. Thus, it would be desirable to provide a series of aspirin prodrugs having "super-aspirin" activities, to provide concurrent cardioprotective and chemoprotective benefits and that have anti-metastasis action on existing cancer tumors. Such multi action drugs could be used in cardiovascular and/or cancer applications to prevent and treat cancer metastasis and lower risk of CV incidents in this patient group.

SUMMARY OF THE INVENTION

According to the present invention, as set out in the appended claims, there is provided at least one compound having the general structural formula (I) and pharmaceutically acceptable salt and/or hydrates thereof,

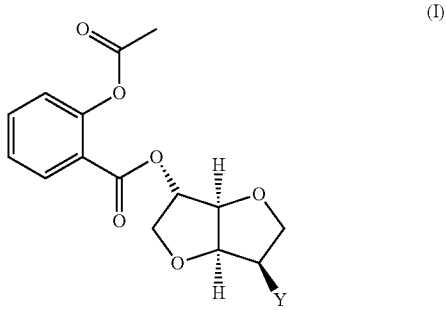

(I)

wherein Y is an arylester or an $C_1$-$C_8$ alkylaryl ester, selected from the group consisting of: benzene, toluene, xylene, benzoic acid, benzoate, nicotinate, isonicotinate and halobenzene, which can be unsubstituted or substituted with
at least one nitric oxide releasing group; and/or
at least one of hydroxide, —Cl, —Br, a $C_1$-$C_8$ alkyl, benzyl, a $C_1$-$C_8$ alkoxy,
benzyloxy, —NHC(O)R, —NH$_2$, —NO$_2$, —ONO$_2$, —(CH$_2$)$_n$ONO$_2$, —OC(O)[(CH$_2$)$_m$]$_{cyclic}$ONO$_2$, —OCOArONO$_2$, —OCOAr(CH$_2$)$_n$ONO$_2$ or a $C_1$-$C_5$ haloalkyl ester, wherein R is a $C_1$-$C_8$ alkyl or a $C_1$-$C_8$ alkoxy group, n=1-8 and m=3-10, for concurrently producing an aspirin effect and an additional antiplatelet aggregation effect, the effects together termed a "super-aspirin effect". It will be appreciated that the compounds can be used in a method of concurrently producing an aspirin effect and an additional antiplatelet aggregation effect.

The compounds may be used in the methods and uses of the invention to concurrently produce an aspirin effect and an additional antiplatelet effect (that is not attributable to aspirin), the dual effects together termed a "super-aspirin effect". By "super-aspirin" effect, it is meant that compound is concurrently a (i) potent inhibitor of ADP and collagen-induced platelet aggregation, and is (ii) capable of treating cancer metastasis by inhibiting tumor cell induced platelet aggregation (TCIPA) (additional antiplatelet effect).

The invention thus relates to aspirin prodrug compounds that are capable of providing a super-aspirin effect, that is, by concurrently produce an aspirin effect and an additional antiplatelet effect over the antiplatelet effect produced by aspirin release from the prodrug. It has been found that because platelets are activated by multiple pathways, these additional non-aspirin antiplatelet aggregation effects supplement the aspirin effects to reduce platelet activation. This is particularly in disease states with high levels of inflammation or in patients with genetic polymorphisms that render them aspirin resistant. The compounds are particularly suitable for aspirin applications in aspirin resistance patients. For example, the compounds are suitable for the inhibition of cancer cell metastasis tumor cell induced platelet aggregation (TCIPA). The compounds are superior to aspirin, as aspirin alone does not have this aggregation inhibiting activity against TCIPA.

Thus the compounds of the invention thereby produce beneficial (i) cardio and chemo protective aspirin effects from the aspirin generated from the prodrug, and a (ii) unexpected additional antiplatelet aggregation effect.

The compounds may be used in patients where an aspirin effect is desirable, for example, cardiovascular patients. However, compounds are therefore surprisingly better inhibitors of platelet aggregation than aspirin alone, and concurrently inhibit tumor cell induced platelet aggregation (TCIPA).

Since the compounds are capable of inhibiting tumor cell induced platelet aggregation (TCIPA) they may be used in the prevention of cancer metastasis (active cancer tumours) in which TCIPA is implicated. Aspirin alone does not have this activity against tumor cell induced platelet aggregation (TCIPA). The compounds may be particularly useful in the subset of population having cardiovascular diseases that have aspirin resistance (due to the additional antiplatelet effect produced, in addition to the aspirin like effect). Another relevant patient group are those of the population having cardiovascular diseases in conjunction with cancer metastasis, or indeed the subset of the patent group with cardiovascular disease whom are at risk of cancer, for example, breast, colon cancer, etc. The compounds may be used in the general population to treat cancer metastasis in cancer patients. Suitably the use includes use of the compound having general structural formula (I) in a patient group having reduced plasma esterase activity and/or use in a patient group having reduced plasma esterase activity and cancer metastasis involving TCIPA.

In a preferred embodiment, there is provided at least one compound as described above, for use in the treatment or prevention of cancer metastasis involving tumor cell induced platelet aggregation (TCIPA). It will be appreciated that at least one of these compounds may be used in a method of treatment and/or prevention of cancer metastasis involving tumor cell induced platelet aggregation (TCIPA), the method comprising the step of administering a therapeutically effective amount of at least one of the above compounds to a patient in need thereof.

Preferably, the at least one compound as described above may be used in the treatment or prevention of a cardiovascular disease (CVD) in conjunction with the treatment or prevention of cancer metastasis involving tumor cell induced platelet aggregation (TCIPA). Therefore, It will be appreciated that at least one compound described above can be used in a method of treatment and/or prevention of CVD in conjunction with the treatment or prevention of cancer metastasis involving tumor cell induced platelet aggregation (TCIPA) comprising the step of administering a therapeutically effective amount of at least one of the above compounds to a patient in need thereof.

Furthermore, at least one of the above compounds described above may be used in the in manufacture of a medicament for the treatment and/or prevention of cancer metastasis involving tumor cell induced platelet aggregation (TCIPA) and/or in manufacture of a medicament for the treatment and/or prevention of cardiovascular disease (CVD) in conjunction with the treatment or prevention of cancer metastasis involving tumor cell induced platelet aggregation (TCIPA).

The at least one compound of the invention may be used to release aspirin, nicotinic acid and a further compound having general structure (II)

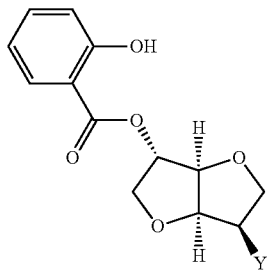

(II)

wherein Y is an arylester or a $C_1$-$C_8$ alkylaryl ester, selected from the group consisting of: benzene, toluene, xylene, benzoic acid, benzoate, nicotinate, isonicotinate and halobenzene, which can be unsubstituted or substituted with
at least one nitric oxide releasing group; and/or
at least one of hydroxide, —Cl, —Br, a $C_1$-$C_8$ alkyl, benzyl, a $C_1$-$C_8$ alkoxy,
benzyloxy, —NHC(O)R, —NH$_2$, —NO$_2$, —ONO$_2$, —(CH$_2$)$_n$ONO$_2$, —OC(O)[(CH$_2$)$_m$]$_{cyclic}$ONO$_2$, —OCOArONO$_2$, —OCOAr(CH$_2$)$_n$ONO$_2$ or a $C_1$-$C_5$ haloalkyl ester, wherein R is a $C_1$-$C_8$ alkyl or a $C_1$-$C_8$ alkoxy group, n=1-8 and m=3-10, to produce an aspirin like effect.

Preferably, the nitric oxide release group of the at least one compound and further compound described above s a nitrate ester, a $C_1$ to $C_8$ alkyl nitrate ester, a $C_3$-$C_{10}$ cycloalkyl nitrate ester or a $C_1$-$C_8$ alkyl nitrate ester. Suitably, the group may be selected from the group consisting of: —NO$_2$, —ONO$_2$, —(CH$_2$)$_n$ONO$_2$, —OC(O) [(CH$_2$)$_m$]$_{cyclic}$ONO$_2$, —OCOArONO$_2$ and —OCOAr (CH$_2$)$_n$ONO$_2$, wherein n=1-8 and m=3-10.

Preferably, the arylester or the alkylaryl ester is substituted at the 2- or 3-position of the aryl ring. Suitable, the aryl ring is substituted with a hydroxide, —Cl, —Br, a $C_1$-$C_8$ alkyl, benzyl, a $C_1$-$C_8$ alkoxy, benzyloxy, —NHC(O)R, —NH$_2$, —NO$_2$, —ONO$_2$, —(CH$_2$)$_n$ONO$_2$, —OC(O) [(CH$_2$)$_m$]$_{cyclic}$ONO$_2$, —OCOArONO$_2$, —OCOAr (CH$_2$)$_n$ONO$_2$ or a $C_1$-$C_5$ haloalkyl ester, wherein R is a $C_1$-$C_8$ alkyl or a $C_1$-$C_8$ alkoxy group, n=1-8 and m=3-10. Desirably, the compound comprises an aryl ester or alkyl aryl ester substituted at the 2- or 3-position of the aryl ring with —NO$_2$, —ONO$_2$, —(CH$_2$)$_n$ONO$_2$, —OC(O) [(CH$_2$)$_m$]$_{cyclic}$ONO$_2$, —OCOArONO$_2$, —OCOAr(CH$_2$)$_n$ ONO$_2$, wherein n=1-8 and m=3-10. More desirably still, the compound comprises an aryl ester substituted at the 2- or 3-position of the aryl ring with —NO$_2$, —ONO$_2$, —(CH$_2$)$_n$ONO$_2$, wherein n=1-4. Preferably, the aryl ester is substituted at the 2-position of the aryl ring with —NO$_2$, —ONO$_2$, —(CH$_2$)$_n$ONO$_2$, wherein n=1 or 2. More desirably still, n=2.

Suitably, the group Y comprises an $C_1$-$C_8$ alkylaryl ester, which may be any one of a methylaryl ester, ethylaryl ester, propylaryl ester, butylaryl ester, pentylaryl ester or a hexylaryl ester.

Preferably, the $C_1$-$C_8$ alkylaryl ester is methyl arylester or ethyl arylester.

Preferably, the aryl group is any one of benzene, toluene, xylene, benzoic acid, benzoate, nicotinate and halobenzene. Particularly preferred are substituted benzoate and nicotinate based aryl esters, wherein the substitutions are described herein. Most preferably, Y comprises an aryl ester selected from benzoate or nicotinate. Nicotinate is the most preferred aryl ester.

Desirably, the Y group may be selected from the group consisting of:

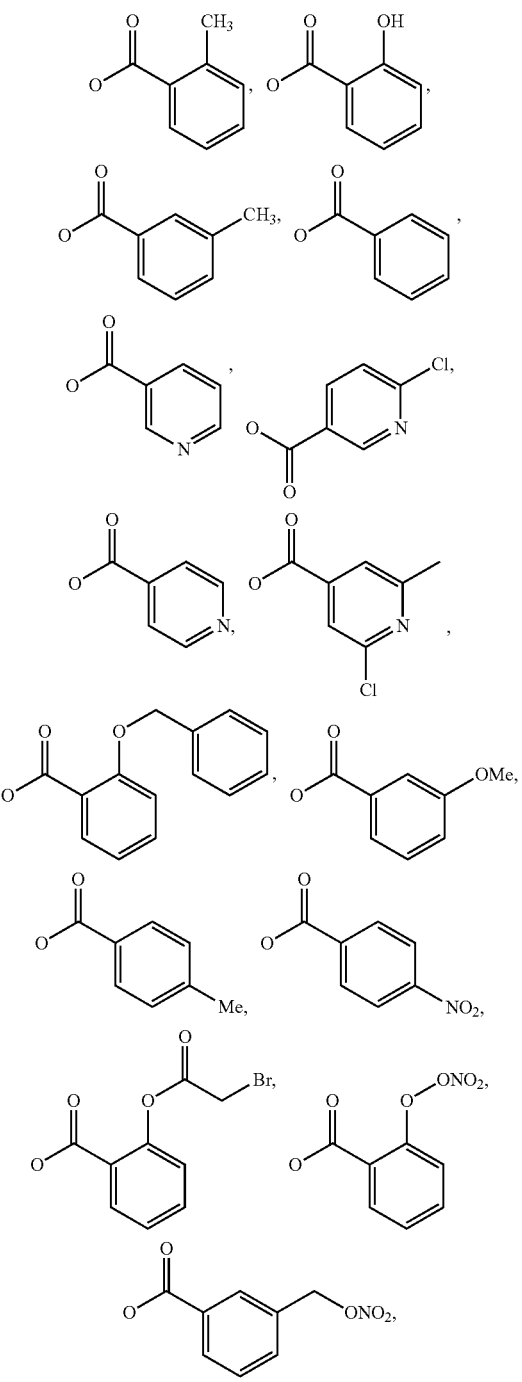

-continued

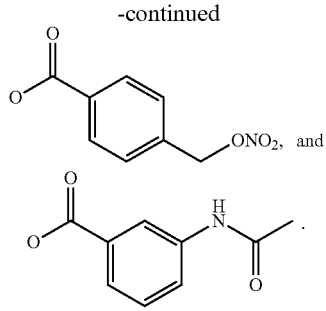

It is particularly preferred that Y is nicotinate, since the nicotinate ester prodrug also produce nicotinic acid (niacin) in addition to aspirin. Isonicotinate is another option of use.

More desirably still, the invention relates to the use of a compound as described herein, wherein the compound is selected from the group consisting of:

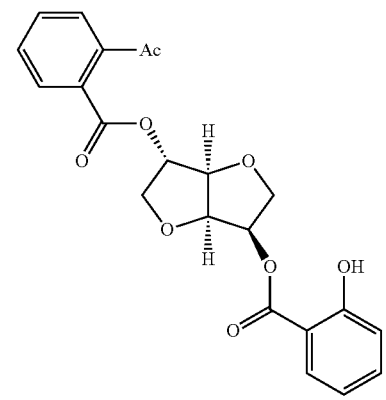

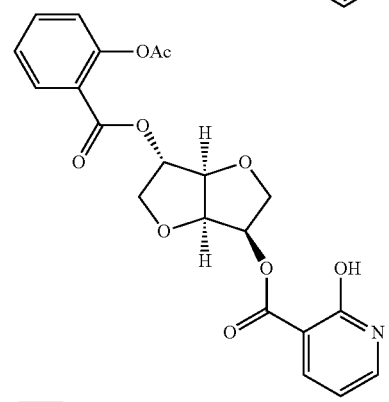

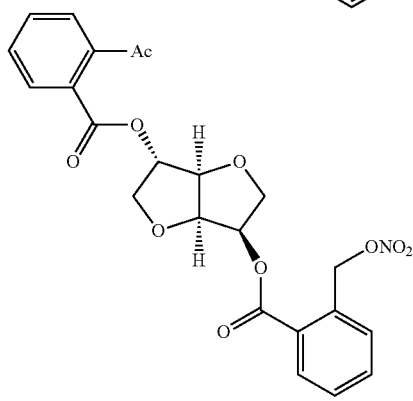

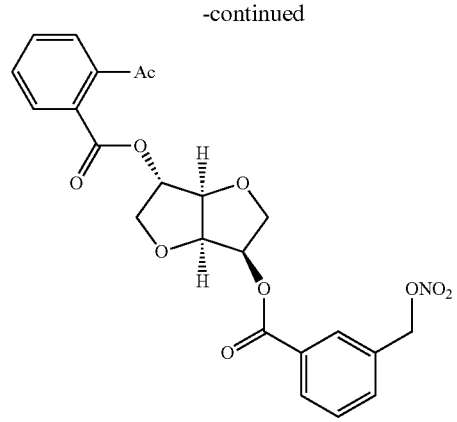

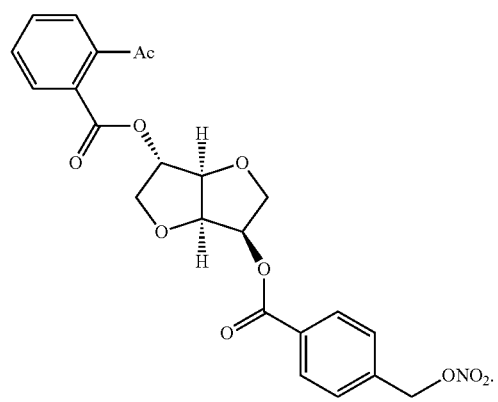

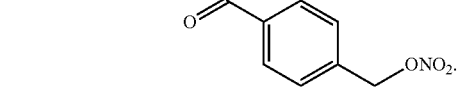

These compounds have been shown to inhibit TCIPA in the cell tests described herein. These compounds also release aspirin. In a particularly preferred embodiment, the invention relates to the use of a compound as described herein, wherein the compound selected from the group consisting of:

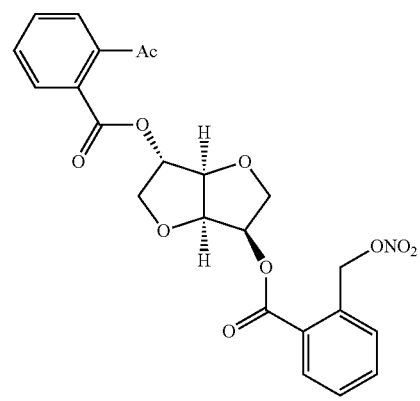

-continued

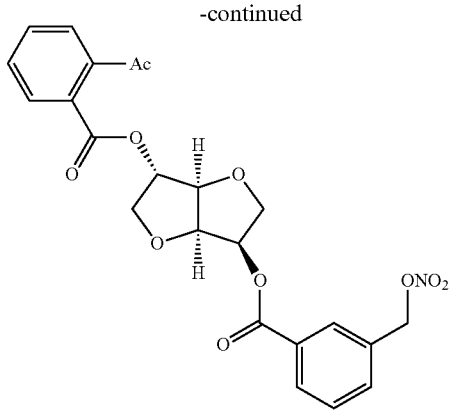

and

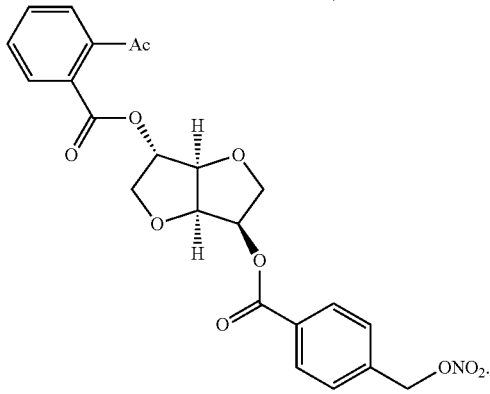

In addition to aspirin release and additional antiplatelet effects produced, these compounds also release beneficial organic nitrates which release NO. NO protects the GI tract. This is desirable, since nitric oxide together with aspirin causes vasodilation and further inhibits platelet aggregation and monocyte adhesion. In other words, NO and aspirin function beneficially together. Thus these compounds are particularly protective towards the gastrointestinal tract. NO is gastroprotective through multiple mechanisms: by promoting blood flow, removing toxins, and stimulating mucus secretion and angiogenesis. Furthermore, nitric oxide is also a potent vasodilator and it inhibits platelet and monocyte adhesion and platelet aggregation.

In a preferred embodiment, the compound:

(compound ST0702)

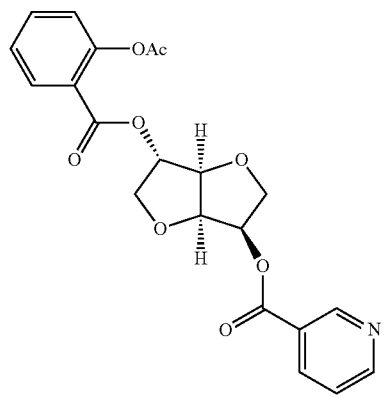

may be used in the methods/uses described herein.

In addition to aspirin release and additional antiplatelet aggregation effect produced, compound (ST0702) generates nicotinic acid. Advantageously, nicotinic acid increases high density lipoprotein cholesterol (HDL) and reduces low density lipoprotein cholesterol and triglycerides. The additional antiplatelet effect arising from this compound means this compound inhibits TCIPA, whereas aspirin itself does not.

In a related aspect of the invention, the invention contemplates a compound to concurrently produce an aspirin effect and an additional antiplatelet effect, the effects together termed a super-aspirin effect, for use in the inhibition of cancer cell metastasis tumor cell induced platelet aggregation (TCIPA), wherein the compound is (ST0702)

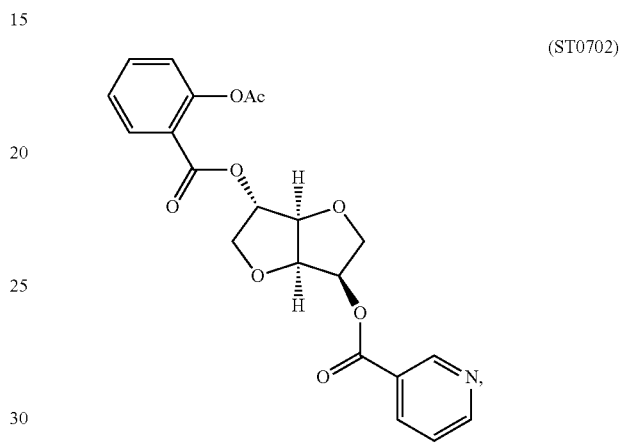

and wherein the compound may be metabolised to aspirin, nicotinic acid and a further compound (metabolite) having structure:

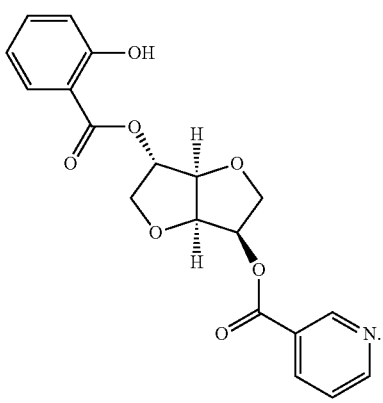 [SMILES: O=C(O[C@@H]1CO[C@H]2[C@@H]1OC[C@@H]2OC(=O)c1ccccc1O)c1cccnc1]

The compound ST0702 produces a super-aspirin effect as described above. The further compound (metabolite) produced may be used itself directly in the treatment and/or prevention of cancer metastasis involving TCIPA and/or can be used in the treatment and/or prevention of CVD in conjunction with cancer metastasis, where TCIPA is involved.

Importantly, it will be appreciated that the compounds and their uses described herein produce/involve an additional antiplatelet effect over an antiplatelet effect caused by aspirin release from the prodrug. This produces the so-called "super-aspirin" effect, that is, by concurrently producing an aspirin effect (from aspirin release from aspirin prodrug and an additional antiplatelet effect over an above that of the aspirin release). The advantaging being that the effects together are suitable for the inhibition of cancer cell metastasis tumor cell induced platelet aggregation (TCIPA). This is particularly true in cardiovascular patients and/or cardiovascular patients who are show aspirin resistance. The additional antiplatelet effect produced inhibits TCIPA.

This compound is desirable as it functions as a cancer preventative agent, with a dual effect through aspirin release and inhibition of TCIPA. It also benefits cardiovascular disease patients through aspirin and, nicotinic acid release. It will particularly benefit subset of the population having CVD and active cancer metastasis.

In a related aspect there is provided a compound having general structure (II), and pharmaceutically acceptable salt and/or hydrates thereof,

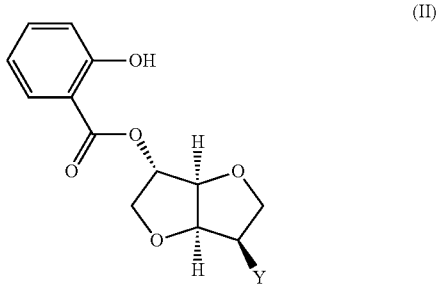
(II)

wherein Y is an arylester or an $C_1$-$C_8$ alkylaryl ester, selected from the group consisting of: benzene, toluene, xylene, benzoic acid, benzoate, nicotinate, isonicotinate and halobenzene, which can be unsubstituted or substituted with
at least one nitric oxide releasing group; and/or
at least one of —Cl, —Br, a $C_1$-$C_8$ alkyl, benzyl, a $C_1$-$C_8$ alkoxy,
benzyloxy, —NHC(O)R, —NH$_2$, —NO$_2$, —ONO$_2$, —(CH$_2$)$_n$ONO$_2$, —OC(O)[(CH$_2$)$_m$]$_{cyclic}$ONO$_2$, —OCOArONO$_2$, —OCOAr(CH$_2$)$_n$ONO$_2$ or a $C_1$-$C_5$ haloalkyl ester, wherein R is a $C_1$-$C_8$ alkyl or a $C_1$-$C_8$ alkoxy group, n=1-8 and m=3-10.

Preferably, the arylester is not salicylate. The preferred groups and substituents are described above. This compound is typically a metabolite of the compound general structure (I) described herein.

Most preferred is a compound having structure (III):

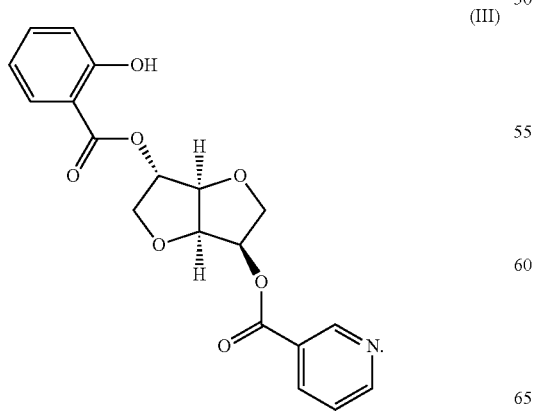
(III)

This compound has been found to be a particularly good inhibitor of tumor cell induced platelet aggregation (TCIPA). Compound (III), isosorbide-2-salicylate-2-nicotinate, is a hydrolysis product of compound (II), isosorbide-2-aspirinate-2-nicotinate.

Further preferred is the use as described herein, wherein the compound having the general structure (I) is

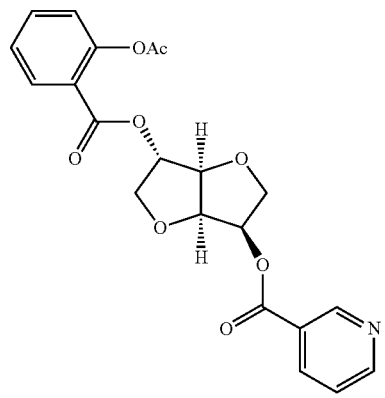 [SMILES: CC(=O)Oc1ccccc1C(=O)O[C@H]1CO[C@H]2[C@@H]1OC[C@H]2OC(=O)c1cccnc1]

and the further compound having general structure (II) is

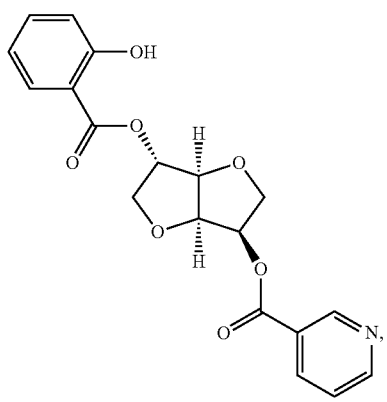 [SMILES: O=C(O[C@@H]1CO[C@H]2[C@@H]1OC[C@@H]2OC(=O)c1ccccc1O)c1cccnc1]

Compound ST0702 concurrently produce an aspirin like effect and inhibit cancer cell metastasis through the inhibition of tumor cell induced platelet aggregation (TCIPA). Compounds

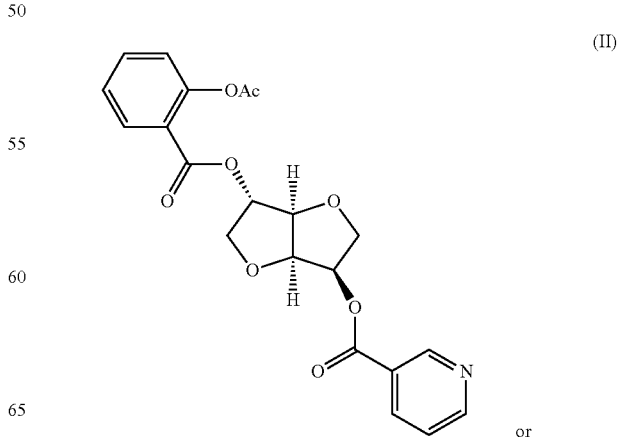
(II)

or

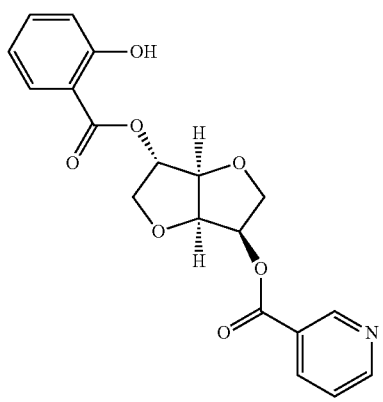

(III)

are preferred compound for use in the treatment of or the prevention of a cancer metastasis involving tumor cell induced platelet aggregation (TCIPA). Suitably, the compounds may be used in the prevention/treatment of CVD in conjunction with cancer metastasis involving TCIPA. In a related aspect, there is provided the compound isosorbide-2-aspirinate-5-nicotinate (ST0702) or isosorbide-2-salicylate-2-nicotinate for use in the manufacture of a medicament for the treatment of cardiovascular disease wherein tumor cell induced platelet aggregation (TCIPA) is a factor. Isosorbide-2-aspirinate-5-nicotinate (ST0702) is also suitable for use as a medicament in conditions requiring inhibition of P-selectin expression. Advantageously, isosorbide-2-aspirinate-5-nicotinate (ST0702) inhibits P-selectin expression, whereas aspirin does not.

Thus either compound (II) or (III) (or mixtures thereof) can be advantageously used in the treatment of cancer metastasis by inhibition of tumor cell induced platelet aggregation (TCIPA). Suitably, either compound (II) or (III) (or mixtures thereof) can be used in the manufacture of a medicament for the treatment of cancer metastasis involving tumor cell induced platelet aggregation (TCIPA). Thus, the compound having structural formula (II) or structural formula (III) may be used as a platelet modulation drug for use in the treatment of or the prevention of a disease involving cancer metastasis mediated by tumor cell induced platelet aggregation (TCIPA). Such uses are particularly beneficial in patients having CVD due to the aspirin and nicotinate released in additional to the additional antiplatelet aggregation effect.

Compound (II), isosorbide-2-aspirinate-5-nicotinate (ST0702) is particularly useful for the treatment of and/or the prevention of cardiovascular disease in conjunction with tumor cell induced platelet aggregation (TCIPA) and/or in the in the prevention/treatment of CVD in conjunction with cancer metastasis involving TCIPA. This is because isosorbide-2-aspirinate-5-nicotinate (ST0702) advantageously functions as a prodrug and releases three active metabolites, namely, aspirin, nicotinic acid and isosorbide-2-salicylate-2-nicotinate. In fact, isosorbide-2-salicylate-2-nicotinate is the principal metabolite of isosorbide-2-aspirinate-5-nicotinate in human plasma. Each of these actives has a useful role in cardiovascular diseases wherein tumor cell induced platelet aggregation (TCIPA) is a factor as aspirin, nicotinic acid are cardioprotective and isosorbide-2-salicylate-2-nicotinate is chemo-preventative through its utility against cancer metastasis by inhibiting tumor cell induced platelet aggregation (TCIPA). In fact, prodrug isosorbide-2-aspirinate-5-nicotinate is a surprisingly more potent inhibitor of ADP and collagen-induced platelet aggregation than aspirin, is capable of releasing nicotinic acid and most surprisingly is capable of concurrently inhibiting tumor cell induced platelet aggregation (TCIPA), whereas aspirin itself cannot. The unexpectedly good activity of isosorbide-2-aspirinate-5-nicotinate in inhibiting tumor cell induced platelet aggregation (TCIPA) was surprising in view of the fact that is known that aspirin lacks efficacy in inhibition of tumor cell induced platelet aggregation (TCIPA). Suitably, the cardiovascular disease contemplated herein includes ACS, stroke or peripheral artery thromoembolism. The Inventors have show that aspirin release from the prodrug is not important for platelet inhibitory actions of isosorbide-2-aspirinate-5-nicotinate in tumor cell induced platelet aggregation (TCIPA). Suitably, the cancer metastasis mediated by tumor cell induced platelet aggregation (TCIPA) is associated with malignant mesothelioma, gynaecological malignancies, lung, renal, gastric, ovarian, colon, colorectal, breast tumors or other solid tumor types. Suitably, the TCIPA is associated with cancer cells, colon cancer cells or ovarian cancer cells. In particular, cancer metastasis mediated by tumor cell induced platelet aggregation (TCIPA) may be in HT1080 cancer calls, CACA-2 colon cancer cells or 59M ovarian cancer cells. The CVD is may be, for example, coronary heart disease, cardiomyopathy, cardiovascular disease, ischaemic heart disease, heart failure, hypertensive heart disease, inflammatory heart disease, valvular heart disease, myocardial Infarction or other associated conditions caused by these CVD types.

The compound isosorbide-2-aspirinate-5-nicotinate (II) or isosorbide-2-salicylate-2-nicotinate (III) may be used in a screening method identify other TCIPA activity agents. Isosorbide-2-aspirinate-5-nicotinate (II) or isosorbide-2-salicylate-2-nicotinate (III) may be used in in-vitro platelet aggregation models using plasma rich platelets and/or washed plasma or tumor cell-platelet engagement.

BRIEF DESCRIPTION OF THE DRAWINGS

Additional features and advantages of the present invention are described in, and will be apparent from, the detailed description of the invention and from the drawings in which:

FIG. 1B illustrates the time course of impact of, ISANA (ST0702) in micronized and non-micronised forms and Aspirin on TxB2 levels measured on the Y axis as a percentage of baseline based on a mean of n=3 per group. At 24 hours, there was no statistical or clinical differences observed between Group C and D. Statistical differences between Groups C/D and either A or B were observe at 24 hours.

FIG. 2A illustrates structural formulae of a number of aspirin prodrug test compounds (ST0702-04);

FIG. 2B shows the metabolic routes of ST0701 in human plasma BuChE solution generating aspirin and salicylate ester compounds. ST0701 is largely hydrolysed along the productive pathway making it a highly effective aspirin prodrug. Aspirin esters are in general hydrolysed along the salicylate pathways;

FIG. 3B shows concentration response curves for inhibition of collagen (5 µg/ml) induced aggregation in WP;

FIGS. 4A-4C illustrate inhibition of platelet aggregation in PRP stimulated by adenosine diphosphate ADP (10 µM). The nitrate compounds ST0703, ST0704 were significantly more potent than aspirin under these conditions. ST0701 (data not shown) and ST0702 were similar in effect on ADP induced aggregation and more efficacious than aspirin across the test concentration range. FIG. 4A. Concentration response curves for inhibition of ADP (10 µM) induced aggregation (n=6). The nitrate compounds ST0703, ST0704 were significantly more effective inhibitors than aspirin under these conditions. FIG. 4B shows % inhibition of aggregation induced by ADP (10 µM) at 100 µM—Effect of prodrugs and aspirin incubated at 100 mM on ADP-induced aggregation. FIG. 4C shows effect of ODQ pretreatment on inhibitory effects of aspirin and the prodrug test compounds in PRP stimulated with ADP (10 µM), n=4, **p<0.05—Inhibition of ADP-induced aggregation by aspirin and aspirin prodrugs (100 µM) with or without ODQ (10 µM) Asp, aspirin; ODQ, 1H-[1,2,4]oxadiazolo[4,3-a]quinoxalin-1-one.

(FIG. 5A) Result of experiments in washed platelets (WP). (FIG. 5B) Results of experiments in platelet-rich plasma (PRP).

(FIG. 9A) Representative aggregometer traces showing TCIPA (representative of 4 experiments). TCIPA was induced by HT1080 cells ($2\times10^5$/ml), CaCo2 cells ($1.5\times10^3$/ml) and 59M cells ($1\times10^3$/ml). (FIG. 9B) Representative phase-contrast microscopy of 59M-induced TCIPA.

FIGS. 11A-11G illustrate phase-contrast microscopy of TCIPA in the presence of aspirin prodrugs. Phase contrast microscopy of un-aggregated platelets (FIG. 11A), TCIPA induced by 59M at 50% of aggregation with the presence of big platelet aggregates in the absence (FIG. 11B) or presence of aspirin (FIG. 11C), ISAS (FIG. 11D) ST0702 (FIG. 11E), orthonitrate (FIG. 11F) and metanitrate (FIG. 11G) with less formation of big aggregates. Scale bar, 20 µM.

FIGS. 12A-12B illustrate Zymogrphy of releasates of 59M and platelets in the presence of aspirin prodrugs. Representative zymography (FIG. 12A) and the statistical analysis (FIG. 12B) showing the effects of aspirin, ST0702, ISAS, orthonitrate and metanitrate (500 µM) on the release of MMP-2 during TCIPA. TCIPA was induced by 59M cells ($1\times10^3$/ml). Aggregated platelets with tumour cells in the absence of inhibitors were used as controls. Bars are mean±s.e.mean from four separate experiments. P>0.05 vs TCIPA;

FIGS. 13A-13B illustrate flow-cytometry analysis of P-selectin on platelets during TCIPA in the presence of different inhibitors. FIG. 13A) Representative graphs of resting platelets (resting), TCIPA and the effects of Aspirin and ST0702; FIG. 13B) Statistical analysis showing the effects of Aspirin, ST0702, ISAS, orthonitrate and metanitrate (500 µM) on TCIPA. TCIPA was induced by 59M cells (1×103/ml). Aggregated platelets with tumour cells in the absence of inhibitors (TCIPA) and resting platelets were used as controls. Bars are mean±s.e.mean from four separate experiments. ***P<0.01, TCIPA versus resting; #P<0.05, ###P<0.01, treatments versus TCIPA.

FIGS. 14A-14D illustrate the effect of aspirin prodrugs on TCIPA under flow conditions. Microsocpy of 59M cell cluster in the trap (FIG. 14A), platelet encapsulation of the tumour cell aggregate (FIG. 14B) and platelet activation (black arrows) which resulted in platelet-cancer aggregate disruption (white arrows) (FIG. 14C). The effects of Aspirin (ASA), Nicotinate, ISAS, ISMNA, ortho and meta (500 µM) on platelet-tumour cell disruption were evaluated (FIG. 14D). Aggregated platelets with tumour cells in the absence of inhibitors (TCIPA) were used as negative controls. Bars are mean±s.e.mean from four separate experiments. *P<0.05, treatments versus TCIPA;

FIGS. 16A-16E show effect of ST0702 on TCIPA and platelet aggregation. FIG. 16A) Statistical analysis showing the effects of ST0702 and its metabolite ST0702 salicylate (500 µM) on TCIPA under static conditions. TCIPA was induced by HT1080 cells (2×105/ml) and CaCo2 cells ($1.5\times10^3$/ml). Aggregated platelets with tumour cells in the absence of inhibitors (TCIPA) were used as controls.

*P<0.05; treatments versus TCIPA. FIG. 16B) Statistical analysis showing the effects of ST0702 and ST0702 salicylate on collagen-induced platelet aggregation. Aggregated platelets with collagen (2 µg/ml) were used as control. *P<0.001; treatments versus control. FIG. 16C) Effects of ST0702 salicylate on ADP-induced platelet aggregation. Aggregated platelets with ADP (10 µg/ml) were used as controls. Both control and ST0702 salicylate treated samples were incubated in the presence and absence of eserine (10 µM). P<0.01; treatments versus control. FIG. 16D) The effects of ST0702 salicylate (500 µM) on platelet-tumour cell disruption were evaluated. Aggregated platelets with tumour cells in the absence of the inhibitor (TCIPA) were used as negative controls.

Figure 1A:
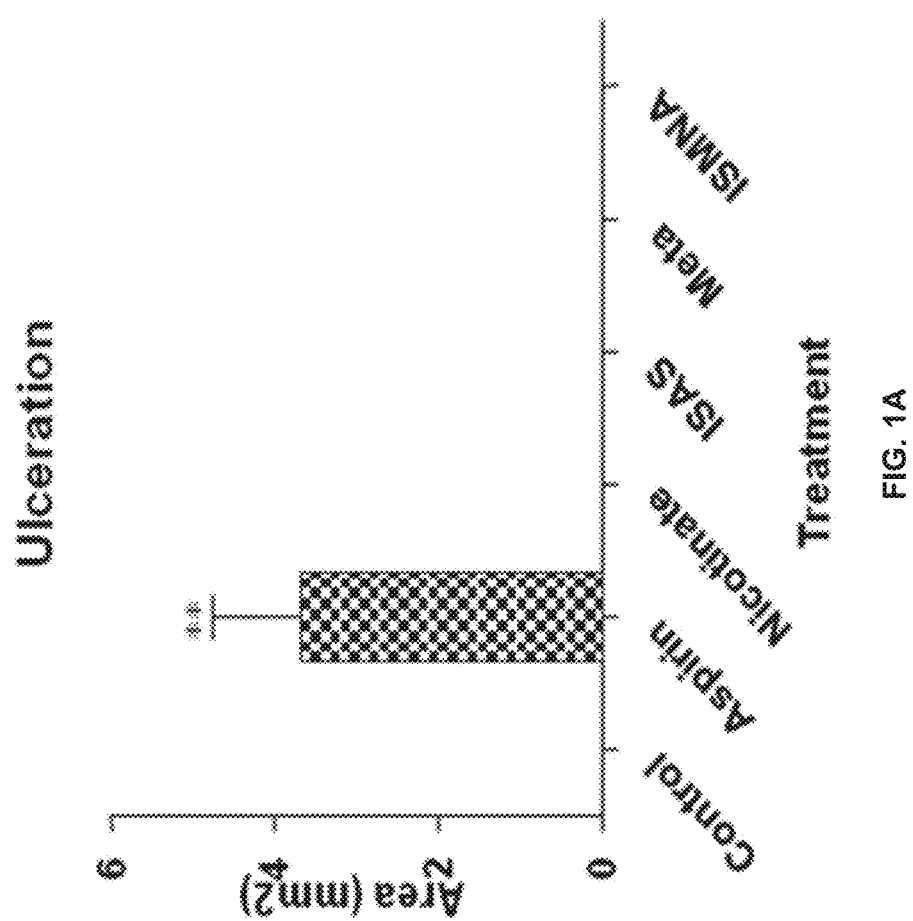
FIG. 1A illustrates the ulcerogenic effects of aspirin 30 mg/Kg daily (oral gavage) for 3 days and molar dose equivalents of ISANA (ST0702—"Nicotinate"), ISAS (ST0701), ISANO ("Meta) and ISMNA (n=3 per group) (FIGS. 2A-2B).

Table 1 shows $IC_{50}$ values for the inhibition of platelet aggregation WP and PRP (platelet rich plasma) in response to collagen (5 mg/ml). Also shown is a % aspirin release from each of the test compounds in human plasma.

| Compound | $IC_{50}$ in WP (PRP, 95% CI) | % Aspirin release[†] |
|---|---|---|
| Aspirin | 34 (92, 85-100[†]) µM | 100 |
| ST0701 | 200 (21, 17.2-23.9[†]) µM | 70-85 |
| ST0702 | 154 (85, 76-93) µM | 30-45 |
| ST0703 | >500 (17, 8.8-26.4[†]) µM | 60-65 |
| ST0704 | >500 (90, 79.5-100.1[†]) µM | 30-40 |
| ST0705 | >500 (>300) µM | <5 |

[†]From Reference 7; IC50, concentration estimated to cause 50% inhibition of platelet aggregation.

DETAILED DESCRIPTION OF THE INVENTION

The present inventors have demonstrated that the compounds used within the context of the present address aspirin resistance problems in 3 major ways:
(i) the prodrug compounds used herein demonstrates significantly better GI tolerability when compared to aspirin;
(ii) in the case of ST0702 (ISANA or the "Nicotinate"), data obtained in a Non-Human Primate study indicate that there are surprisingly good effects of the drug in-vivo; and
(iii) in the case of the prodrugs used within the context of the present invention, and exemplified by the data on the nicotinate compound ST0702, there are advantageous and desirable non-aspirin antiplatelet effects produced by a metabolite of the prodrug compounds.

It has been found that because platelets are activated by multiple pathways, these non-aspirin antiplatelet effects supplement the aspirin effects to reduce platelet activation, particularly in disease states with high levels of inflammation or in patients with genetic polymorphisms that render them aspirin resistant. Each of these beneficial mechanisms of dealing with the clinical problem of aspirin resistance are described in the following studies outlined below.

Furthermore, the present inventors report on a pharmacological investigation into the platelet inhibitory properties of isosorbide-based aspirin prodrugs (for example, compounds ST0701-05). The study focuses on prodrug activation by plasma and platelet esterases. The following has been examined: the relative potency of the compounds as inhibitors of aggregation in PRP and washed platelets (where BuChE is absent), the involvement of platelet receptors, the effect of BuChE and other esterase inhibitors on potency and efficacy, the relative roles of aspirin and nitric oxide in the effects of compounds ST0703-05, the time course for activation and platelet inhibition, and the role of platelet esterases in aspirin prodrug activation.

Furthermore still, the present inventors have produced compounds that that are potent inhibitors of ADP and collagen-induced platelet aggregation. Two in vitro experimental models for the study of TCIPA (under static and flow conditions) have been established. Using both models, the effect of different aspirin pro-drugs in TCIPA has been studied. ST0702 inhibits TCIPA under both static and flow conditions, and therefore it seems to be an effective platelet-modulating drug for cancer metastasis. ST0702 therefore is a compound showing enhanced aspirin effects or what is termed herein "a super aspirin effect" which means it is a more potent inhibitor of ADP and collagen induced platelet aggregation than would be expected from aspirin release alone and that this additional antiplatelet aggregation effect inhibits TCIPA under both static and flow conditions.

GI Tolerability Testing
In Vivo Study 1

This data demonstrates significantly better GI tolerability of the prodrugs compared to aspirin. Poor GI tolerability is a known major driver of patient non-compliance and aspirin resistance. The precise mechanisms by which aspirin causes mucosal damage have not been fully explained. Although NSAIDs can induce GI damage via both topical and systemic effects, several lines of evidence indicate that the direct irritant effect is the major mechanism leading to ulcers and ulcer complications:

There is not a direct link between COX activity/PG synthesis and gastric injury and PG synthesis can be markedly suppressed without ulcers forming.

COX-1 selective NSAIDs, while inhibiting COX-1 activity, do not cause ulcers.

Although selective COX-2 inhibitors and synthetic PG analogues attenuate NSAID induced GI toxicity, then do not abolish it.

Although parenteral aspirin inhibits COX-1 activity, ulcers only form when aspirin is given orally.

In this study, rats are fed Aspirin 30 mg/Kg daily or molar equivalent doses of ISAS, ISANA ("Nicotinate"), ISANO "Meta" nitrate or ISAMNA in oral gavage daily for 3 days (n=3 per group). At the end of the dosing period, all animals were sacrificed, stomachs removed and were immersed in 2% formalin for at least 10 min to fix the gastric tissue wall, and will opened along the greater curvature for scoring for irritation or hemorrhagic lesions or ulcers developed in the corpus mucosa under a dissecting microscope on a 5-point scale. The percentage of stomach surface area showing ulcers was recorded for each animal and expressed as a percentage.

The results (FIG. 1A) demonstrate that aspirin, as expected, has a significant gastric ulcerogenic effect in this rat model. Conversely, none of the Aspirin Pro-drugs demonstrated ulcerogenic effects and were significantly better than conventional aspirin at equimolar doses.

This means the prodrug compounds may advantageously used in patients with poor GI tolerability for aspirin or patients with sensitive GI conditions aggravated by aspirin.

In Vivo Study 2

In the case of ISANA ("Nicotinate" ST0702), there are surprisingly good effects of the drug in-vivo. These data are obtained in a Non-Human Primate study.

In-vivo data on the gastro-intestinal benefits of the series of aspirin pro-drugs suggest that gastro-protection is a feature shared by all of the pro-drugs and will contribute to the improvement of gastro-intestinal tolerability, compliance with therapy and therefore will help to resolve the cause of aspirin resistance in large proportion of patients.

In earlier in-vitro data, it was demonstrated that ISAS is the most effective aspirin prodrug studied to date, by releasing 85% of the expected amount of aspirin in human plasma. Conversely, ST0702 (ISANA—"Nicotinate") is only a moderately effective aspirin prodrug in the previous in-vitro studies, releasing approximately 40% of the available aspirin (WO 2009/080795). Surprisingly, it has now been found that the relative in-vitro efficacy of ISANA is significantly better than expected.

A series of studies in non-human primates to reflect as closely as possible the in-vivo behaviour of aspirin and its prodrugs in human primates has been carried out. The details of the general methods and animal housing applied to each phase of the study are described later.

In Vivo Phase 2A

The objectives of this study are to determine the comparative clinical efficacy as determined by TxB2 suppression with single oral gavage dose administration of Aspirin, ST0702 and ST0702 Micronised to the cynomolgus monkey. Aspirin pharmacokinetics were compared using Area Under the Curve (AUC) calculations.

Experimental Design

| Test Article (n = 3) | Dose Level (mg/kg) | Dose Volume (mL/kg) | Dose Concentration (mg/mL) |
| --- | --- | --- | --- |
| ST-0702 | 9.6 | 10 | 0.96 |
| ST-0702 Micronised | 9.6 | 10 | 0.55 |
| Aspirin | 4.2 | 10 | 0.42 |

Results demonstrate that in terms of suppression of efficacy, denoted by TxB2 levels as a percentage of baseline, ST0702 and aspirin were effective at 1 and 24 hours post dosing with statistical differences between crystalline non-micronised and miconised ST0702. There was no difference between aspirin and micronized ST0702. The modeled AUC of Aspirin from the Aspirin 4.2 mg/Kg dose was 870 ng·hr/mL. AUCs of equimolar doses of ST0702 were: 249 mg·hr/mL (non-micronised, 31% of aspirin AUC) and 506 ng·hr/mL (micronized, 58% of aspirin AUC). These data demonstrate (i) that plasma TxB2 as a marker of aspirin efficacy is suppressed by ISANA (ST0702);

(ii) that when micronized, ISANA is better absorbed and releases more aspirin;

[3] that when micronized, ISANA provides an aspirin AUC that is 58% of the corresponding aspirin dose in vivo.

[4] the apparent TxB2 suppression activity of micronized ISANA is greater than would be predicted by the aspirin AUC. Taken together, these data suggest that ISANA (ST0702) is a surprisingly good candidate for development as an aspirin prodrug for aspirin-like antiplatelet (additional antiplatelet effect not attributable to aspirin) efficacy.

Phase 2B

The objectives of this study are to determine the comparative pharmacokinetics of ST0702 at 9.6 and 4.8 mg/Kg with single oral gavage dose administration to the cynomolgus monkey and to determine dose-response effects.

Experimental Design

| Test Article | Dose Level (mg/kg) | Dose Volume (mL/kg) | Dose Concentration (mg/mL) |
| --- | --- | --- | --- |
| Micronized ST-0702 | 4.8 | 10 | 0.48 |
| Micronized ST-0702 | 9.6 | 10 | 0.96 |
| Aspirin | 2.1 | 10 | 0.21 |

Figure 1C:
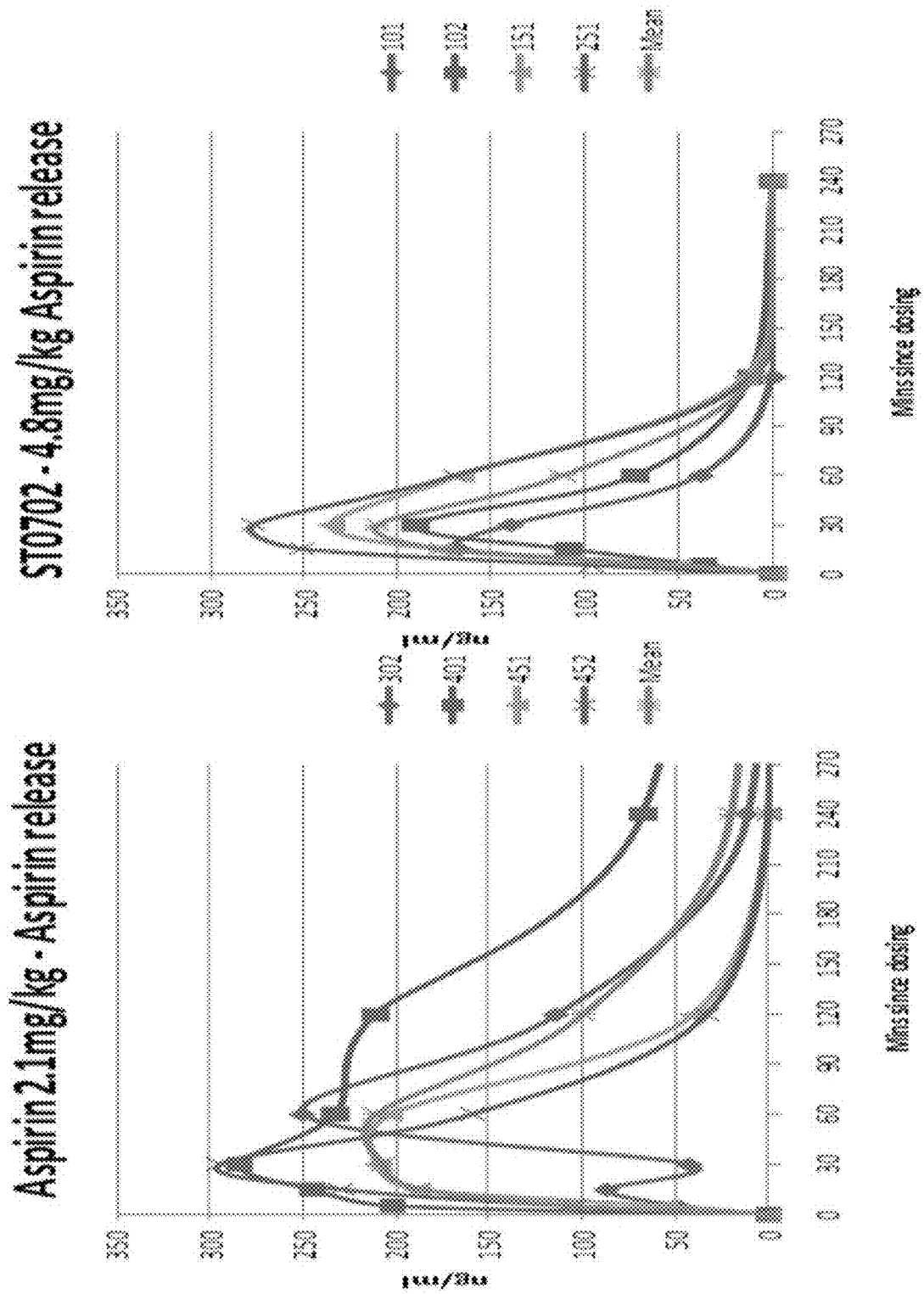
FIG. 1C illustrates comparative aspirin pharmacokinetic profiles of Micronised ST0702 4.8 and 9.6 mg/Kg (n=4 per group). Aspirin 2.1 mg/Kg is included with similar concentration range for comparative purposes.
Figure 1C:
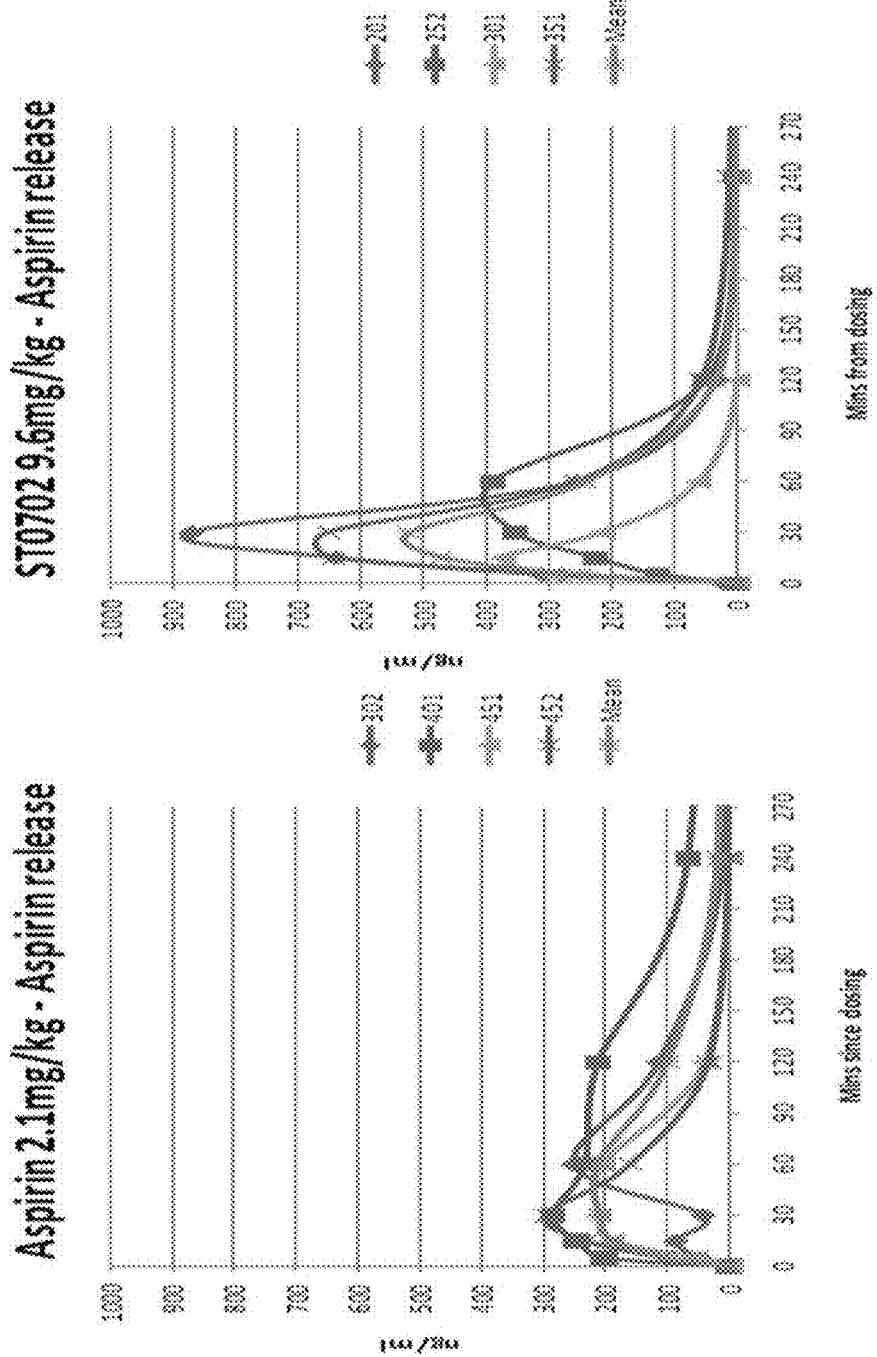

Results demonstrate that in terms of aspirin release, Micronized ST0702 4.8 mg/Kg has a similar Cmax to equimolar doses of aspirin (2.1 mg/Kg, FIG. 1C). Micronised ST0702 9.6 mg/Kg has a twice the Cmax of aspirin (2.1 mg/Kg) and Micronised ST0702 4.8 mg/Kg. Cmax for ST0702 groups occurred consistently at 30 minutes whereas aspirin absorption continued with a Cmax at 1 hour. TxB2 suppression was 47% complete with Micronized ST0702 4.8 mg/Kg at 24 hours compared to the 70% complete with 9.6 mg/Kg. Pharmacokinetic data for ST0702 4.8 mg/Kg: Cmax 211 ng/mL, Tmax 0.5 hr, AUC 221 ng·hr/mL. Corresponding data for ST0702 9.6 mg/Kg: Cmax 522 ng/mL, Tmax 0.5 hr, AUC 571 ng·hr/mL. The modeled AUC of Aspirin from the Aspirin 4.2 mg/Kg dose was 923 ng·hr/mL. AUCs of equimolar doses of Micronised ST0702 was 571 ng·hr/mL (62% of aspirin AUC). Together with data from Study 2A, these data suggest that Micronised ST0702 delivers 58-62% of the expected aspirin in-vivo, compared to approximately 40% in-vitro.

These data demonstrate that dose-response effects of Micronized ST0702 are linear and predictable. Accordingly it should be possible to achieve desired aspirin-like effects and TxB2 suppression with careful dose selection of ST0702.

Study 3

In the case of the prodrugs, and exemplified by the data on ST0702 (ISANA—"Nicotinate"), there are non-aspirin antiplatelet effects of a metabolite. Because platelets are activated by multiple pathways, these non-aspirin antiplatelet effects are thought to supplement the aspirin effects to reduce platelet activation, particularly in disease states with high levels of inflammation or in patients with genetic polymorphisms that render them aspirin resistant. ISANA ("Nicotinate", ST0702) demonstrates an unusual property of greater inhibition of Tumour Cell Induce Platelet Aggregation (TCIPA) compared to aspirin and compared to other prodrugs. These demonstrate non-aspirin antiplatelet effects (discussed in greater detail below). Similar data have been obtained using the breakdown metabolite of ST0702, Isosorbide 2 salicylate 5 nicotinate, suggesting that the antiplatelet effects of ST0702 in response to TCIPA may arise from an identified metabolite.

Figure 1D:
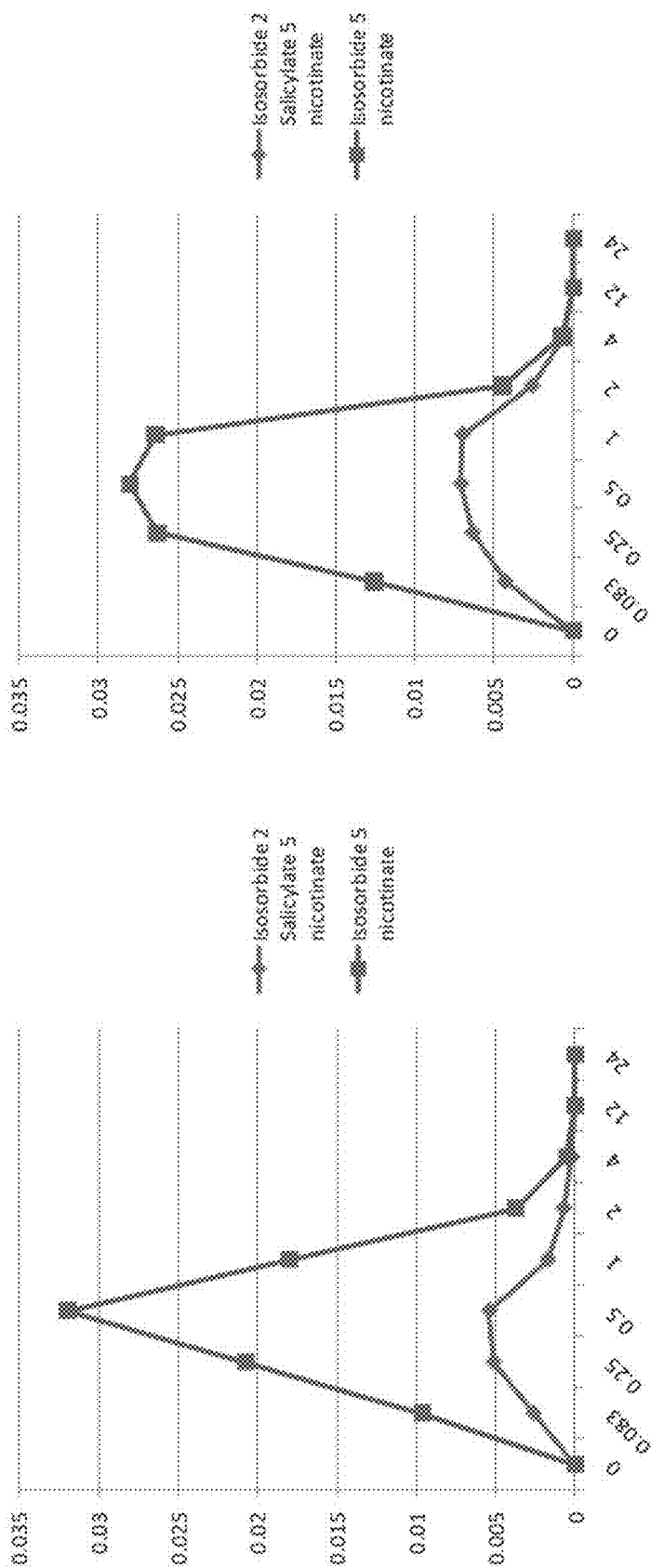
FIG. 1D illustrates comparative pharmacokinetic profiles of Isosorbide 2 salicylate 5 nicotinate and isosorbide 5 nicotinate from Cynomologus Monkeys dosed with Micronised ST0702 4.8 and 9.6 mg/Kg (n=4 per group).

Although the half life of the Isosorbide 2 salicylate 5 nicotinate metabolite is very short in-vitro, we investigated the serum taken from Cynomologus Monkeys participating in Study 2B above. The comparative pharmacokinetics of Isosorbide 2 salicylate 5 nicotinate from Monkeys receiving a single oral gavage dose of micronized ST0702 at 9.6 and 4.8 mg/Kg were evaluated. The concentrations of the breakdown products of ISANA were quantified using LCMS methods. These data are presented in FIG. 1D and demonstrate that there are detectable levels of the two metabolites in plasma up until 2 hours post dosing.

Cynomologus Monkey Study—Methods
Test Population
Species/grade: Monkey
Strain: Cynomolgus
Country of Origin: China
Supplier: Guangxi Weimei Bio-tech Co., LTD
 25 Jinzhou Road, Nanning, Guangxi
 China 530021
Quarantine Facility: Charles River Laboratories Greater China
 Preclinical Services Shanghai (PCS-SHG)
 998 Halei Road, Building 3
 Shanghai
 China 201203
Number of Males: 6
Number of Females: 6
Target age at the Initiation of Dosing: 2.0 to 4.0 years
Target Weight at the Initiation of Dosing: 3.8 to 5 kg
Each animal is uniquely identified by a permanent skin tattoo.
Environmental Acclimation Animals are transferred from PCS-SHG in-house colony. A minimum acclimation period of one week is allowed between transfer and the start of treatment in order to accustom the animals to the laboratory environment.
Selection, Assignment, and Replacement of Animals Before dosing initiation, all animals are weighed and assigned to treatment groups using a computerized randomization procedure. Randomization is by stratification using body weight as the parameter. Animals in poor health or at extremes of body weight range are not be assigned to groups. The disposition of all animals are documented in the study records. Spare animals are maintained with the main study population for the duration of the study.
Housing Animals are socially housed (up to 3 animals of same sex and same dosing group together) in stainless steel cages equipped with a stainless steel mesh floor and an automatic watering valve unless deemed inappropriate by the Study Director and/or Clinical Veterinarian. Animals are separated during designated procedures/activities. Each cage is clearly labeled with a color coded cage card indicating study, group, animal and tattoo number, and sex.
Environmental Conditions The targeted conditions for animal room environment are as follows:
Temperature: 20° C. to 26° C.
Humidity: 40% to 70%
Light Cycle: 12 hours light and 12 hours dark (except during designated procedures)

Temperature and humidity are monitored and recorded continuously in each animal room by an environmental monitoring system. In the event of a system failure, manual recording are performed (once daily) as defined in the Standard Operating Procedures. The light cycle interruptions are documented in the study data. A minimum often air changes/hour are maintained.
Food All animals will have access to a standard certified pelleted commercial primate food (Certified PMI 5K9C) twice daily except during designated procedures. Maximum allowable concentrations of contaminants in the diet (e.g., heavy metals, aflatoxin, organophosphate, chlorinated hydrocarbons, PCBs) are controlled and routinely analyzed by the manufacturers. The results of the analysis are retained at PCS-SHG. It is considered that there are no known contaminants in the dietary materials that could interfere with the objectives of the study
Water Municipal tap water which has been softened, purified by reverse osmosis and exposed to ultraviolet light are freely available (except during designated procedures). Periodic analysis of the water is subcontracted to management authorized analytical laboratories which are audited by the QAU of PCS-SHG. The analytical results are retained in the archives of PCS-SHG. It is considered that there are no known contaminants in the water that could interfere with the objectives of the study.
Animal Enrichment Animals are socially housed for psychological/environmental enrichment and are provided with items such as perches, floor toys, foraging devices and/or hanging devices, except during designated activities. Additional enrichment, such as music, natural sounds or color videos films is also provided. Each animal is offered food supplements (such as certified treats, fresh fruit and/or Prima Foraging Crumbles®). Additional enrichment may be provided if deemed appropriate by the Study Director, in consultation with the clinical veterinarian.
Veterinary Care Following transfer, each animal is given a general physical examination by a member of the veterinary staff to assess health status. All animals have previously been tested at least three times for tuberculosis by intradermal injection of tuberculin. As required by SOP, animals are retested approximately every three to four months thereafter following the last injection. Veterinary care is available throughout the course of the study and animals are examined by the veterinary staff as warranted by clinical signs or other changes. All veterinary examinations and recommended therapeutic treatments are documented in the study records. In the event that animals show signs of illness or distress, the responsible veterinarian may make initial recommendations about treatment of the animal(s) and/or alteration of study procedures, which must be approved by the Study Director.
Dosing Animals are acclimated to the oral gavage procedure for at least 3 days prior to the commencement of dose formulation administration. Deionized water is administered by oral gavage using a disposable catheter attached to a plastic syringe at a dose volume of 5 mL/kg. Animals are treated at approximately the same time on each dosing day. Dose formulations are administered by oral gavage using a disposable catheter attached to a plastic syringe. Following each daily dose, the gavage tube is rinsed with 6 mL of Ultra Pure water into the animal's stomach. Each animal will be dosed with a clean gavage tube on each dosing occasion. The dosing volume is 10 mL/kg. Each actual volume administered will be based on the most recent practical body weight of each animal. The dose formulations will be stirred continuously during dose administration.
Samples for Clinical Pathology and Immunochemistry Evaluation Blood is collected from an appropriate vein once pretreatment and during the dosing and recovery phases as specified below. After collection, samples are transferred to the appropriate laboratory for processing. Additional blood samples may be obtained if permissible sampling frequency and blood volume are not exceeded.

Food is removed overnight (minimum 12 hours) from animals before blood sampling (for clinical chemistry and immunochemistry). Samples are collected according to the following table.

Bioanalytical Sample Processing

Samples are mixed gently and placed on crushed wet ice until centrifugation, which are carried out as soon as practical. The samples are centrifuged for approximately 10 minutes in a refrigerated centrifuge (approximately 4° C.) at 2700 rpm. The resultant plasma are separated, transferred to uniquely labeled clear polypropylene tubes, and frozen immediately over dry ice and transferred to a freezer set to maintain −80° C. The plasma samples are transferred to the bioanalytical laboratory at the Testing Facility.

Bioanalytical Sample Analysis

Plasma samples are analyzed for concentration of Aspirin, Salicylic Acid and Nicotinic Acid using a qualified analytical procedure. Analysis are performed by LC MS/MS under Analytical Procedure. Data collection is performed using Analyst from AB Sciex. Statistical analyses including regression analysis and descriptive statistics including arithmetic means and standard deviations, accuracy and precision are performed using Watson Laboratory Information Management System (LIMS) and Microsoft Excel.

Pharmacokinetic Evaluation

Toxicokinetic parameters are estimated using WinNonlin pharmacokinetic software (Pharsight Corp., Mountain View, Calif.). All parameters are generated from individual Aspirin, Salicylic Acid and Nicotinic Acid concentrations in plasma unless otherwise stated. Mean concentrations are derived from where possible. Parameters are estimated using sampling times relative to the start of each dose administration.

Conclusions from Monkey Study

ISANA appears to be more effective (approximately 60% of equivalent aspirin release) in vivo than in vitro (40% of expected release) from an aspirin delivery point of view. There is a dramatic improvement in kinetics and efficacy with simple micronisation of ISANA which bodes remarkably well for formulation given the basic nature of the oral administration of ISANA. TxB2 suppression with micronised ISANA is as effective as equimolar doses of aspirin.

There appears to be a more impressive effect of ISANA on TxB2 suppression (equivalent) than the pharmacokinetic data would suggest (AUCs approximately 60%).

The metabolite of interest is detectable for >2 hours in monkey plasma at both 4.8 and 9.6 mg/Kg which is likely to be significant for the clinically relevance of the metabolite.

Platelet Inhibitory Studies—Material and Methods

Reagents

All reagents were purchased from Sigma-Aldrich (Dublin, Ireland) unless otherwise stated. Collagen and ADP were obtained from Chronolog (Havertown, Pa., U.S.A.). Allophycocyanin (APC)-conjugated monoclonal antibody against high-affinity GPIIb/IIIa (PAC-1-APC) and APC-conjugated monoclonal antibody against human platelet P selectin (CD62P) were purchased from BD Biosciences (Oxford, UK). Human (monoclonal, polyclonal) anti-CES 1 and CES 2 antibodies were purchased from Sigma-Aldrich (Dublin, Ireland). Wild Type Butrylcholinesterase (BuChE) was a kind gift from Oksana Lockridge, University of Nabraska, USA. Human liver and intestinal microsomes, BD Gentest™ were obtained from BD Biosciences, USA. Test compounds were dissolved in DMSO, than diluted in PRP or WP to give a final concentration not more than 0.25% DMSO, which pilot studies had determined not to affect platelet aggregation. No precipitation of test compound was observed following dilution.

Preparation of Human Platelets

Blood was collected from fully-consented healthy volunteers at the School of Pharmacy and Pharmaceutical Sciences who had not taken any drugs known to affect platelet function for at least 14 days prior to the study. PRP and WP ($2.5 \times 10^8$ platelets ml$^{-1}$) were prepared from blood. Briefly 36 ml whole blood was collected into 4 ml of 3.15% sodium citrate; this was centrifuged at 250 ¥g for 20 min (with gentle acceleration and deceleration). At this point PRP, which had separated from white blood cells and red blood cells, was gently removed. When WP were required this PRP was centrifuged at 700 g for 10 min (with gentle acceleration and deceleration) in the presence of prostacyclin. The platelet-poor plasma (PPP) was removed and the platelet pellet was washed three times with Tyrode's buffer, before being re-suspended in Tyrode's buffer to a concentration of 2.5 ¥108 platelets/ml.

Platelet Aggregation and its Inhibition by Aspirin Prodrugs

Platelet aggregation was measured by light aggregometry. Briefly, PRP and WP samples ($2.5 \times 10^8$/ml) were placed in an eight channel Platelet Aggregation Profiler® Model PAP-8E and incubated for 10 min at 37° C., with stirring at 900 r.p.m., prior to the addition of aggregating agents. Aggregation was initiated by the addition of agonists, and monitored by Aggro-Link software for at least 6 min. For experiments using inhibitors, aggregation was initiated after 10 min preincubation with test compounds.

To study the aggregatory potency of ADP, the concentration-response (0.3-10 µM) curves were generated. Collagen at different concentrations (2-5 µg/ml) was also used to induce platelet aggregation. Submaximal concentrations of agonists, i.e. the concentrations that gave approximately 95% of the maximal aggregation were used to study the effects of inhibitors of aggregation. Aspirin and aspirin prodrugs was incubated for various intervals prior to the addition of aggregating agents. Results were expressed in percent % changes in maximal light transmission, with 100% representing light transmission of platelet medium alone.

Investigation of the Role of Plasma BuChE in Activation of ST0701

To study the involvement of plasma BuChE in the activation of ST0701, purified BuChE (3 U/ml) was incubated with WP for 5 min in the aggregometer with stirring at 900 r.p.m. before the addition of the test compounds ST0701 which was incubated with the WP for a further 10 min, prior to the addition of collagen (5 ug/ml).

Effect of Physostigmine (Eserine) on Platelet Inhibitory Activity of Prodrugs.

Eserine (in DMSO, 10 µM, giving a final concentration≤0.25% DMSO, which pilot studies had determined not to affect platelet aggregation) was preincubated with PRP or WP for 5 min in the aggregometer with stirring at 900 r.p.m. before the addition of test compounds (ST0701-05), which were incubated in PRP or WP for a further 10 min prior to the addition of an agonist (10 µM ADP or 5 µg/ml Collagen) to induce platelet aggregation.

Effect of
1H-[1,2,4]Oxadiazolo[4,3-a]quinoxalin-1-one on
bioactivity of nitro-asa 1H-[1,2,4]Oxadiazolo[4,3-a]quinoxalin-1-one (ODQ, dissolved in 100% DMSO, used at a final concentration of 10 µM, which gave a final concentration not more than 0.25% DMSO) was preincubated with PRP or WP for 5 min in the aggregometer with stirring at 900 r.p.m. before the addition of test compounds (ST0701-05), which were incubated in PRP or WP for a further 10 min prior to the addition of an agonist (10 μM ADP or 5 μg/ml collagen) to induce platelet aggregation.

Effect of PMSF on Activity of ST0702 in WP

Phenylmethylsulphonylfluoride (PMSF) 20, 50 and 100 μM dissolved in EtOH (<0.2% EtOH, which pilot studies had determined not to affect platelet aggregation) was pre-incubated in WP in the aggregometer for 5 min with stirring at 900 r.p.m. before the addition of test compound ST0702 to the WP, which was further incubated for 10 min prior to the addition of collagen (2 μg/ml) to induce platelet aggregation.

Activity of Plasma Esterase

Cholinesterase Activity

PRP, WP samples ($2.5 \times 10^8$ platelets $ml^{-1}$), lysed WP samples and PPP were analyzed for the presence of BuChE activity, according to the method of Ellman, with some modifications. S-butyryltiocholine iodide (BTCI) at 1 mM in phosphate buffer pH8.0 at 37° C. was used as substrate to measure the activity of BChE in WP, PRP, PPP and in WP lysed with Triton X-100. Combined AChE and BChE activity was measured with 1 mM acetlythiocholine iodide (ATCI). An aliquot of 4 μl of WP, PRP, PPP or lysed WP, Ellman's reagent (DTNB 10 μM) and phosphate buffer pH 8.0 were incubated in a 96 well plate at 37° C. for 30 min. BTCI or ATCI was added to give a final concentration of 1 mM and the change in absorbance at 405 nm was measured over a period of 10 min on a plate reader.

para-Nitrophenyl Acetate (PNA) Assay

WP, PRP, PPP or lysed WP and 50 mM TrisHCl pH7.4 were incubated on a 96 well plate at 37° C. for 30 min. PNA at a final concentration of 3 mM was added to the plate and the change in absorbance at 405 nm was measured over a period of 10 min.

NPA hydrolyse activity could be due to CE (EC 3.1.1.1), BuChE, acetylcholinesterase (AChE, EC 3.1.1.7) or paraoxanase/arylesterase (PON, EC 3.1.8.1). To identify which esterases were involved in the hydrolysis of PNA, various inhibitors were incubated with the WP, PRP, PPP or lysed WP and 50 mM TrisHCl pH7.4 for 30 min at 37° C. prior to the addition of the PNA and the measurement of the change in absorbance at 405 nm. Physostigmine (100 μM), a cholinesterase inhibitor was used to check if BuChE/AChE played a role in the hydrolysis of PNA. Iso-OMPA a selective BuChE inhibitor was also used. PMSF (10-100 μM) was used to determine if serine proteases played any part in the hydrolysis of PNA by platelets. EDTA a calcium chelator was used to investigate the role played by PON esterases. BNPP a CE inhibitor of was used to investigate if carboxylesterases played a role in hydrolysis of PNA by platelets.

Control and Solvent Checks

Control experiments were performed throughout the course of each experiment to establish normal aggregation responses. Prior to each experiment, a sample of PRP or/and WP was incubated with 10 μl of DMSO for 10 min at 37° C. with stirring to ensure the solvent was having no inhibitor effect on the aggregation response.

Flow Cytometry

In order to analyze receptor expression on the surface of individual platelets and to minimize platelet activation caused by sample preparation procedures, no stirring or vortexing steps were used. The abundance of activated GPIIb/IIIa and P-selectin on the surface of platelets in the presence and absence of inhibitors was measured by flow cytometry. Platelet samples were first activated with agonists either collagen or ADP. When platelet aggregation reached 50% maximal light transmission the reaction was terminated by 10-fold dilution with physiologic saline. Resting platelets were used as control. In most of the experiments, platelets were preincubated with inhibitors for 10 min prior to the addition of agonists. Platelet samples were then incubated in the dark without stirring for 5 min at room temperature in the presence of saturating concentrations (10 μg/ml) of P-selectin (CD62P-APC). The activated GPIIb/IIIa platelet receptors were measured using PAC-1 monoclonal antibody at the same concentration as above. PAC-1 specifically recognizes an epitope on the high-affinity GPIIb/IIIa complex of activated platelets at or near the platelet (ref). Following incubation, samples were diluted in FACS Flow fluid and analyzed within 5 min using a BD FACSArray (BD Biosciences, Oxford, UK). Flow cytometry was performed on single stained platelet samples as described before (Ref). The instrument was set up to measure the size (forward scatter), granularity (side scatter) and cell fluorescence. A two-dimensional analysis gate of forward and side scatter was drawn in order to include single platelets and exclude platelet aggregates and microparticles. Antibody binding was measured by analyzing individual platelets for fluorescence. The mean fluorescence intensity was determined after correction for cell autofluorescence. For each sample, the fluorescence was analyzed using a logarithmic scale. Fluorescence histograms were obtained for 10,000 individual events. Data were analyzed using BD FACSArray software and expressed as a percentage of control fluorescence in arbitrary units.

Platelet Lysate Preparation

Platelet lysates were prepared by lysing WP with 10×RIPA buffer (20 mM Tris pH 7.4, 50 mM NaCl, 50 mM NaF, 5 mM EDTA, 20 mM pyrophosphate, 1 mM $Na_3VO_4$, 10% Triton X, 10 M PMSF, PICs) for 1 h on ice with intermittent vortexing. A Bradford assay was performed to determine the protein concentration of the platelet lysate samples. Platelet lysate samples were mixed with 2× non-reducing loading buffer (50 mM tris pH6.8, 2% SDS, 0.1% bromophenol Blue, 20% glycerol), or reducing loading buffer (50 mM Tris pH 6.8, 2% SDS, 0.1% bromophenol blue, 20% glycerol, 0.5% β-mercaptoethanol), boiled for 5 min, centrifuged and loaded onto SDS-PAGE gels.

Gel Electrophoresis and Immunoblot Analysis.

Proteins were electrophoretically separated under non-reducing and reducing conditions according to Laemmli. SDS-PAGE was performed with 7% (wt/vol) separation gels at a constant voltage of 160 V/h with the use of a Mini-Protean II gel system from Bio-Rad Laboratories (Hemel, Hempstead, UK). After electrophoretic separation, proteins were transferred from the gel onto Immobilon-NC membranes, according to the method of Towbin et al., using a Bio-Rad Mini-Protean II blotting system (Bio-Rad Laboratories). Proteins separated by SDS PAGE were transferred to nitrocellulose membranes by the method of Towbin et al Nitrocellulose membranes were blocked for 1 h in 5% BSA/NT Buffer (50 mM Tris pH 7.4, 170 mM NaCl, 0.2% IGEPAL) and incubated overnight at 4° C. with primary antibody anti-CES2 diluted 1:1000, or anti-CES1 diluted (1:2000) Subsequently, immunoblots were washed twice for 10 min each with 100 ml of 5% BSA/NT per blot and incubated for 1 h with peroxidase-conjugated secondary antibodies at a dilution of 1:10000. After the blots had been washed twice for 10 min with 5% BSA/NT and rinsed twice with NT Buffer, nitrocellulose sheets were developed by enhanced chemiluminescence. Calibration of molecular masses was based on the SDS-PAGE molecular weight standards from BIO-RAD. Liver microsomes were used as a positive control for CES1 and intestinal microsomes were used as a positive control for CES2.

Statistics

The data were analyzed using one-way analysis of variance (GraphPad Prism software 3.0). The results are expressed as mean±s.e.m. of at least three independent experiments. Tukey-Kramer multiple comparisons test, and paired and unpaired Student's t-tests were performed, where appropriate. Statistical significance was considered when $P<0.05$.

Results

Inhibition of Platelet Aggregation in WP Suspension

Figures 3A, 3B:
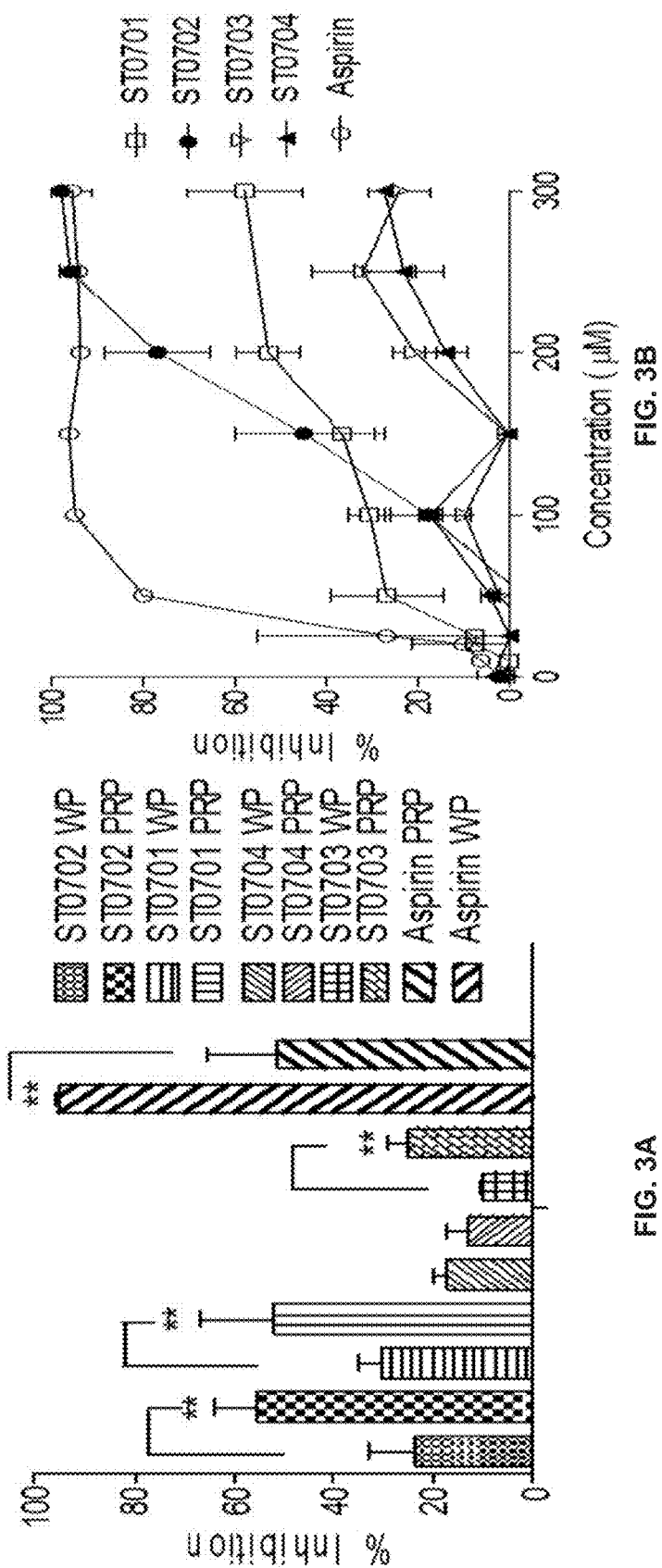
FIGS. 3A-3B illustrate inhibition of platelet aggregation in response to collagen (5 µg/ml) in platelet rich plasma (PRP) and washed plasma (WP) by test compounds (200 µM, n=6, **p<0.05). The prodrugs were generally less effective in WP, whereas aspirin was more effective in WP.

As shown in FIGS. 3A-3B, the test compounds and aspirin (100-300 μM) caused inhibition of platelet aggregation in PRP and WP stimulated by collagen (5 μg/ml). The $IC_{50}$ values for inhibition of WP aggregation are presented in Table 1. The prodrugs ST0701-05 were significantly less potent in WP suspension than in PRP (FIG. 3A). In contrast aspirin was more potent in WP ($IC_{50}$ 35 μM) than in PRP ($IC_{50}$ 92 μM). This effect may be due to protein binding (50%) or hydrolysis; aspirin interacts with albumin partly through transacetylation which complicates measurement of free drug. Of the prodrug compounds, ST0702 was the most efficacious inhibitor of collagen induced aggregation in WP ($IC_{50}$ 154 μM). ST0701 was more potent than ST0702 in this regard but less efficacious (50% inhibition at 500 μM (FIG. 3B)). The lack of effect of the other compounds in the absence of plasma BuChE strongly suggests that their antiplatelet effect in PRP are due to aspirin release. A role for plasma BuChE in activation of ST0701 was supported by the observation that its inhibitory actions were rescued in WP by the addition of human BuChE purified from plasma (3 U/ml). Aspirin and the aspirin prodrugs were tested as inhibitors of ADP (10 μM) induced platelet aggregation in PRP and WP (n=6) (FIG. 4A). The Inventors have already reported some initial results for ST0701, ST0703-04 at low concentration of ADP (3 μM)[7]. Nitrate compounds ST0703-04 were significantly more potent inhibitors of ADP (10 μM) induced aggregation than the ST0701-02 or aspirin (FIG. 4B). Aspirin caused consistently less inhibition of aggregation than ST0701/02 (which were similar in effect) but the difference was not significant at any single concentration.

Time Dependence of Inhibition

ST0701 and ST0702 (200 μM) were incubated in PRP for several time intervals (2, 5, 10, 20, 30 min) before addition of collagen (5 μg/ml) to stimulate platelet aggregation. Inhibition by ST0701 reached its maximum at 5 min (40% at 2 min). No significant inhibition of platelet aggregation was observed with ST0702 following 0-5 min preincubation. The inhibitory activity of ST0702 increased gradually with time and became maximal following 15-20 min preincubation.

Effects of Products of Hydrolysis of the Aspirin Prodrugs on Platelet Aggregation Several products of plasma hydrolysis of ST0701 (FIG. 2B) were available from a previous study that identified ST0701 as a true aspirin prodrug[6]. These were tested for their effect on collagen (5 μg/ml) induced aggregation in order to see if they contributed to the inhibitory actions of ST0701. Isosorbide, salicylic acid, isosorbide-2,5-disalicylate and isosorbide-5-salicylate were incubated in PRP in the concentration range 10-300 μM before triggering aggregation (FIG. 2B). None of the hydrolysis products significantly inhibited aggregation induced by collagen (5 μg/ml) (n=3 at 11 concentration levels). The compounds were also co-incubated in the presence of aspirin to see if they potentiated its actions (either pharmacologically or by affecting disposition). None of the compounds affected aspirin's activity apart from isosorbide-disalicylate trended non-significantly towards an attenuation of aspirin's inhibitory effect (maximally 10%) when co-incubated in the range 50-500 μM.

Influence of ODQ on Inhibition of Aggregation Induced by Aspirin Prodrugs

ST0703-04 were significantly more potent than aspirin and the other aspirin prodrugs (ST0701-ST0702) at inhibiting ADP (10 μM) induced platelet aggregation. In order to determine if NO played a role in this effect, the irreversible guanyl cyclase inhibitor ODQ was preincubated with the PRP in the aggregometer for 5 min before the addition of aspirin or aspirin prodrugs. Platelet aggregation was then initiated by the addition of ADP (10 μM). ODQ cause a small but significant attenuation of the inhibitory action of nitrates ST0703/04 (FIG. 4C). ODQ caused some inhibition when incubated alone with ADP and it increased the inhibition of ADP induced platelet aggregation by aspirin, ST0701 and ST0702.

Effect of Physostigmine on Platelet Aggregation Inhibition

Figure 5A:
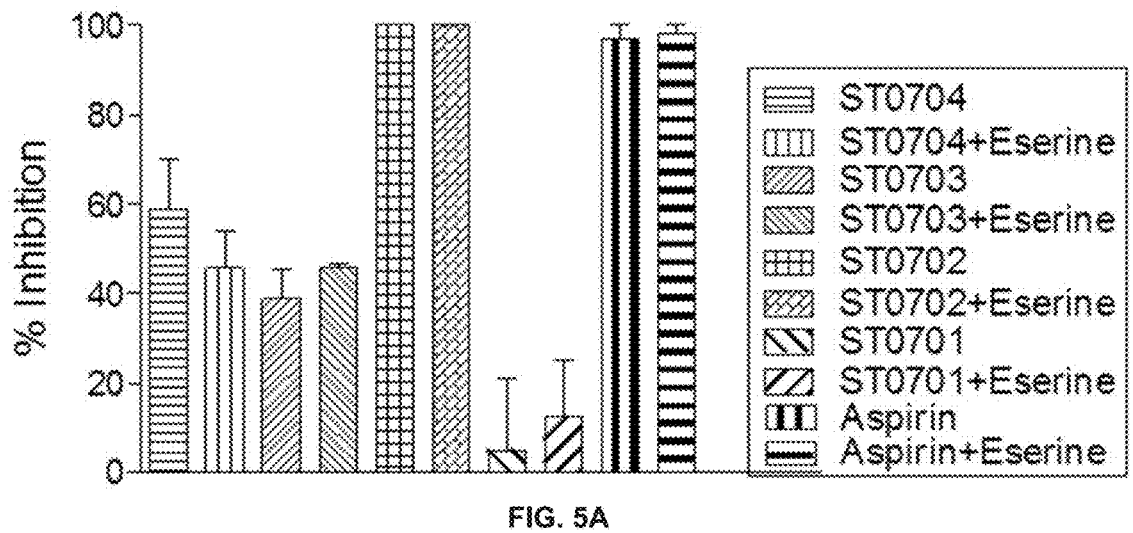
FIGS. 5A-5B show inhibition (%) of platelet aggregation in response to collagen (5 µg/ml) in the absence and presence of physostigmine (eserine) (10 µM) an inhibitor of human plasma butyrylcholinesterase (BuChE).
Figure 5B:
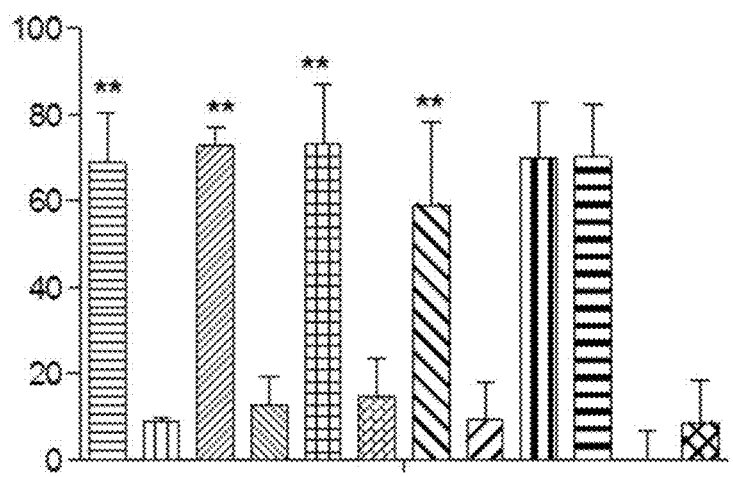

The test compounds and aspirin were incubated in PRP at maximally effective concentration of 300 μM to inhibit collagen-induced aggregation in the presence or absence of 10 μM physostigmine (eserine). This concentration level was separately shown to cause complete inhibition of plasma BuChE. All of the PRP experiments were conducted in samples that had normal BuChE levels (there are several polymorphisms leading to low BuChE activity). Eserine addition resulted in an almost complete loss of inhibitory activity of all of the test compounds (FIGS. 5A-5B) in PRP. In contrast, eserine did not exert significant effects on inhibition of aggregation afforded by aspirin. In WP suspension eserine did not affect the inhibitory actions of the prodrugs or aspirin towards collagen-induced aggregation (FIGS. 5A-5B).

Expression of Platelet Surface Glycoproteins

Figure 6A:
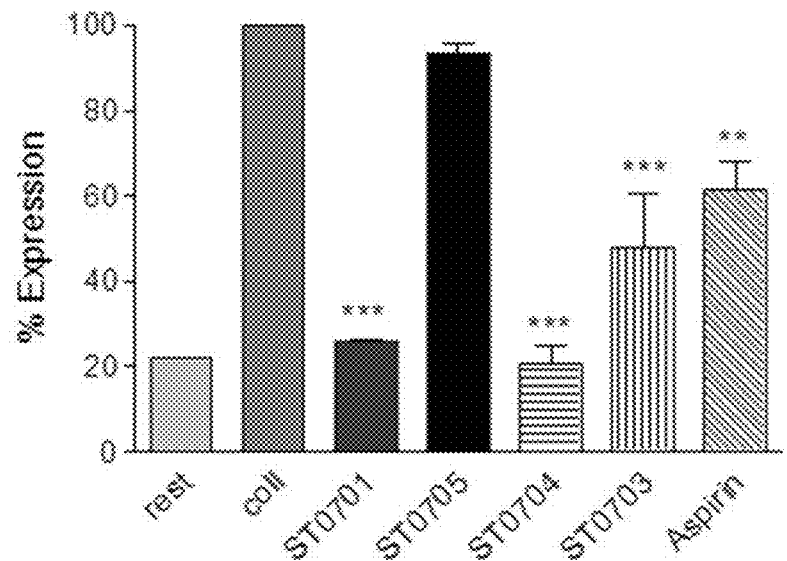
FIGS. 6A-6B illustrate the effects of ST0701, ST0703, ST0704 and ST0705 and aspirin at 60 µM on platelet receptors P-selectin (FIG. 6A) and GPIIb/IIIa (FIG. 6B) in PRP. Data are mean±SEM, n=3.
Figure 6B:
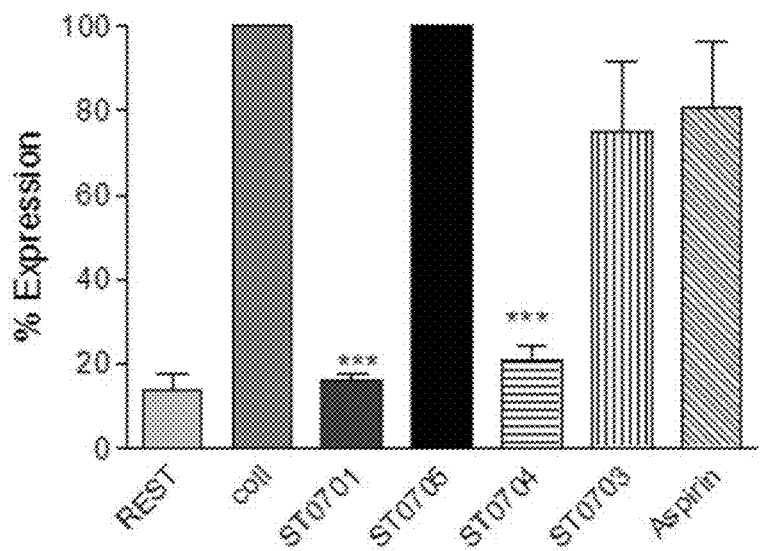

The activation of glycoprotein integrin receptor GPIIb/IIIa is crucial for platelet aggregation to occur. In addition the translocations of P-selectin from α-granules to the platelet surface membrane underlie platelet adhesion. We measured the expression of these receptors following collagen stimulation in the presence of the test compounds at 60 μM. As shown in FIGS. 6A-6B, ST0701 and nitrate hybrid ST0703 significantly suppressed activation of GPIIb/IIIa and translocation of P-selectin in PRP to resting levels but not in WP. ST0705 did not cause significant inhibition of either platelet marker in PRP or in WP. ST0703 was equipotent with aspirin in PRP but not in WP. The effects overall correlated with the known extent of aspirin generation in plasma solution. U46619 a thromboxane mimetic was used to investigate if the prodrugs had any inhibitory effects downstream of thromboxane. Neither aspirin nor the aspirin prodrugs had any inhibitory effect on platelet aggregation induced by U46619 in PRP.

Plasma and Platelet Esterase Activity

Figure 7A:
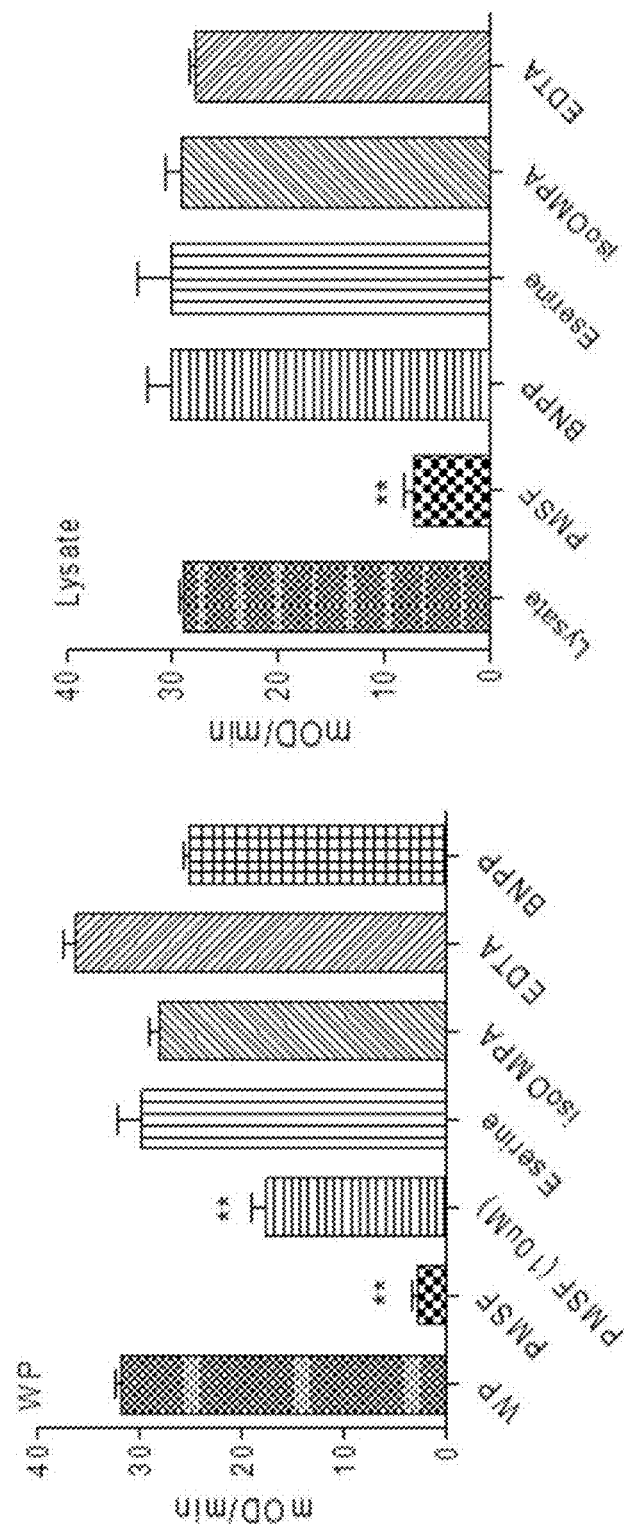
FIG. 7A illustrates the effect of various esterase inhibitors (100 µM) on platelet turnover of p-nitrophenylacetate in the presence of WP or platelet lysate, as reflected in change in optical density min$^{-1}$.
Figure 7B:
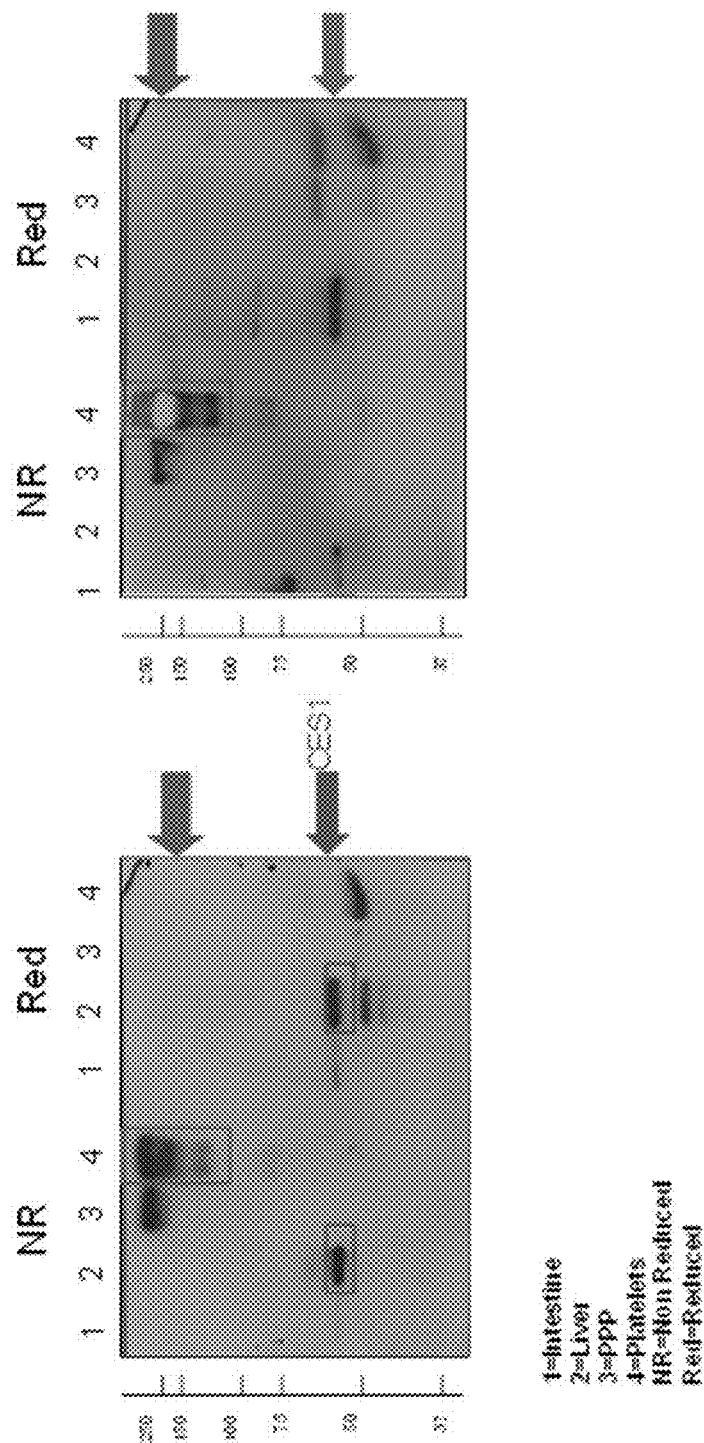
FIG. 7B shows a representative (from similar experiments) Western blotting of platelet lysate obtained from WP using antibodies against CES-1 and CES-2. Human liver and intestinal microsomes were used as standards for CES-1 and CES-2. Human liver contains mostly CES-1 whereas intestinal microsomes are rich in CES-2; PMSF, phenylmethylsulphonyl fluoride; BNPP, bis-p-nitrophylphosphate; IsoOMPA, tetraisopropylpyrophosphoramide; EDTA, ethylenediaminetetraacetic acid.
Figure 8:
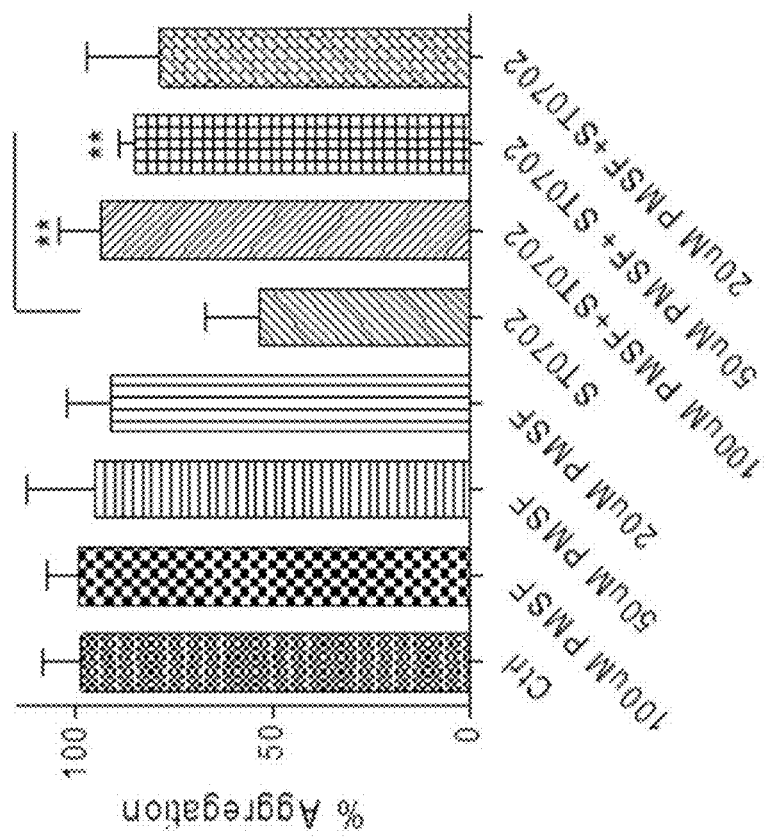
FIG. 8 shows the effect of various PMSF (20-100 µM) on the inhibitory effect of ST0702 (300 µM) on platelet aggregation in response to collagen (5 µg/ml) in WP (n=4).

Plasma and platelet BuChE activity was measured using the Ellman assay with butyrylthiocholine and acetylthiocholine as substrate. NPA hydrolase activity was also determined since this substrate can be hydrolysed by CEs, which hydrolyse choline esters only slowly. BuChE activity in plasma and PRP was 6-9 μM butyrylthiocholine $min^{-1}$ $ml^{-1}$. In contrast there was negligible esterase activity detectable in WP or washed platelet homogenate using the BuChE substrate. Weak activity (3-5 μM $min^{-1}$ $ml^{-1}$) was also detected in PRP and PPP using the substrate pNPA. This was probably due to cholinesterase since there is little or no CE in human plasma. There was significant pNPA hydrolysing activity in WP and in platelet lysate. As pNPA hydrolysis activity could be due to CE, BuChE, AChE or pPON esterases a series of inhibitors were used to classify the esterases present in the WP. Physostigmine a cholinesterase inhibitor caused a 25% reduction in pNPA hydrolyse activity of platelets. PMSF a serine protease inhibitor almost completely inhibited NPA activity in WP at concentration of 100 µM and inhibited NPA activity by 50% at 10 µM (FIGS. 7A-7B). EDTA a calcium chelator which inhibits PON had no effect on NPA activity of WP at concentrations up to 0.5 mM. Iso-OMPA (10-100 µM) a selective butrylcholinesterase inhibitor had no effect on PNA activity of WP or lysed platelets. Surprisingly, BNPP (10-100 µM) a specific CE inhibitor had no significant effect on NPA activity of WP or lysed platelets. The NPA hydrolyse activity in the platelet suspension was not due to BuChE or PON esterases. Probing platelet lysates run on nonreducing polyacrylamide gels with anti CES1 and anti-CES2 antibodies we observed bands with Mwt ranging from 150 kDa-400 kDa, not at the predicted Mwt of 62 kDa (FIGS. 7A-7B). These bands were similar in Mwt to the bands observed by Oertel et al by staining for alphaNA esterases[30]. These bands appear to be a carboxylesterase type because of their cross reactivity with CES-1/2 antibody and ability to process pNPA. When the gels were reduced these high Mwt bands disappeared and were replaced by a doublet, with one band at ~50 kDa and another at ~65 kDa (FIGS. 7A-7B). WP suspensions were next treated with PMSF, before addition of ST0702 and platelet activating agent. PMSF attenuated the ability of ST0702 to inhibit platelet aggregation in a concentration dependent manner with maximal effects at 100 mm.

Effect of Phenylmethylsulphonyl Fluoride on ST0702 Platelet Aggregation Inhibition Of the prodrug compounds, 2 (ST0702) was the most efficacious inhibitor of collagen induced aggregation in WP (IC50 154 µm). ST0702 had a greater than expected potency in WP where there is an absence of esterases responsible for the hydrolysis of these prodrugs in PRP. To determine if any PMSF-sensitive enzyme in platelets play a role in the hydrolysis of ST0702 in WP, PMSF was pre-incubated with WP at increasing concentrations up to 100 mm for 5 min, with stirring before the addition of ST0702 (200 mm). Platelet aggregation was then initiated by addition of collagen (2 µg/ml). PMSF had no significant effect on collagen-induced aggregation. However PMSF (100 µM) significantly attenuated the effect of ST0702 (200 µM) on collagen-induced aggregation in WP. Lower amounts of PMSF (50 µM, 20 µM), also slightly attenuated the effect of ST0702 on collagen-induced aggregation in WP, although this attenuation was not significant.

Discussion

This is the first pharmacological study into mechanisms of platelet inhibition by true aspirin prodrugs. The compounds in this study were reported to undergo productive processing generating aspirin in the presence of BuChE from human plasma[6,7]. This is due to a particular fit for the BuChE active site that overrides the usual acetyl group preference for this enzyme, which prevents other aspirin esters from releasing aspirin. The compounds are rapidly hydrolysed in plasma solution generating aspirin to 30-80% of the starting ester concentration[6,7]. ST0701 is the most effective aspirin prodrug ever discovered producing slightly less than a stoichiometric equivalent of aspirin. However, it is a significantly more potent inhibitor of platelet aggregation than aspirin. The platelet inhibitory properties of the nicotinate codrug ST0702 (2), which releases <40% aspirin on a stoichiometric basis, have not been reported previously. In this study, ST0702 was equipotent with aspirin (90 µM) in the inhibition of aggregation in PRP stimulated by collagen (5 mg/ml). The nitrate compounds ST0703 and ST0704 were reported to be more potent inhibitors of platelet aggregation in PRP than aspirin in response to collagen (5 µg/ml) and ADP (3 µM)[6,7]. In this study we used a higher concentration of ADP to obtain a more reliable biphasic response to further probe the effect of the compounds on ADP-stimulated aggregation. Meanwhile, the nitrate hybrid ST0705 releases <10% aspirin in solutions containing human plasma which made it a useful control to probe for the role of aspirin and NO release in the effects of in the nitric oxide-aspirin hybrids (ST0703 and ST0704). Several lines of evidence from this study indicate that the platelet inhibitory actions of the prodrugs ST0701-04 are due to aspirin release: (i) the test compounds were significantly more potent or effective in PRP than in WP; (ii) their inhibitory actions in PRP were abrogated following preincubation with the cholinesterase inhibitor eserine; (iii) inhibition of collagen induced aggregation in PRP by 200 µM ST0701 and ST0702 was time dependent (whereas aspirin's inhibition effects were not); (iv) effects of the prodrugs on platelet GPIIb/IIIa and P-selectin expression were similar qualitatively to aspirin indicating that the inhibitory effects occurred upstream of receptor release/translocation; (v) the products of plasma esterase hydrolysis of ST0701 did not exert platelet inhibitory effects or modulate the platelet inhibitory properties of aspirin when co-incubated; (v) ester ST0705, which does not release aspirin, was not active. Aspirin's failure to effectively inhibit ADP induced aggregation is a clinically important deficiency of the drug which has prompted others to evaluate aspirin-NO hybrids. A number of NO-aspirin hybrids types including aspirin-furoxans, -diazeniumdiolates and -nitrates have been studied in vitro as platelet aggregation inhibitors. The furoxans inhibit platelet aggregation in PRP mainly through nitric oxide release since this hybrid type is exclusively hydrolysed at the acetyl ester in media containing human plasma. The nitrate ester NCX-4016 does not inhibit platelet aggregation in PRP. It inhibits platelet aggregation in WPbut in an NO and cGMP independent manner. NCX-4016 inhibits purified COX preparations by direct interaction, i.e. direct acyl transfer onto COX. This ability is lost in media containing human plasma because of a more rapid deacetylation by BuChE than transacetylation of COX. Inhibition of platelet aggregation with NCX-4016 is therefore only observed in WP where esterase levels are low. The use of organic nitrates in alleviating the symptoms of angina has its mechanistic basis in nitric oxide release from endothelial and smooth muscle cells. Platelets are able to stimulate NO release from organic nitrates but much less effectively than smooth muscle cells. Nitric oxide has a well characterised endogenous role in gastric mucosal protection and maintenance of mucosal defense is a general property of organic nitrate drugs. While organic nitrates produce insufficient nitric oxide locally to affect platelet aggregation, they have potential to mimic or augment its endogenous protective role in the intestinal mucosa.

Whereas collagen-induced aggregation at submaximal concentrations depends predominantly on the production of TXA2, it is highly susceptible to inhibition by COX inhibitors such as aspirin. ADP addition to platelet suspension produces a biphasic aggregation profile. The first phase of ADP induced aggregation is independent of TXA2 production and hence COX inhibition (and thus resistant to aspirin). However the second phase of ADP-induced aggregation is dependent on the production of TXA2 and can be inhibited by COX inhibitors such as aspirin. We were interested to see if the NO-aspirin prodrugs retained the ability to inhibit the second (COX dependent) phase of ADP-induced aggregation while being able to dampen or reverse the COX-independent first phase. This could be useful in a disease situation where platelets are exposed to multiple pathophysiological stimuli. The nitrate substituted compounds ST0703 and ST0704 were significantly more effective inhibitors of ADP (10 μM) induced aggregation than the non-nitrate substituted compounds and aspirin. This effect appears to be due partly to nitric oxide release because it was attenuated in the presence of the soluble guanyl cyclase inhibitor ODQ which abrogates the platelet inhibitory effects of nitric oxide. The effect of ST0703 and ST0704 on ADP-induced aggregation was attenuated in the presence of the soluble guanyl cyclase inhibitor ODQ which blocks to some extent the platelet inhibitory effects of NO.[50] In this study, ODQ itself partially inhibited platelet aggregation in response to collagen and it amplified the platelet inhibitory effects of the aspirin and prodrug ST0701 which does not produce NO. ODQ therefore had only a modest effect when co-incubated with the nitrate hybrids ST0703 and ST0704, because while it attenuated the effect of NO release it amplified the aspirin effect. Overall, the evidence for a contribution from a NO-mediated effect from ST0703 and ST0704 derives from their inhibitory efficacy towards ADP-induced aggregation, as well as the observed reversal of the trend towards increased inhibition when aspirin and its prodrugs were co-incubated with ODQ.

Interestingly, the inhibitory effect of ST0703 and ST0704 in ADP induced aggregation were abolished in the presence of eserine, which blocks aspirin release in PRP (data not shown). ST0705, which releases nitric oxide but little aspirin, was not effective as an inhibitor of ADP induced aggregation. These observations imply that aspirin and NO were acting synergistically in causing the inhibitory effects of ST0703 and ST0704. The other outstanding question in this study was the greater than expected potency of the ester compounds and the significant inhibitory actions in WP suspension of ST0701 and ST0702 where BuChE was absent. We showed that BuChE is not relevant to the inhibitory actions of ST0702 in WP because the inhibitory effect was not abolished by pretreatment with eserine. A possible explanation for this was that the compounds were taken up by platelets and activated by a platelet esterase, possibly a CE. We therefore profiled the esterase activity in PRP, PPP, WP and platelet lysate using a range of substrate and esterase specific inhibitors. As expected, significant BuChE activity was detected in PRP and PPP but weak CE and AChE activity. Platelets are reported to possess a low level BuChE activity possibly plasma derived but trapped in the platelet canalicular system. A platelet membrane-associated AChE activity has also been reported. These reports are consistent with our observation of weak WP and lysate turnover of the appropriate thiocholine esters. Several α-naphthyl acetate (αNA) hydrolysing esterase has been separated from platelets although platelet αNA was reported to be resistant to inhibition by PMSF. Our results show that there is a multimeric protein in platelets that produces reduced fragments in the range 50-60 kD with high immunoreactivity towards human CES-1 and CE-2. These proteins are presumed to be the enzyme(s) catalysing the hydrolysis of CE substrate pNPA. The platelet hydrolytic activity was blocked by the general serine esterase/protease inhibitor PMSF (50-100 μM). The inhibitory activity of ST0702 (200-300 μM) in WP were abolished when the suspension was pretreated with PMSF (100 μM) indicating that a PMSF sensitive enzyme in platelets causes the activation of ST0702 in WP. The result has significance for the potential utility of the compound for it shows that i) the compound could be activated and cause platelet inhibition in a patient with low plasma esterase activity; ii) it indicates that the ST0702 does not possess intrinsic anti-platelet activity and iii) it raises the prospect of increased cellular uptake and intracellular activation, potentially increasing potency. Despite releasing only 30-40% aspirin in PPP relative to a stoichiometric amount of aspirin, ST0702 has similar anti-platelet activity with respect to stimulation with ADP and collagen. The ester prodrugs are significantly more lipophilic than aspirin at pH 7.4 as reflected in RPHPLC retention and as expected from abrogation of the carboxylate. A plausible explanation for their high potency in PRP is that they partition into the platelet membrane to a greater extent than aspirin from where they undergo activation mediated by esterases at the platelet surface or intracellularly producing locally high concentrations of aspirin. Enhanced cellular uptake would be interesting to measure in other pathologically relevant cell types.

Conclusions

Inhibition of platelet aggregation by aspirin prodrugs ST0701-04 is primarily due to aspirin release. In the case of nitrate substituted compounds inhibitory effects are due to release of both NO and aspirin with promising effects on ADP-induced aggregation. ST0702, a nicotinic acid-aspirin codrug is activated by a PMSF sensitive platelet esterase in WP platelet suspensions. Its unexpected potency in PRP appears to be due to platelet uptake and drug release. Thus, aspirin prodrugs effectively inhibit human platelet aggregation and as such may be an alternative to conventional aspirin.

TCIPA Studies

Tumour cell-induced platelet aggregation (TCIPA) facilitates cancer cell invasion, angiogenesis and the formation of metastatic foci. Tumour cell-induced platelet aggregation can be modulated by pharmacological inhibitors of matrix metalloproteinase-2 (MMP-2) and ADP, however, the major cyclooxygenase inhibitor aspirin has failed to prevent TCIPA. The Inventors have tested the pharmacological effects of a new group of isosorbide-based aspirin prodrugs on TCIPA. TCIPA was induced by human adenocarcinoma and fibrosarcoma cells under no flow and flow conditions. The release of gelatinases and P-selectin expression during TCIPA were studied by zymography and flow cytometry, respectively. Tumour cells caused platelet aggregation. This aggregation resulted in the release of MMP-2 and a significant up-regulation of P-selectin on platelets indicative of platelet activation. Pharmacological modulation of TCIPA revealed that ST0702, one of the aspirin prodrugs, downregulated TCIPA while aspirin was ineffective. One of ST0702 metabolites, 5-nicotinate salicylate (ST0702 salicylate) was also studied. It was found that ST0702 salicylate downregulated both ADP-stimulated platelet aggregation and TCIPA. The results provided and discussed below results show that ST0702 is an effective inhibitor of TCIPA in vitro. The salicylate metabolite is thought to contribute to the effects of ST0702 by inhibiting ADP-mediated TCIPA. The inventors have developed a new group of isosorbide-based aspirin pro-drugs that were found to be potent inhibitors of ADP- and collagen-induced platelet aggregation (Jones et al., 2009). Indeed, several pro-drugs were more potent inhibitors of aggregation than regular aspirin. The aim of the present study was to determine if the observed increase in potency in platelet aggregation assays translates into an effect in TCIPA. Accordingly, a selection of pro-drugs (FIG. 2A) were evaluated as inhibitors of TCIPA under conditions where aspirin itself is ineffective. Some of these compounds are designed to simultaneously release a second pharmacologically active moiety (e.g. nitric oxide) that might make them more suitable for interrupting processes such as TCIPA that operate along multiple activation pathways. One of the test compounds, an aspirin-nicotinic acid codrug (ST0702), under development as a dual antiplatelet and lipid modifying agent, markedly inhibited TCIPA under both no flow and flow conditions. We have been able to determine the mode of action of ST0702 as an inhibitor of TCIPA by monitoring its activation during platelet-tumour cell interactions.

Material and Methods for TCIPA Studies

Reagents

All reagents were purchased from Sigma-Aldrich (Dublin, Ireland) unless otherwise indicated. Collagen and ADP was obtained from Chronolog (Havertown, Pa., U.S.A.). Allophycocyanin (APC)-conjugated monoclonal antibody against human platelet P selectin (CD62P) were purchased from BD Biosciences (Oxford, UK).

The compounds were dissolved in DMSO, then diluted in PRP or WP to give a final concentration not more than 0.25% DMSO, which pilot studies had determined not to affect platelet aggregation. No precipitation of any drug was observed following dilution.

Tumour Cell Culture

Three human tumor cell lines, 59M ovarian adenocarcinoma, Caco-2 colon adenocarcinoma and HT1080 fibrocarcinoma cells, were obtained from the European Cell Culture Collection. Cell lines were cultured as monolayers in 75 ml culture flasks at 37° C. in a humidified atmosphere with 5% $CO_2$. 59M cells and HT1080 were cultured in Dulbecco's Minimum Essential Medium (DMEM) supplemented with 10% fetal bovine serum (FBS) and gentamycin (0.05 mg/ml), penicillin (0.06 mg/ml), and streptomycin (0.01 mg/ml). Caco-2 cell line was cultured in Minimum Essential Medium (MEM) supplemented with 20% FBS and the same antibiotics as above. The cells were supplied with fresh medium and subcultured three times each week.

Preparation of Human Washed Platelets

Blood was collected from healthy volunteers who have not taken any drugs known to affect platelet function for at least 14 days prior to the study. Washed platelet suspensions ($2.5\times10^{11}$ platelets $1^{-1}$) were prepared from blood an mixed with the anticoagulant sodium citrate (0.315% final concentration).

Platelet Aggregation Under Static Conditions

The interactions between platelets and tumor cells were measured by light aggregometry (Alonso-Escolano et al., 2004; Jurasz et al., 2001b; Radomski et al., 1991). Briefly, washed platelet samples ($2.5\times10^8$/ml) were placed in an eight channel PAP 8 aggregometer (BIO/DATA CORPORATION, Horsham, Pa., U.S.A.) and incubated for 10 min at 37° C., with stirring at 900 r.p.m., prior to the addition of aggregating agents. For most experiments, collagen at a concentration that resulted in maximal aggregation (5 µg/ml) was used as a control agonist. TCIPA was initiated by the addition of cancer cells, and monitored by Aggro-Link software for at least 30 min. For experiments using inhibitors, aggregation was initiated after 10 min preincubation with these compounds.

To study the ability of the aspirin pro-drugs to inhibit TCIPA in WP cancer cell lines such as HT1080 cells ($2\times10^5$/ml), CaCo2 cells ($1.5\times10^3$/ml) or 59M cells ($1\times10^3$/ml) were used in the presence or absence of aspirin nicotinate (ST0702), ISAS, orthonitrate and metanitrate at 300 and 500 µM. Platelet aggregation was initiated in washed platelets (WP) using HT1080 cells ($2\times10^5$/ml), CaCo2 cells ($1.5\times10^3$/ml) or 59M cells ($1\times10^3$/ml). In addition, regular aspirin (300 and 500 uM) was used as control. Results were expressed in percent changes in maximal light transmission, with 100% representing light transmission of platelet medium alone. ST0702 is hydrolyzed by plasma esterases along two pathways liberating both aspirin and 5-nicotinate salicylate (ST0702 salicylate)(metabolite). The latter is further processed to isosorbide-5-nicotinate and eventually to nicotinic acid. The orthonitrate and metanitrate compounds liberate aspirin and nitric oxide (NO). ISAS meanwhile is hydrolysed to aspirin and salicylic acid. Aspirin (300 and 500 µM) was used in control experiments. Results were expressed in percent changes in maximal light transmission, with 100% representing light transmission of platelet medium alone. Further experiments were performed with ST0702 salicylate (500 µM). This was obtained by flash chromatography as a hydrolysis product of ST0702 during isolation of the parent compound. Its purity and identity was confirmed by NMR, HPLC and HRMS.

To study whether or not aspirin prodrugs had any direct effect on tumour cells, nictoinate was preincubated with different cell lines and added to the platelet suspension. TCIPA was monitored for at least 30 min.

To study also the effect of physostigmine on activity of aspirin prodrugs, physostigmine (10 uM dissolved in EtOH) was preincubated with WP for 5 min in aggregometer with stirring at 900 r.p.m. before the addition of aspirin or aspirin prodrugs. Platelet aggregation was initiated after 10 min incubation with aspirin/aspirin prodrugs by the addition of HT1080 cells ($2\times10^5$/ml), CaCo2 cells ($1.5\times10^3$/ml) or 59M cells ($1\times10^3$/ml).

Effect of Physostigmine (Eserine) on Platelet Inhibitory Activity of ST0702 Salicylate Eserine (10 µM) was incubated with PRP for 5 min in the aggregometer with stirring at 900 r.p.m. before the addition of test compound ST0702 salicylate (500 µM), which was incubated in PRP for a further 10 min prior to the addition of the agonist ADP (10 µM) to induce platelet aggregation.

Flow Cytometry

In order to analyze receptor expression on the surface of individual platelets and to minimize platelet activation caused by sample preparation procedures, no stirring or vortexing steps were used. The abundance of P-selectin on the surface of platelets in the presence and absence of inhibitors was measured by flow cytometry. Platelet samples were first activated with 59M cells ($1\times10^3$/ml). When platelet aggregation reached 50% maximal light transmission the reaction was terminated by 10-fold dilution with physiologic saline. Resting platelets were used as control. In most of the experiments, platelets were preincubated with inhibitors for 10 min prior to the addition of 59M cells ($1\times10^3$/ml). Platelet samples were then incubated in the dark without stirring for 5 min at room temperature in the presence of saturating concentrations (10 µg/ml) of P-selectin (CD62P-APC). Following incubation, samples were diluted in FACS Flow fluid and analyzed within 5 min using a BD FACSArray (BD Biosciences, Oxford, UK). Flow cytometry was performed on single stained platelet samples. The instrument was set up to measure the size (forward scatter), granularity (side scatter) and cell fluorescence. A two-dimensional analysis gate of forward and side scatter was drawn in order to include single platelets and exclude platelet aggregates and microparticles. Antibody binding was measured by analyzing individual platelets for fluorescence. The mean fluorescence intensity was determined after correction for cell autofluorescence. For each sample, the fluorescence was analyzed using a logarithmic scale. Fluorescence histograms were obtained for 10,000 individual events. Data were analyzed using BD FACS Array software and expressed as a percentage of control fluorescence in arbitrary units.

Microscopy of TCIPA

The structure of platelet-tumor cell aggregates was studied using phase-contrast microscopy (Alonso-Escolano et al., 2004; Jurasz et al., 2001). Briefly, 59M cells ($1\times10^3$/ml) were added to the platelet suspension ($2.5\times108$/ml) in the presence or absence of aspirin and aspirin prodrugs, and aggregation was terminated at 50% maximal aggregation, as determined using the aggregometer. The samples were fixed by adding 2% paraformaldehyde in Tyrode's solution, pH 7.4, and then incubated for 30 min at room temperature. Aliquots of each sample were then taken for phase-contrast microscopy examination using an Olympus CKX41 microscope (Olympus America Inc., Melville, N.Y., U.S.A.). Photomicrographs were captured using a digital camera and MicroFire (Olympus America Inc.) software (Alonso-Escolano et al., 2004; Jurasz et al., 2001).

Sample Preparation for Zymography

Sample collection was carried out as previously described (Jurasz et al., 2001; Medina et al., 2006). Briefly, platelets at a concentration of $2.5\times10^8$/ml were placed into lumi-aggregometer and tumor cells (59M) were added at $1\times10^3$/ml. When platelet aggregation reached 50% maximal light transmission the reaction was terminated and samples were collected. The samples were then centrifuged at 900×g at room temperature for 10 min. After centrifugation, platelet releasates were collected and stored at −80 C until assayed for the presence of MMP activity by zymography.

Zymography

Gelatin zymography was used to detect the activity of MMP-2 in the releasates as previously described (Alonso-Escolano et al., 2004; Jurasz et al., 2001; Medina et al., 2006). Briefly, samples were subjected to 10% sodium dodecyl sulfate-polyacrylamide gel electrophoresis (SDS-PAGE) with copolymerized gelatin (0.2%; Sigma Chemical Co, St. Louis, Mo.) incorporated as a substrate for gelatinolytic proteases. After electrophoresis, the gels were washed with 2.5% Triton X-100 (3 times, 20 minutes each), and then incubated for 48 h at 37C.° in enzyme assay buffer (25 mM Tris HCl, 0.9% NaCl, 5 mM $CaCl_2$ and 0.05% $Na_3N$, pH=7.5). The conditioned medium of HT-1080 human fibrosarcoma cells (that contains high amounts of proMMP-2, MMP-2, proMMP-9 and MMP-9), was used as control. After 72 hours development, gels were fixed and stained in 40% methanol, 10% acetic acid and 0.1% (wt/v) Coomassie Blue R-250 (Sigma Chemical Co, St. Louis, Mo.) for 1 hour and then de-stained in 4% methanol with 8% acetic acid. The gelatinolytic activities were detected as transparent bands against the background of Coomassie blue-stained gelatin. The intensities of the separate bands were analyzed and quantified using ChemiDoc XRS System (Bio-Rad, Hercules, Calif., U.S.A.). The gelatinolytic activity of each band was expressed as arbitrary units of density/mg protein.

Flow-Mediated TCIPA Using an Ultrasound Standing Wave Trap

The ultrasound trap had three essential features: a transducer (Ferroperm, Kvistgard, Denmark) in a housing of radial symmetry, an aqueous phase and a reflector that provided optical access from above. The trap was driven with a function generator (Hewlett Packard 33120A, UK). Microscopic observation occurred with a fast, high-resolution XM10 camera (Soft Imaging System, SIS, GmbH) mounted on an Olympus BX51M reflection epi-fluorescence microscope. Images were captured by a standard PC equipped with the Cell-D image acquisition software (Soft Imaging System, SIS, GmbH).

The experimental procedure was as follows: 59M cells were introduced into the trap, the acoustic field (2.13 MHz, 0.85 MPa) was initiated and cell clusters were allowed to form. Clusters remained levitated in suspension for 10 min. Washed platelets ($2.5\times10^8$/ml) were introduced into the trap at a flow rate of 3 μl/min. Perfusion of washed platelets around the cluster proceeded following initial adhesion of platelets to the periphery of the cluster.

To study the effect of aspirin and aspirin prodrugs in TCIPA, washed platelets were pre-incubated for 10 min at room temperature with the inhibitors: aspirin, nicotinate, ISAS, ISMNA, ortho and meta (all at a concentration of 500 μM), prior to their introduction into the ultrasound trap. Those aspirin pro-drugs which were found to have an inhibitory effect under static conditions were tested; ST0702, ISAS, orthonitrate and metanitrate (500 μM); aspirin (500 μM) was used as control. The cell cluster-platelet aggregate remained under microscopic observation for further 10 min (the upper time limit established in the current study) under continuous flow conditions. Further experiments were performed with ST0702 salicylate (500 μM).

Profiling the Breakdown of ST0702 During the TCIPA Experiment

To study the hydrolysis of the prodrug ST0702 in TCIPA, HPLC analysis of supernatants and lysates was performed. Briefly WP ($2.5\times108$/ml) were placed in an eight channel PAP 8 Aggregometer. ST0702 (500 μM) was incubated with the platelets with stirring for 10 min, prior to the addition of cancer cells, HT1080 ($2\times105$/ml) or CaCo2 ($1.5\times103$/ml) to induce aggregation. TCIPA was monitored for 30 min, supernatants/lysates were collected as soon as control (HT1080 or CaCo2 alone), plateaued and reached maximal aggregation. For collection of supernatant, after the control plateaued and reached maximal aggregation, 100 μM PMSF was added and the washed platelet/ST0702 suspension was centrifuged at 13000×g for 5 min at 4° C., the supernatant was removed and stored at −20° C. until analysis by HPLC. For collection of lysate after the control plateaued and reached maximal aggregation, ice cold 10×RIPA lysis buffer (20 mM Tris pH7.4, 50 mM NaCl, 50 mM NaF, 5 mM EDTA, 20 mM pyrophosphate, 1 mM Na3VO4, 10% Triton-X, 10 mM PMSF and 10×PICs (5 mM AEBSF, 1.5 mM Aprotinin, 10 uM E-64 Protease Inhibitor, 10 uM Leupeptin hemisulfate)) was added to WP/ST0702 suspension. Samples were stored on ice for 1 h with frequent vortexing to promote lysis. The samples were centrifuged at 13000×g for 5 min at 4° C. and the supernatant lysates stored at −20° C. until analysis by HPLC. HPLC was performed as described previously but with detection at 260 nm (Jones, 2009).

Statistics

The data were analyzed using one-way analysis of variance (GraphPad Prism software). The results were expressed as mean±s.e.m. of at least three independent experiments. Tukey-Kramer multiple comparisons test, and paired and unpaired Student's t-tests were performed, where appropriate. Statistical significance was considered when $P<0.05$.

Results:

Tumour Cell-Induced Platelet Aggregation

Figure 9A:
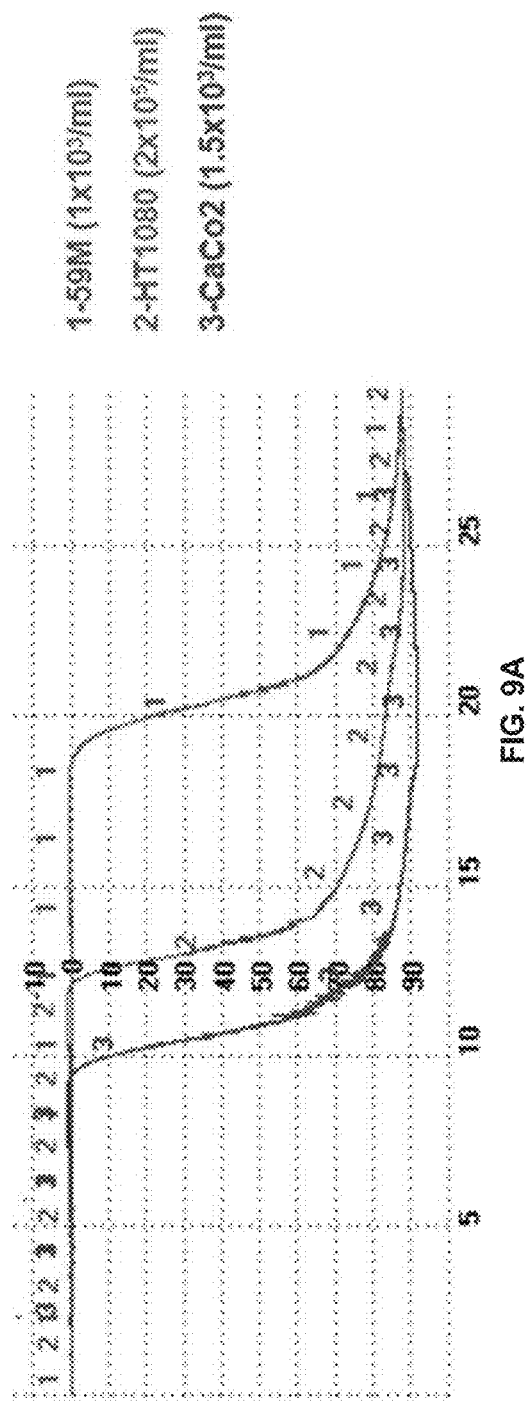
FIGS. 9A-9B illustrate HT1080, Caco-2 and 59M cells induced platelet aggregation.
Figure 9B:
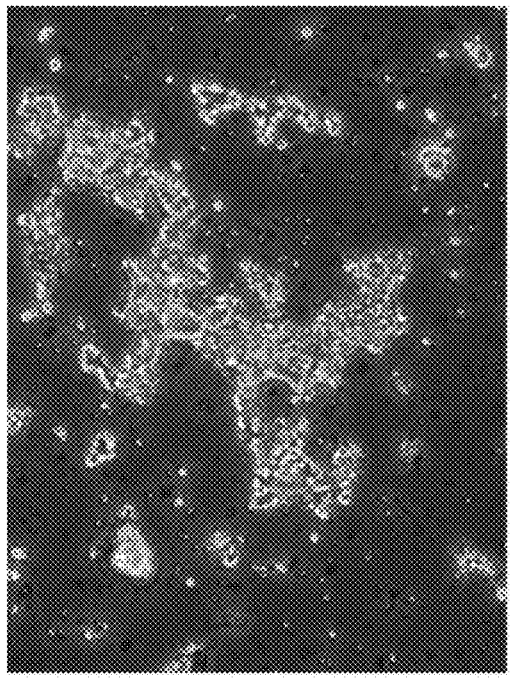

Caco-2, HT1080 and 59M cells were tested for their ability to induce platelet aggregation. When platelets were incubated in the aggregometer for 30 min at 37° C. without the addition of tumor cells, no platelet aggregation was detected. However, all cell lines were able to induce platelet aggregation (FIGS. 9A-9B). Since the concentration of $2 \times 10^5$/ml (HT1080 cells), $1.5 \times 10^3$/ml (CaCo2 cells) and $1 \times 10^3$/ml (59M cells) were sufficient to induce platelet aggregation, all remaining experiments were performed at this cell density.

Inhibition of Tumour Cell-Induced Platelet Aggregation

Figure 10A:
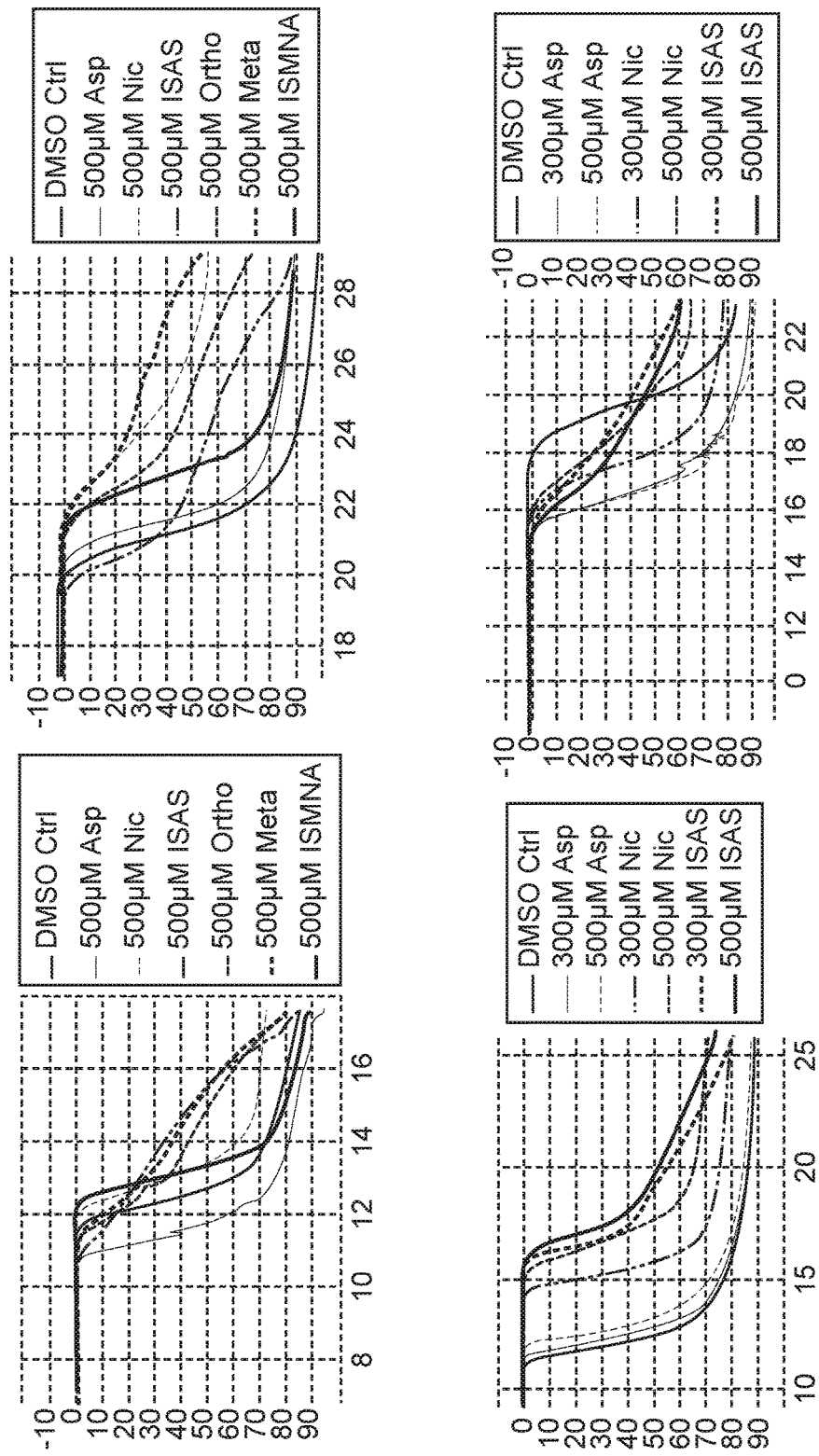
FIGS. 10A-10B illustrate the pharmacological effect of aspirin prodrugs on TCIPA. Representative traces (FIG. 10A) and the statistical analysis (FIG. 10B) showing the effects of Aspirin, ST0702, ISAS, orthonitrate and metanitrate at two different concentrations (300 and 500 µM) on TCIPA. TCIPA was induced by HT1080 cells ($2\times10^5$/ml), CaCO$_2$ cells ($1.5\times10^3$/ml) and 59M cells ($1\times10^3$/ml). Aggregated platelets with tumour cells in the absence of inhibitors were used as controls. Bars are mean±s.e.mean from four separate experiments. *P<0.05; ***P<0.01, treatments versus control.
Figure 10B:
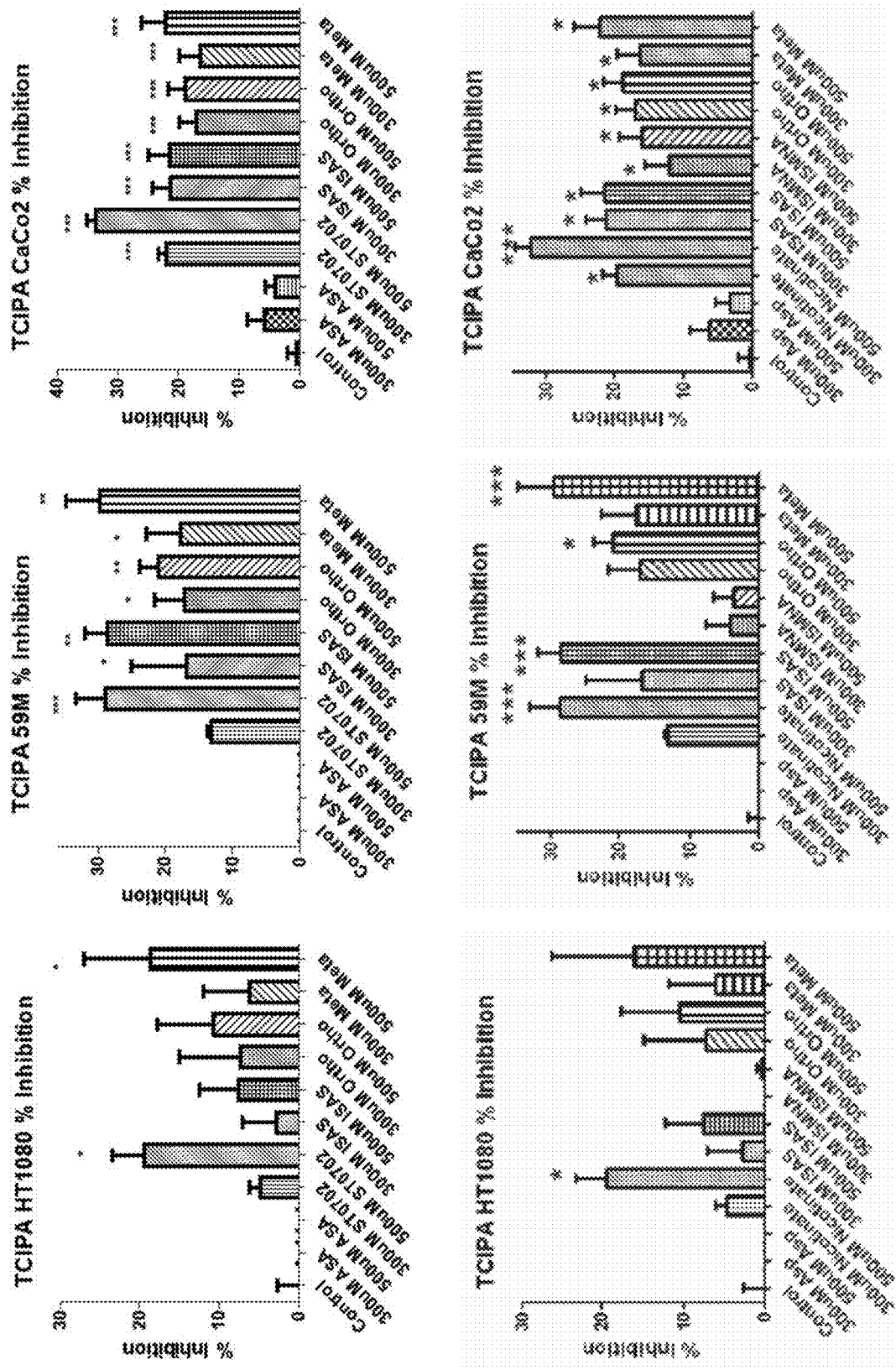
Figure 13A:
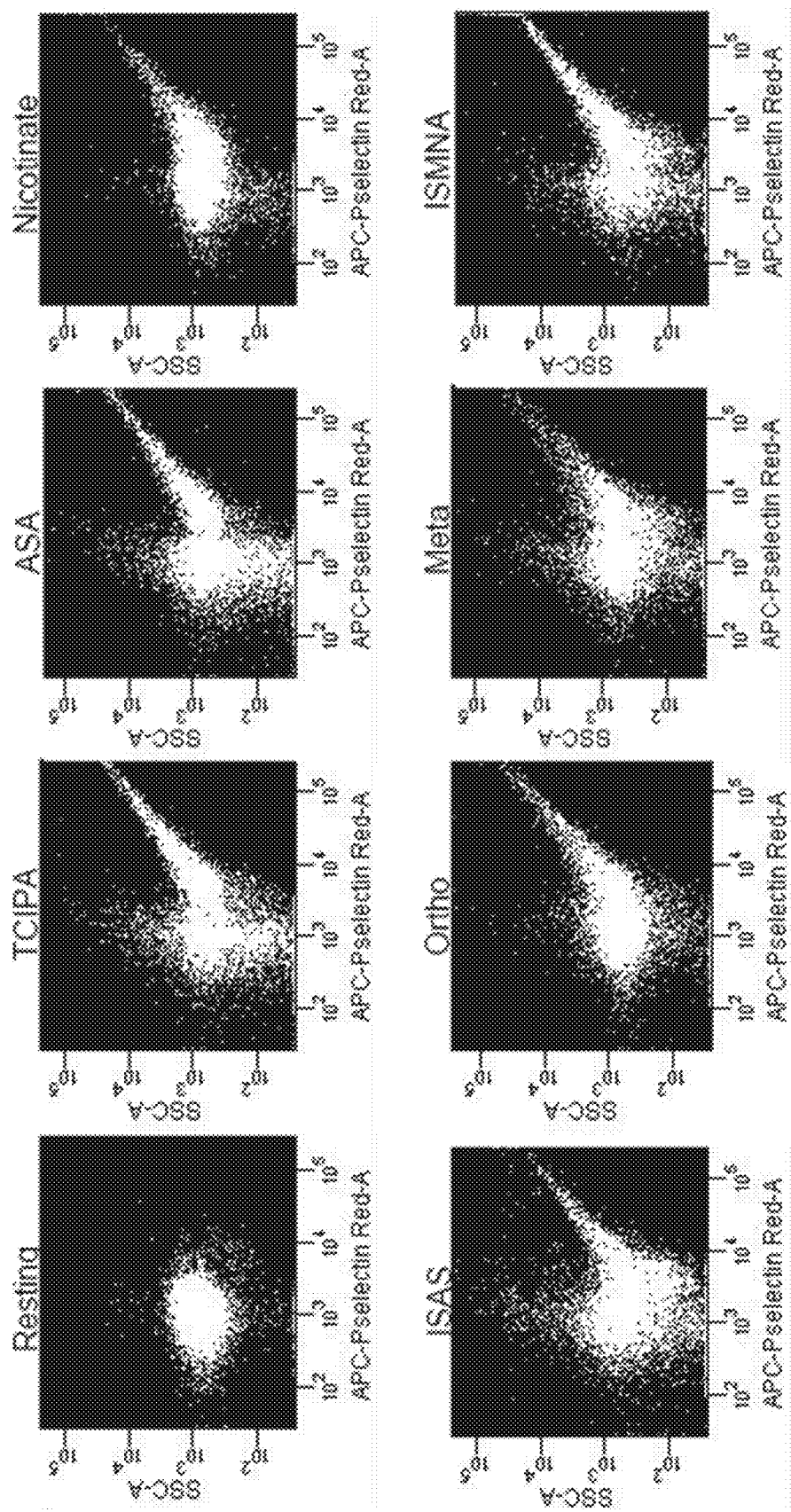

Different aspirin prodrugs and regular aspirin which inhibit the $TXA_2$ pathway were evaluated as inhibitors of TCIPA. First, platelet suspensions were preincubated with aspirin and prodrugs. Aspirin, Nicotinate, ISAS, ISMNA, Otho and Meta at two different concentrations (300 and 500 µM) were used to inhibit TCIPA in Caco2, HT1080 and 59M cell lines. Aspirin did not exert any significant effect on TCIPA (FIGS. 10A-10B). However, this concentration of aspirin inhibited collagen-induced aggregation by 56±7% (n=4) and abolished arachidonic acid (100 µM)-induced aggregation (n=4). In contrast to aspirin, nicotinate consistently inhibited TCIPA in all three cell lines, as shown by aggregometry (FIGS. 10A-10B) and phase contrast microscopy (FIGS. 11A-11G). Interestingly, nicotinate was the only aspirin prodrug that inhibited platelet aggregation induced by HT1080 (FIGS. 10A-10B). In addition, ISAS, Ortho and Meta were able to inhibit platelet aggregation induced by Caco-2 and 59M cells (FIGS. 10A-10B, 11A-11G). However, ISMNA only inhibited platelet aggregation induced by Caco-2 cells (FIGS. 10A-10B, 11A-11G). When tumour cells (Caco2 and 59M) were preincubated with nicotinate, no effect on TCIPA was observed (p>0.05, n=4).

Effects of ISAS, ST0702, Ortho- and Metanitrate or Aspirin on Tumour Cell-Induced Platelet Aggregation as Measured by Aggregometry ST0702 consistently inhibited TCIPA in response to all three cell lines, as shown by aggregometry (FIGS. 10A-10B) and phase contrast microscopy (FIGS. 11A-11G). Only ST0702 and the NO-releasing orthonitrate inhibited platelet aggregation induced by HT1080 (FIGS. 4A-4C). In addition, ISAS, orthonitrate and metanitrate inhibited platelet aggregation induced by Caco-2 and 59M cells (FIGS. 10A-10B, 11A-11G). In contrast, aspirin (300-500 µM) did not exert a significant effect on TCIPA (FIGS. 10A-10B). However, as expected aspirin (300 µM) inhibited collagen-induced aggregation by 56±7% (n=4). The general pattern of TCIPA inhibition was consistent with the observations of platelet-cancer masses detected by microscopy following treatment with aspirin or the prodrugs (FIGS. 11A-11G).

MMP-2 Release Measured by Zymography

As MMP-2 is released during TCIPA, zymographic analysis was conducted to study whether or not MMP-2 was involved in our experiments. We have previously shown that the pro-MMP-2 is the major gelatinase detected during platelet aggregation induced by both HT1080 and Caco2 cells (Jurasz et al., 2001; Medina et al., 2006). Therefore, we studied the release of MMP-2 in platelet aggregation induced by 59M. In our studies, we found that pro-MMP-2 was also released during TCIPA, as shown by the 72 kDa band (FIGS. 12A-12B). However, aspirin and all prodrugs (300 uM) failed to prevent the release of pro-MMP-2 during platelet aggregation induced by 59M cells (P>0.05; n=4), indicating that all drugs did not exert any effect on MMP-2 release (FIGS. 12A-12B).

Measurement of Platelet P-Selectin During TCIPA.

For these experiments, 59M cells were used. The interactions of platelets with HT1080 and Caco-2 cells have been previously characterized by our group (Jurasz et al., 2001; Medina et al., 2006). The interactions of platelets with 59M cells induced a significant (P<0.005; n=4) increase in the number of copies of P-selectin on platelet surface (FIG. 12A).

Effects of Inhibitors on P-Selectin During TCIPA

Flow cytometry performed on platelets pre-incubated with aspirin and prodrugs (300 µM) and then activated by 59M cells was analyzed. Nicotinate (ST0702) significantly (P<0.01, n=4) inhibited 59M-mediated increase in total P-selectin (FIGS. 12A-12B). In addition, ortho (orthonitrate) and meta were able to significantly (P<0.05, n=4) reduce the expression of P-selectin on platelet surface (FIGS. 12A-12B). In contrast, aspirin (ASA) and ISAS and ISMNA failed to prevent the increase in platelet surface abundance of P-selectin (P>0.05, n=4) (FIGS. 12A-12B).

ST0702 Inhibits TCIPA Under Flow Conditions

Figure 14D:
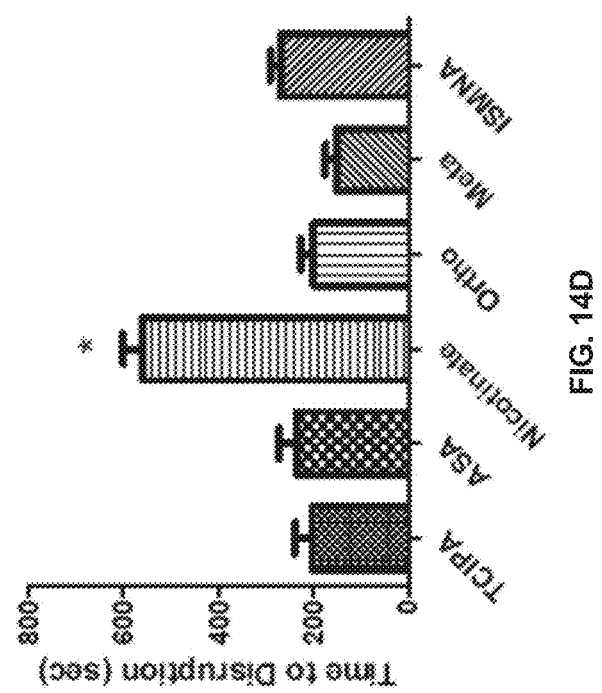

Following levitation of a 59M cell cluster in the trap for 10 min (FIG. 14A), platelet perfusion was initiated. Platelets approached the aggregate within 1 min and established contact with its periphery. Complete platelet 'encapsulation' of the aggregate was seen within 2 min (FIG. 14B). Platelet activation (identified as a transition to a gel-like sheet around the cell cluster) occurred within 4 min from platelets-cell cluster contact and resulted in the cancer aggregate disruption (FIG. 14D). ST0702 was the only inhibitor that significantly arrested TCIPA (P<0.05, n=4) (FIG. 14D).

Figure 15:
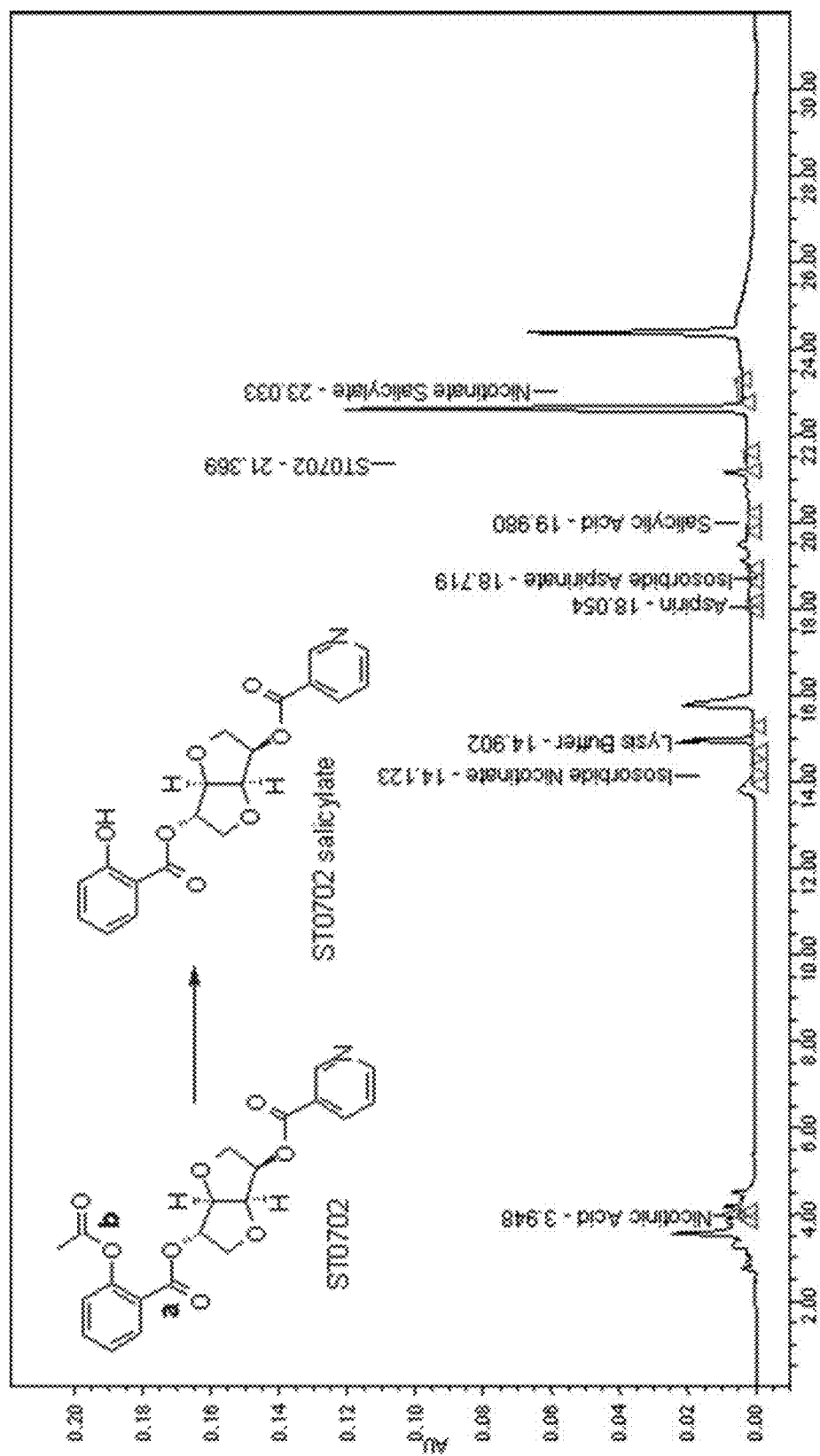
FIG. 15 shows HPLC chromatogram of cell lysate following TCIPA inhibition with ST0702 (500 µM). At the termination of a TCIPA experiment, HPLC analysis indicated that the CaCo-2/platelet cells contained a mixture of ST0702 (21.36 min) along with 33.7% of its deacetylated esterase mediated hydrolysis product isosorbide-2-salicylate-5-nicotinate (23.03 min), along with smaller amounts of aspirin (18.05 min). Aspirin is deacylated as a result of its mechanism of COX-1 inhibition to salicylic acid (18.71 min). Isosorbide-5-nicotinate (14.13 min) was also observed as a byproduct of ST0702 hydrolysis.

ST0702 Releases Small Amounts of Aspirin and its Salicylate During the TCIPA Experiment Following the TCIPA experiment with HT1080 or CaCo-2 cells, supernatants were collected for further analysis along with the cellular pellets which were lysed in the presence of esterase/protease inhibitors. The supernatants and lysis fractions were analysed by HPLC (FIG. 15). This indicated that in the presence of cancer cell and platelet esterases, ST0702 produces substantial amounts of its deacylated metabolite (isosorbide-2-salicylate-5-nicotinate (ST0702-salicylate), FIG. 15) along with smaller amounts of aspirin, salicylic acid, nicotinic acid and isosorbide-5-nicotinate. There were no significant differences between the supernatants or lysates following stimulation with CaCo-2 or HT1080 cells.

ST0702 Salicylate Inhibits TCIPA and ADP-Induced Platelet Aggregation

Figure 16B:
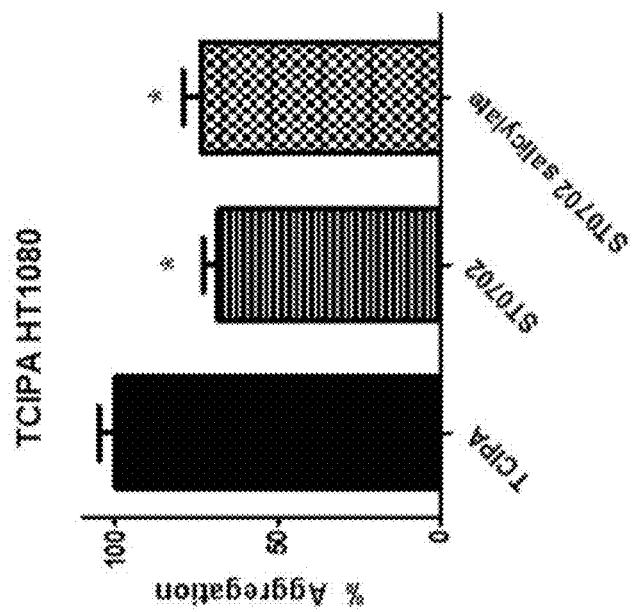
Figure 16A:
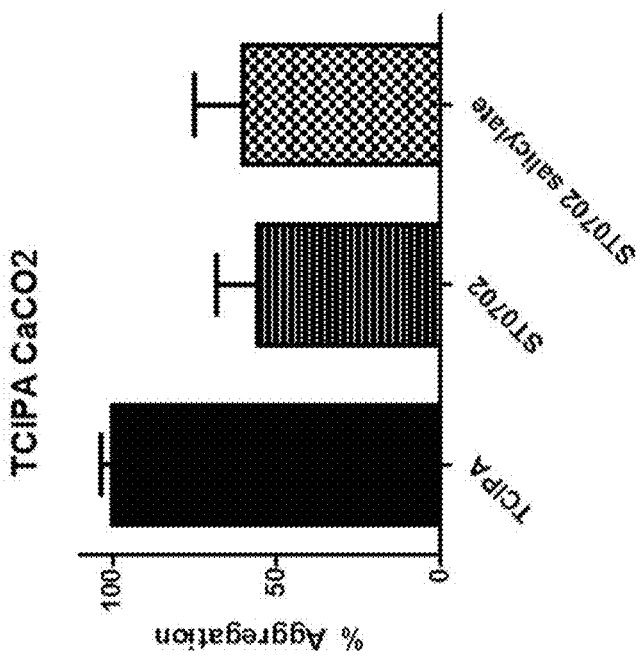

To further study the mechanism of action of ST0702 in TCIPA, more experiments were carried out with its in vitro metabolites identified in the HPLC experiments: nicotinic acid, isosorbide-5-nicotinate and the ST0702 salicylate. ST0702 salicylate inhibit TCIPA in response to HT1080 and Caco-2 cells under no flow conditions (FIG. 16A), however, unlike the parent ST0702, the salicylate did not inhibit TCIPA under flow conditions (FIG. 16D). Unlike its aspirin-releasing parent ST0702, the salicylate did not inhibit collagen-induced platelet aggregation (FIG. 16B). However, the salicylate inhibited ADP-induced aggregation in PRP (FIG. 16C), an effect that became significant in the presence of the esterase inhibitor eserine, which protected the salicylate from further hydrolysis in response to esterases in PRP. Unlike ST0702, the salicylate did not inhibit TCIPA in the ultrasound trap model, indicating that under flow conditions, its ADP inhibitory properties were insufficient to prevent TCIPA. The remaining fragments identified in cell lysates by HPLC (nicotinic acid and isosorbide-5-nicotinate) did not inhibit TCIPA at up to 3 mM.

Discussion and Conclusion

The main function of platelets is the maintenance of vascular haemostasis. Platelets also play crucial roles in the pathogenesis of vascular thrombosis and disease. There is increasing evidence that platelet-cancer cell interactions participate in the complex multi step process of carcinogenesis including blood-borne metastasis. When platelets are activated the arachidonic acid cascade is initiated, leading to TXA2 synthesis. This reaction is catalysed by a number of enzymes, the most important being cyclooxygenase (COX) which converts arachidonic acid to prostaglandin H2 (PGH2) and thromboxane synthase which converts PGH2 to TXA2. TXA2 mediates one of major pathways of platelet aggregation by stimulating platelet thromboxane receptors leading to activation of platelet inositol phosphate pathways and an increase in intracellular Ca2+ and release of dense- and α-granules. Aspirin reduces the synthesis of TXA2 by irreversibly inhibiting platelet COX, blocking PGG2 production. Aspirin preferentially inhibits the COX-1 isoform of the enzyme, but its effects on COX-2 are an important part of the explanation for its anti-inflammatory and putative anti-cancer effects. Numerous studies have shown an inverse relationship between aspirin consumption and cancer incidence (Elwood et al., 2009; Rothwell et al., 2011).

Epidemiological and randomized trial data indicates that aspirin-mediated cancer preventative effects are related to dose, duration of use and length of follow up (Langley et al., 2011). The strongest evidence for an anti-cancer effect of aspirin is from patients with COX-2 over-expressing tumours, suggesting the effect is dose dependent considering aspirin's COX-1 selectivity. The evidence for a therapeutic effect of aspirin treatment in cancer patients is more equivocal. Two recent nonrandomized trials have reported a reduction in colorectal and breast cancer specific mortality (Chan et al., 2009; Holmes et al., 2010), however several older studies failed to detect an improvement in survival in patients on high dose aspirin (Lebeau B et al., 1993; Lipton A et al., 1982). Consistent with its limited therapeutic efficacy, aspirin fails to inhibit TCIPA in vitro (Medina et al., 2006). The implication of this is that in stimulating platelet activation and recruitment cancer cells can surmount the COX-1 blockade resulting from pharmacologically relevant levels of aspirin. In this context we assessed aspirin pro-drugs as inhibitors of TCIPA because of their greater efficacy and potency in response to classical platelet stimuli such as collagen and ADP and ability to produce additional metabolites including NO (ortho and metanitrates), salicylic acid (ISAS) or niacin (ST0702).

The isosorbide-based aspirin pro-drugs caused significant inhibition of TCIPA in response to HT1080, 59M and Caco-2 cell lines. Of the test compounds, the niacin aspirin co-drug ST0702 most consistently inhibited platelet aggregation under static conditions but all of the prodrugs exhibited some activity. It's worth mentioning that nicotinic acid has been shown to mildly inhibit platelet aggregation, an effect which differs from other anti-platelet drugs such as aspirin suggesting potential opportunities for therapeutic combination in this field, however, in this study, nicotinic acid by itself did not inhibit TCIPA up to 3 mM (Serebruany et al, 2010)

Evaluation of tumour cell-platelet interactions, has usually been performed under static conditions. We have recently reported the development of a new method to study TCIPA under flow conditions using an ultrasound standing wave trap (Bazou et al., 2011). The approach permits the study of TCIPA and assessment of inhibitors under more realistic (patho)physiological conditions where flow dynamics play a role in adhesion and tumour mass rupture. Initial studies with this method have shown that platelet recruitment and degranulation by tumour cells are followed by rupture of tumour cell mass with consequent evolution of satellite aggregates. Aspirin treatment fails to delay the rupture of the tumour cell-platelet aggregates (Bazou et al., 2011). ST0702 was the only pro-drug to effectively inhibit flow-induced TCIPA. Surprisingly the NO-releasing pro-drugs (ortho and metanitrate) did not interfere with TCIPA under flow conditions. Nitroaspirins or NO donating aspirin compounds (e.g. NCX4016) have been extensively evaluated in vitro and in vivo as chemopreventative agents but not in models of TCIPA. Interpretation of the biochemical efficacy of NCX4016 is moreover complicated by its metabolic conversion to a quinone methide that irreversibly modifies cellular biomolecules leading to reduced viability. Nevertheless there is substantial evidence that NO release from nitro-aspirins can augment the anti-platelet effects of the aspirin component. The ortho- and metanitrate pro-drugs evaluated in the present study are among the first to release aspirin and NO. These inhibit ADP-induced aggregation in a manner that is sensitive to inhibition by the soluble guanylate cyclase inhibitor ODQ (Jones et al., 2009). One interpretation of the present data is that NO amplification of aspirin effects may be insufficient to prevent key steps in the mutual activation of platelets and cancer cells. One of the main pathways involved in TCIPA is the MMP-2 dependent pathway. We have previously shown the requirement for activated MMP-2 to induce the MMP-2 dependent pathway both in agonist and platelet aggregation induced by HT1080 and CaCo2 cells (Jurasz et al., 2001; Medina et al., 2006). Phenanthroline, a synthetic broad spectrum MMP inhibitor, was able to reduce TCIPA and the abundance of receptors on platelet surface. Therefore, we studied the effect of aspirin prodrugs on MMP-2 release during TCIPA. We have found that none of the test drugs significantly reduced the release of MMP-2. These results clearly indicate that the effect of aspirin prodrugs on TCIPA is MMP-independent. TCIPA is partly mediated by ADP (Alonso-Escolano et al., 2004; Medina et al., 2006). Although ADP is a weak agonist it is essential for platelet function. The release of ADP from activated platelets and stimulation of P2Y2 purinergic receptors accounts for the non-TXA2, non-MMP-2-mediated pathway of platelet aggregation. In order to find out why ST0702 was more efficacious inhibitor of TCIPA than its analogous prodrugs, we analysed platelet-tumour cell supernatants and lysates following TCIPA experiments using a HPLC method capable of separating and identifying potential metabolites of ST0702. The most prominent byproduct of cellular hydrolysis of ST0702 was the corresponding salicylate ester resulting from esterase mediated-deacylation (ST0702 salicylate). Interestingly, ST0702 salicylate was able to inhibit ADP-stimulated platelet aggregation but not collagen-induced aggregation, which is more aspirin sensitive. Furthermore the salicylate caused inhibition of TCIPA under no flow conditions implicating ADP blockade in the mode of action of ST0702. Notably, the salicylate did not inhibit TCIPA under flow conditions, unlike ST0702, which can also release aspirin suggesting that ADP inhibition by ST0702 is not sufficient for the inhibitory effects observed. The present results are consistent with our previous studies where scavenging ADP with potato and human apyrase decreased TCIPA (Alonso-Escolano et al., 2006; Jurasz et al., 2003; Medina et al., 2006). Similar effects to apyrase could be demonstrated using selective inhibitors of the P2Y12 receptor such as 2-methylthio-AMP (Alonso-Escolano et al., 2004). Since platelet receptors mediate TCIPA, we next studied the changes in the abundance of P-selectin on platelets induced by 59M cells. In fact, P-selectin and its association with mucin is likely to mediate TCIPA in a variety of mucin producing cancers. In our study, we found that 59M cells increased the number of copies of P-selectin, as measured by flow cytometry. These results are in agreement with our previous studies in vitro (Medina et al., 2006). We next studied the effect of aspirin prodrugs on Pselectin in TCIPA. Indeed, we have previously shown that TCIPA inhibition is strongly associated with P-selectin down-regulation (Medina et al., 2006). Our results showed that ST0702 again was the most efficacious inhibitor of P-selectin expression during TCIPA. Interestingly, orthonitrate and metanitrate but not ISAS, significantly reduced P-selectin expression but to a lesser extent. This may be due to the fact that ortho- and metanitrates are able to produce NO and aspirin, unlike ISAS which liberates aspirin. In conclusion, isosorbide-based aspirin pro-drugs, which are potent inhibitors of collagen and ADP induced platelet aggregation, also inhibit TCIPA whereas aspirin does not. The aspirin-nicotinic acid codrug ST0702 inhibited TCIPA under no flow and flow conditions. The inhibitory effect of ST0702 appears to be due to its dual capacity to release aspirin as well as its blockade of ADP and P-selectin-mediated function, partly through its salicylate byproduct. This separates ST0702 from aspirin and related NO releasing analogs. The therapeutic potential of ST0702 as aspirin prodrug and inhibitor of TCIPA in the prevention of blood-borne metastasis merits further attention.

REFERENCES a. Tran H A, Anand S S, Hankey G J, Eikelboom J W. Aspirin resistance. Thrombosis Research. 2007; 120(3): 337-46; b. Poulsen T S, Kristensen S R, Korsholm L, Haghfelt T, Jørgensen B, Licht P B, et al. Variation and importance of aspirin resistance in patients with known cardiovascular disease. Thrombosis Research. 2007; 120 (4): 477-84; c. Poulsen T S, Jørgensen B, Korsholm L, Bjom Licht P, Haghfelt T, Mickley H. Prevalence of aspirin resistance in patients with an evolving acute myocardial infarction. Thrombosis Research. 2007; 119 (5): 555-62; e. Dawson J, Quinn, T., Rafferty, M., Higgins, P., Walters, M R. Aspirin resistance and compliance with therapy. Cardiovascular Therapeutics. 2010; g. Herlitz J, Tóth P P, Nesdal J. Low-Dose Aspirin Therapy for Cardiovascular Prevention: Quantification and Consequences of Poor Compliance or Discontinuation. American Journal of Cardiovascular Drugs. 2010; 10(2): 125-41 10.2165/11318440-000000000-00000; h. Shantsila E, Lip G. 'Aspirin resistance' or treatment non-compliance: Which is to blame for cardiovascular complications? Journal of Translational Medicine. 2008; 6(1): 47; i. Schwartz K A, Schwartz D E, Ghosheh K, Reeves M J, Barber K, DeFranco A. Compliance as a critical consideration in patients who appear to be resistant to aspirin after healing of myocardial infarction. The American journal of cardiology. 2005; 95(8): 973-5; j. Burney K D, Krishnan K, Ruffin M T, Zhang D, Brenner D E. Adherence to Single Daily Dose of Aspirin in a Chemoprevention Trial: An Evaluation of Self-report and Microelectronic Monitoring. Arch Fam Med. 1996; 5(5): 297-300; k. Coleman J L, Alberts M J. Effect of Aspirin Dose, Preparation, and Withdrawal on Platelet Response in Normal Volunteers. The American journal of cardiology. 2006; 98(6): 838-41; 6. Moriarty, L. M., et al. Discovery of a "true" aspirin prodrug. *J Med Chem* 51, 7991-7999 (2008); 7. Jones, M., et al. Isosorbide-based aspirin pro-drugs: integration of nitric oxide releasing groups. *J Med Chem* 52, 6588-6598 (2009); Nordestgaard, B. H., et al. Lipoprotein (a) as a cardiovascular risk factor: Current status. Eur Heart J 31, 2844-2853 (2010) 30. Oertel, J., Wirthmuller, R. & Kastner, M. Alpha naphthyl acetate esterase in human blood cells with different molecular weights. *Blut* 46, 101-106 (1983); Alonso-Escolano D, Medina C, Cieslik K, Radomski A, Jurasz P, Santos-Martinez M J, et al. (2006). PKCä Mediates Platelet-Induced Breast Cancer Cell Invasion. J Pharmacol Exp Ther 18:373-80. Alonso-Escolano D, Strongin A Y, Chung A W, Deryugina E I, Radomski M W (2004). Membrane type-1 matrix metalloproteinase stimulates tumour cell-induced platelet aggregation: role of receptor glycoproteins. Br J Pharmacol 141(2): 241-252. Bazou D, Santos-Martinez M J, Medina C, Radomski M W (2011). Elucidation of flow-mediated tumour cell-induced platelet aggregation using an ultrasound standing wave trap. Br J Pharmacol 162(7): 1577-1589. Chan A T, Ogino S, Fuchs C S (2009). Aspirin Use and Survival After Diagnosis of Colorectal Cancer. JAMA 302(6): 649-658. Elwood P C, Gallagher A M, Duthie G G, Mur L A J, Morgan G (2009). Aspirin, salicylates, and cancer. Lancet 373(9671): 1301-1309. Holmes M D, Chen W Y, Li L, Hertzmark E, Spiegelman D, Hankinson S E (2010). Aspirin intake and survival after breast cancer. J Clin Oncol. 28(9): 1467-1472. Jones M, Inkielewicz I, Medina C, Santos-Martinez M J, Radomski A, Radomski M W, et al. (2009). Isosorbide-Based Aspirin Prodrugs: Integration of Nitric Oxide Releasing Groups. J Med Chem 52(21): 6588-6598. Jurasz P, Alonso-Escolano D, Radomski M W (2004). Platelet-cancer interactions: mechanisms and pharmacology of tumour cell-induced platelet aggregation. Br J Pharmacol 143: 819-826. Jurasz P, North S, Venner P, Radomski M W (2003). Matrix metalloproteinase-2 contributes to increased platelet reactivity in patients with metastatic prostate cancer: a preliminary study. Thromb Res 112(1-2): 59-64. Jurasz P, Sawicki G, Duszyk M, Sawicka J, Miranda C, Mayers I, et al. (2001). Matrix Metalloproteinase 2 in Tumor Cell-induced Platelet Aggregation: Regulation by Nitric Oxide. Cancer Res 61(1): 376-382. Langley R E, Burdett S, Tierney J F, Cafferty F, Parmar M K, Venning G (2011). Aspirin and cancer: has aspirin been overlooked as an adjuvant therapy? Br J Cancer doi: 10.1038/bjc.2011.289. Lebeau B, Chastang C, Muir J F, Vincent J, Massin F, Fabre C (1993). No effect of an antiaggregant treatment with aspirin in small cell lung cancer treated with CCAVP16 chemotherapy. Results from a randomized clinical trial of 303 patients. The "Petites Cellules" Group. Cancer 71(5): 1741-1745. Lipton A, Scialla S, Harvey H, Dixon R, Gordon R, Hamilton R, et al. (1982). Adjuvant antiplatelet therapy with aspirin in colo-rectal cancer. J Med 13(5-6): 419-429; Medina C, Jurasz P, Santos-Martinez M J, Jeong S S, Mitsky T, Chen R, et al. (2006). Platelet Aggregation-Induced by Caco-2 Cells: Regulation by Matrix Metalloproteinase-2 and Adenosine Diphosphate. J Pharmacol Exp Ther 317(2): 739-745. Radomski M W, Jenkins D C, Holmes L, Moncada S (1991). Human colorectal adenocarcinoma cells: differential nitric oxide synthesis determines their ability to aggregate platelets. Cancer Res 51(22): 6073-6078. Rothwell P M, Fowkes F G R, Belch J F F, Ogawa H, Warlow C P, Meade T W (2011). Effect of daily aspirin on long-term risk of death due to cancer: analysis of individual patient data from randomised trials. Lancet 377(9759): 31-41. Serebruany V, Malinin A, Aradi D, Kuliczkowski W, Norgard N B, Boden W E (2010). The in vitro effects of niacin on platelet biomarkers in human volunteers. Thromb Haemost 104:311-7

The invention claimed is:

1. A pharmaceutical dose formulation comprising a compound having the structure (III) and/or a pharmaceutically acceptable salt and/or hydrates thereof,

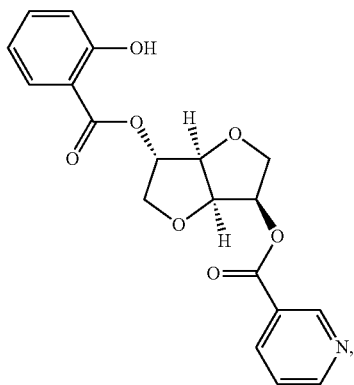

(III)

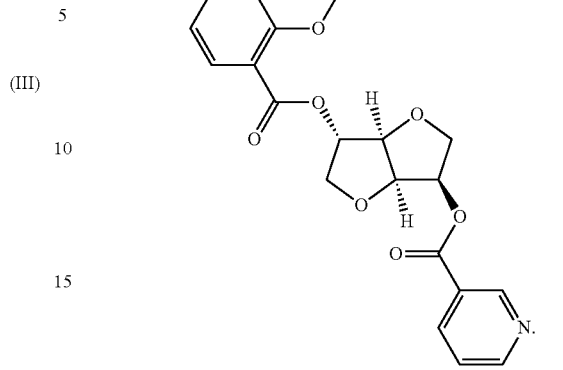

(II)

wherein the pharmaceutical dose formulation does not comprise a compound having the structure (II), 2. The pharmaceutical dose formulation of claim 1, wherein the compound has the structure (III).

3. A method for the inhibition of tumor cell induced platelet aggregation comprising administering to a subject in need thereof an effective amount of the pharmaceutical dose formulation of claim 1 or 2.

* * * * *